(12) United States Patent
Green et al.

(10) Patent No.: US 6,919,076 B1
(45) Date of Patent: Jul. 19, 2005

(54) CONJUGATES OF AGENTS AND TRANSGLUTAMINASE SUBSTRATE LINKING MOLECULES

(75) Inventors: Howard Green, Brookline, MA (US); Bruce Compton, Lexington, MA (US); George Corey, Newton, MA (US); Philippe Djian, Paris (FR)

(73) Assignee: Pericor Science, Inc., Boston, MA (US)

( * ) Notice: Subject to any disclaimer, the term of this patent is extended or adjusted under 35 U.S.C. 154(b) by 0 days.

(21) Appl. No.: 09/359,920

(22) Filed: Jul. 22, 1999

Related U.S. Application Data

(63) Continuation-in-part of application No. 09/234,358, filed on Jan. 20, 1999, now Pat. No. 6,267,957.
(60) Provisional application No. 60/071,908, filed on Jan. 20, 1998.

(51) Int. Cl.$^7$ ................... A61K 38/00; A61K 38/45; A61K 38/48; C12N 11/02; C07K 17/02

(52) U.S. Cl. .............. 424/94.5; 424/59; 424/94.6; 424/94.63; 424/401; 435/16; 435/177; 435/193; 435/196; 514/2; 530/402; 530/812

(58) Field of Search .................. 435/16, 193, 177, 435/196, 174; 424/94.5, 94.63, 59, 401, 94.6; 514/2; 530/402, 812

(56) References Cited

U.S. PATENT DOCUMENTS

| | | | |
|---|---|---|---|
| 3,867,365 A | 2/1975 | Stahmann et al. | |
| 3,975,342 A | 8/1976 | Gross | |
| 3,979,508 A | 9/1976 | Stahmann et al. | |
| 3,990,459 A | 11/1976 | Papantoniou | |
| 4,048,301 A | 9/1977 | Papantoniou | |
| 4,152,411 A | 5/1979 | Schall, Jr. | |
| 4,252,784 A | 2/1981 | Levine | |
| 4,277,460 A | 7/1981 | Kojima et al. | |
| 4,279,996 A | 7/1981 | Yoshioka et al. | 435/69 |
| 4,284,537 A | 8/1981 | Beachey | |
| 4,338,214 A | 7/1982 | Fischer et al. | 252/545 |
| 4,369,037 A | 1/1983 | Matsunaga et al. | 8/127.51 |
| 4,407,965 A | 10/1983 | Yanaihara | |
| 4,474,754 A | 10/1984 | Shimizu et al. | |
| 4,517,175 A | 5/1985 | Iwabuchi et al. | 424/70 |
| 4,521,334 A | 6/1985 | Beachey | |
| 4,532,207 A | 7/1985 | Brewer et al. | 435/68 |
| 4,534,881 A | 8/1985 | Sikes et al. | |
| 4,543,325 A | 9/1985 | Albert et al. | |
| 4,572,800 A | 2/1986 | Shimizu et al. | |
| 4,597,967 A | 7/1986 | Beachey | |
| 4,626,495 A | 12/1986 | Sakaguchi | |
| 4,631,190 A | 12/1986 | Shen et al. | 424/85 |
| 4,645,503 A | 2/1987 | Lin et al. | |
| 4,663,286 A | 5/1987 | Tsang et al. | |
| 4,680,338 A | 7/1987 | Sundoro | |
| 4,695,562 A | 9/1987 | Beachey et al. | |
| 4,699,778 A | 10/1987 | Marty | 424/59 |
| 4,701,521 A | 10/1987 | Ryser et al. | 530/322 |
| 4,705,682 A | 11/1987 | Moeller et al. | 525/70 |
| 4,726,942 A | 2/1988 | Lang et al. | 424/47 |
| 4,728,639 A | 3/1988 | Beachey | |
| 4,744,933 A | 5/1988 | Rha et al. | |
| 4,749,620 A | 6/1988 | Rha et al. | |
| 4,804,746 A | 2/1989 | Yoshida et al. | |
| 4,832,946 A | 5/1989 | Green | 424/70 |
| 4,839,168 A | 6/1989 | Abe et al. | 424/74 |
| 4,847,240 A | 7/1989 | Ryser et al. | 514/12 |
| 4,879,116 A | 11/1989 | Fox et al. | 424/682 |
| 4,880,911 A | 11/1989 | Brewer et al. | 530/351 |
| 4,885,169 A | 12/1989 | Gazzani | 424/104 |
| 4,892,733 A | 1/1990 | Bichon et al. | |

(Continued)

FOREIGN PATENT DOCUMENTS

| | | |
|---|---|---|
| AU | A-13742 | 9/1988 |
| CA | 2094658 | 4/1993 |
| CA | 2245310 A1 | 2/1999 |

(Continued)

OTHER PUBLICATIONS

Asayama, et al. "Synthesis of Novel Polyampholyte Comb–Type Copolymers Consisting of a Poly(L–lysine) Backbone and Hyaluronic Acid Side Chains for a DNA Carrier," Bioconjugate Chem., 1998, vol. 9, pp. 476–481.

(Continued)

Primary Examiner—David M. Naff
(74) Attorney, Agent, or Firm—Wolf, Greenfield & Sacks, P.C.

(57) ABSTRACT

Methods, products, compositions and kits are provided for attaching agents to tissue with a linking molecule in the presence of transglutaminase. The linking molecule and/or agent is a substrate of transglutaminase. The agent can be a nonprotein or an enzyme such as cholinesterase or phosphodiesterase. The transglutaminase may be exogenously added or be endogenous in tissue. In specific embodiments, the agent is not a transglutaminase substrate and the linking molecule is a substrate for transglutaminase containing at least two contiguous linked glutamines or at least three contiguous linked lysines, and may be a polymer. A conjugate of the agent and the linking molecule may be applied to tissue, and in the presence of transglutaminase covalently bonded to the tissue via the linking molecule. A complementary linking molecule rich in lysines may be first attached to the tissue in the presence of transglutaminase, and then covalently bonded to a glutamine-containing linking molecule of the conjugate in the presence of transglutaminase. In another embodiment a linking molecule containing multiple glutamines is covalently bonded to tissue in the presence of transglutaminase, and an agent containing multiple lysines is covalently bonded to the linking molecule in the presence of transglutaminase. Alternatively, the linking molecule contains multiple lysines and the agent contains multiple glutamines. Two tissues can be sealed together by holding the tissues in contact with each other in the presence of transglutalinase.

32 Claims, 2 Drawing Sheets

U.S. PATENT DOCUMENTS

| | | |
|---|---|---|
| 4,908,404 A | 3/1990 | Benedict et al. |
| 4,973,473 A | 11/1990 | Schneider et al. ............ 424/63 |
| 5,017,229 A | 5/1991 | Burns et al. |
| 5,075,019 A | 12/1991 | Evans et al. .................. 252/34 |
| 5,080,888 A | 1/1992 | Grollier et al. ............... 424/61 |
| 5,091,173 A | 2/1992 | Buultjens et al. ............ 424/70 |
| 5,098,833 A | 3/1992 | Lasky et al. |
| 5,100,673 A | 3/1992 | Bader et al. ................ 424/451 |
| 5,100,956 A | 3/1992 | O'Lenick, Jr. ............ 514/54.1 |
| 5,116,320 A | 5/1992 | Lo Duca |
| 5,132,230 A | 7/1992 | Rosenthal et al. |
| 5,135,913 A | 8/1992 | Pickart ........................ 424/16 |
| 5,156,956 A | 10/1992 | Motoki et al. ............. 435/68.1 |
| 5,162,505 A | 11/1992 | Dean et al. .............. 530/391.5 |
| 5,166,078 A | 11/1992 | McMahon et al. |
| 5,166,320 A | 11/1992 | Wu et al. |
| 5,175,112 A | 12/1992 | Amiral et al. |
| 5,202,431 A | 4/1993 | della Valle et al. ........ 536/55.1 |
| 5,232,984 A | 8/1993 | Hubbell et al. ............ 525/54.1 |
| 5,258,041 A | 11/1993 | Guire et al. .................. 623/66 |
| 5,263,992 A | 11/1993 | Guire |
| 5,334,640 A | 8/1994 | Desai et al. ................... 525/56 |
| 5,354,844 A | 10/1994 | Beug et al. ................. 530/345 |
| 5,358,706 A | 10/1994 | Marlin et al. |
| 5,366,958 A | 11/1994 | Weiner et al. |
| 5,405,939 A | 4/1995 | Suhadolnik et al. |
| 5,409,904 A | 4/1995 | Hecht et al. |
| 5,436,291 A | 7/1995 | Levy et al. |
| 5,449,720 A | 9/1995 | Russell-Jones et al. |
| 5,461,081 A | 10/1995 | Ali et al. |
| 5,470,829 A | 11/1995 | Prisell et al. |
| 5,470,956 A | 11/1995 | Hayashi et al. |
| 5,487,977 A | 1/1996 | de Weck |
| 5,490,980 A | 2/1996 | Richardson et al. ........ 424/94.6 |
| 5,501,863 A | 3/1996 | Rössling et al. |
| 5,505,952 A | 4/1996 | Jiang et al. |
| 5,510,329 A | 4/1996 | Belkin et al. |
| 5,521,291 A | 5/1996 | Curiel et al. |
| 5,523,222 A | 6/1996 | Page et al. |
| 5,525,336 A | 6/1996 | Green et al. ............... 424/94.5 |
| 5,529,986 A | 6/1996 | Larsson et al. |
| 5,548,064 A | 8/1996 | Russell-Jones et al. |
| 5,559,104 A | 9/1996 | Romeo et al. |
| 5,573,934 A | 11/1996 | Hubbell et al. ............. 435/177 |
| 5,576,188 A | 11/1996 | Schlaeppi et al. |
| 5,578,442 A | 11/1996 | Desai et al. .................. 435/1.1 |
| 5,578,598 A | 11/1996 | Abe et al. |
| 5,582,172 A | 12/1996 | Papisov et al. |
| 5,587,175 A | 12/1996 | Viegas et al. |
| 5,587,301 A | 12/1996 | Hawkins et al. ........... 435/69.1 |
| 5,591,648 A | 1/1997 | Hayashi et al. |
| 5,593,658 A | 1/1997 | Bogdanov et al. |
| 5,595,893 A | 1/1997 | Pometto, III et al. |
| 5,595,897 A | 1/1997 | Midoux et al. |
| 5,618,790 A | 4/1997 | Kennedy et al. |
| 5,620,013 A | 4/1997 | Bretton |
| 5,624,896 A | 4/1997 | Axworthy et al. |
| 5,629,011 A | 5/1997 | Illum |
| 5,633,230 A | 5/1997 | Twist, et al. .................. 514/15 |
| 5,635,380 A | 6/1997 | Naftilan et al. |
| 5,635,383 A | 6/1997 | Wu et al. |
| 5,635,385 A | 6/1997 | Leopold et al. |
| 5,635,447 A | 6/1997 | Sanders |
| 5,646,120 A | 7/1997 | Sumner-Smith et al. ...... 514/14 |
| 5,646,133 A | 7/1997 | Sanders |
| 5,654,381 A | 8/1997 | Hrkach et al. |
| 5,656,609 A | 8/1997 | Wu et al. |
| 5,658,592 A | 8/1997 | Tanihara et al. |
| 5,658,915 A | 8/1997 | Abe et al. |
| 5,660,851 A | 8/1997 | Domb |
| 5,661,040 A | 8/1997 | Huff et al. |
| 5,674,849 A | 10/1997 | Twist et al. .................... 514/15 |
| 5,674,977 A | 10/1997 | Gariépy |
| 5,677,276 A | 10/1997 | Dickerson et al. |
| 5,681,568 A | 10/1997 | Goldin et al. |
| 5,686,113 A | 11/1997 | Speaker et al. |
| 5,693,509 A | 12/1997 | Cotton et al. |
| 5,693,751 A | 12/1997 | Sakurai et al. |
| 5,693,851 A | 12/1997 | Sielcken et al. |
| 5,705,270 A | 1/1998 | Soon-Shiong et al. |
| 5,711,915 A | 1/1998 | Siegmund et al. |
| 5,716,614 A | 2/1998 | Katz et al. ................. 424/94.3 |
| 5,718,900 A | 2/1998 | Hill et al. |
| 5,723,301 A | 3/1998 | Burke et al. |
| 5,738,864 A | 4/1998 | Schacht et al. |
| 5,756,069 A | 5/1998 | Torchilin et al. |
| 5,760,200 A | 6/1998 | Miller et al. ................... 536/21 |
| 5,763,160 A | 6/1998 | Wang |
| 5,766,585 A | 6/1998 | Evans et al. |
| 5,770,229 A | 6/1998 | Tanihara et al. |
| 5,770,572 A * | 6/1998 | Gershoni ...................... 514/13 |
| 5,770,628 A | 6/1998 | Cantoro |
| 5,773,577 A | 6/1998 | Cappello .................... 530/350 |
| 5,780,054 A | 7/1998 | Tardi et al. |
| 5,783,178 A | 7/1998 | Kabanov et al. ......... 424/78.31 |
| 5,783,566 A | 7/1998 | Mislick |
| 5,783,669 A | 7/1998 | Hawkins et al. |
| 5,783,691 A | 7/1998 | Malson et al. |
| 5,788,959 A | 8/1998 | Singh ........................ 424/85.1 |
| 5,789,230 A | 8/1998 | Cotten et al. |
| 5,789,531 A | 8/1998 | Sumner-Smith et al. .... 530/328 |
| 5,792,645 A | 8/1998 | Beug et al. |
| 5,795,860 A | 8/1998 | Witt et al. |
| 5,795,909 A | 8/1998 | Shashoua et al. ........... 514/449 |
| 5,817,644 A | 10/1998 | Gustafson et al. ............ 514/54 |
| 5,820,882 A | 10/1998 | Hubbell et al. |
| 5,830,731 A | 11/1998 | Seed et al. |
| 5,830,913 A | 11/1998 | Ogawa et al. |
| 5,831,001 A | 11/1998 | Twist et al. ................. 530/328 |
| 5,834,444 A | 11/1998 | Falk et al. |
| 5,834,556 A | 11/1998 | Desai et al. ................ 525/54.1 |
| 5,837,533 A | 11/1998 | Boutin |
| 5,837,747 A | 11/1998 | Soon-Shiong et al. |
| 5,842,477 A | 12/1998 | Naughton et al. |
| 5,843,770 A | 12/1998 | Ill et al. |
| 5,846,530 A | 12/1998 | Soon-Shiong et al. |
| 5,846,951 A | 12/1998 | Gregoriadis ................. 514/54 |
| 5,849,839 A | 12/1998 | Hubbell et al. |
| 5,851,229 A | 12/1998 | Lentz et al. |
| 5,851,527 A | 12/1998 | Hansen |
| 5,858,746 A | 1/1999 | Hubbell et al. |
| 5,861,156 A | 1/1999 | George et al. |
| 5,869,466 A | 2/1999 | Russell-Jones et al. |
| 5,871,710 A | 2/1999 | Bogdanov et al. |
| 5,874,297 A | 2/1999 | Wu et al. |
| 5,874,500 A | 2/1999 | Rhee et al. |
| 5,876,698 A | 3/1999 | Schmitt-Willich et al. |
| 5,876,744 A | 3/1999 | Della Valle et al. |
| 5,882,645 A | 3/1999 | Toth et al. |
| 5,885,609 A | 3/1999 | Amiji |
| 5,902,795 A | 5/1999 | Toole et al. |
| 5,916,585 A | 6/1999 | Cook et al. |
| 5,922,859 A | 7/1999 | Birnstiel et al. |
| 5,925,626 A | 7/1999 | della Valle et al. |
| 5,939,323 A | 8/1999 | Valentini et al. |
| 5,945,100 A | 8/1999 | Fick |
| 5,955,578 A | 9/1999 | Pierschbacher et al. ..... 530/345 |
| 5,958,443 A * | 9/1999 | Viegas et al. ............... 424/427 |
| 5,962,015 A | 10/1999 | Delrieu et al. |
| 5,965,152 A | 10/1999 | Galin et al. |
| 5,965,404 A | 10/1999 | Buschle et al. |

| Patent No. | Date | Inventors | | Patent No. | Date | Inventors |
|---|---|---|---|---|---|---|
| 5,965,493 A | 10/1999 | Grieco et al. | | 6,372,499 B1 | 4/2002 | Midoux et al. |
| 5,965,532 A | 10/1999 | Bachovchin | | 6,378,527 B1 | 4/2002 | Hungerford et al. |
| 5,968,500 A | 10/1999 | Robinson | | 6,379,965 B1 | 4/2002 | Boutin |
| 5,968,542 A | 10/1999 | Tipton | | 6,387,390 B1 | 5/2002 | Deaver et al. |
| 5,972,326 A | 10/1999 | Galin et al. | | 6,391,336 B1 | 5/2002 | Royer |
| 5,972,707 A | 10/1999 | Roy et al. | | 6,395,029 B1 | 5/2002 | Levy |
| 5,980,883 A | 11/1999 | Tanihara et al. | | 6,395,254 B1 | 5/2002 | Sinn et al. |
| 5,990,095 A | 11/1999 | Falk et al. | | 6,420,519 B1 | 7/2002 | Hwang et al. |
| 5,993,856 A | 11/1999 | Ragavan et al. | | 2001/0031740 A1 | 10/2001 | Unger et al. |
| 5,994,311 A | 11/1999 | Eichner et al. | | 2001/0034363 A1 | 10/2001 | Li et al. |
| 5,998,588 A | 12/1999 | Hoffman et al. | | 2001/0039336 A1 | 11/2001 | Miller et al. |
| 6,007,816 A | 12/1999 | St. John et al. | | 2002/0013408 A1 | 1/2002 | Rhee et al. |
| 6,013,526 A | 1/2000 | Takahara et al. | | 2002/0016304 A1 | 2/2002 | Maruyama et al. .......... 514/44 |
| 6,013,641 A | 1/2000 | Lussow et al. ............... 514/54 | | 2002/0019439 A1 | 2/2002 | Grieco et al. |
| 6,022,735 A | 2/2000 | Curiel et al. | | 2002/0044937 A1 | 4/2002 | Birnstiel et al. |
| 6,022,866 A | 2/2000 | Falk et al. | | 2002/0052000 A1 | 5/2002 | Parthasarathy et al. |
| 6,025,138 A | 2/2000 | Hawkins et al. | | | | |
| 6,025,337 A | 2/2000 | Truong et al. | | FOREIGN PATENT DOCUMENTS | | |
| 6,027,741 A | 2/2000 | Cialdi et al. | | DE | 4335025 A1 | 4/1995 |
| 6,030,954 A | 2/2000 | Wu et al. | | DE | 19647863 A | 5/1998 |
| 6,030,958 A | 2/2000 | Burns et al. | | EP | 0 009 498 B1 | 1/1979 |
| 6,037,329 A | 3/2000 | Baird et al. | | EP | 0107053 A2 | 5/1984 |
| 6,037,467 A | 3/2000 | Stahl et al. | | EP | 0111385 A2 | 6/1984 |
| 6,054,312 A | 4/2000 | Larocca et al. | | EP | 015898 A2 | 8/1985 |
| 6,054,313 A | 4/2000 | Bryan et al. | | EP | 0188309 A2 | 7/1986 |
| 6,069,133 A | 5/2000 | Chiou et al. | | EP | 0285 474 | 10/1988 |
| 6,077,663 A | 6/2000 | Curiel et al. | | EP | 0 354 847 A2 | 2/1990 |
| 6,086,863 A | 7/2000 | Ritter et al. | | EP | 0359996 A2 | 3/1990 |
| 6,089,234 A | 7/2000 | Bretton | | EP | 0421478 A2 | 4/1991 |
| 6,103,525 A | 8/2000 | Stern et al. | | EP | 0481 504 | 10/1991 |
| 6,107,326 A | 8/2000 | Jori | | EP | 0499164 A1 | 8/1992 |
| 6,110,208 A | 8/2000 | Soranzo et al. | | EP | 0511 116 | 10/1992 |
| 6,114,388 A | 9/2000 | Geffard | | EP | 0 599 303 A2 | 11/1993 |
| 6,117,427 A | 9/2000 | Hill et al. | | EP | 651055 A2 * | 5/1995 |
| 6,123,965 A | 9/2000 | Jacob et al. | | EP | 0693293 A1 | 1/1996 |
| 6,127,170 A | 10/2000 | Boutin | | EP | 0704221 A | 4/1996 |
| 6,127,448 A | 10/2000 | Domb | | EP | 0725141 A1 | 8/1996 |
| 6,129,956 A | 10/2000 | Morra et al. | | EP | 0727223 A1 | 8/1996 |
| 6,132,462 A | 10/2000 | Li | | EP | 0615 745 | 5/1997 |
| 6,136,793 A | 10/2000 | Falk et al. | | EP | 0752474 A1 | 8/1997 |
| 6,138,680 A | 10/2000 | Bretton | | EP | 0808844 A2 | 11/1997 |
| 6,150,461 A | 11/2000 | Takei et al. ................... 525/63 | | EP | 0950406 A2 | 10/1999 |
| 6,159,955 A | 12/2000 | Asculai et al. | | EP | 0992794 A2 | 4/2000 |
| 6,166,130 A | 12/2000 | Rhee et al. | | EP | 0999278 A1 | 5/2000 |
| 6,177,257 B1 | 1/2001 | Macphee et al. | | EP | 1067116 A1 | 1/2001 |
| 6,177,259 B1 | 1/2001 | Yuan et al. | | EP | 1067117 A1 | 1/2001 |
| 6,200,595 B1 | 3/2001 | Motoyashiki et al. | | EP | 1067173 A1 | 1/2001 |
| 6,221,397 B1 | 4/2001 | Russell-Jones et al. | | EP | 1067174 A1 | 1/2001 |
| 6,221,959 B1 | 4/2001 | Kabanov et al. | | FR | 2092875 A | 1/1972 |
| 6,224,893 B1 | 5/2001 | Langer et al. | | FR | 2659352 | 9/1991 |
| 6,229,009 B1 | 5/2001 | Lambert et al. | | FR | 2719316 A1 | 11/1995 |
| 6,235,313 B1 | 5/2001 | Mathiowitz et al. ........ 424/486 | | GB | 2038628 A | 7/1980 |
| 6,235,726 B1 | 5/2001 | Burns et al. | | GB | 2185397 A | 7/1987 |
| 6,251,392 B1 | 6/2001 | Hein et al. | | JP | 57163318 A | 10/1982 |
| 6,251,599 B1 | 6/2001 | Chen et al. | | JP | 58225028 A | 12/1983 |
| 6,271,216 B1 | 8/2001 | Mello et al. | | JP | 61073665 A | 4/1986 |
| 6,271,344 B1 | 8/2001 | Turley | | JP | 61172807 | 8/1986 |
| 6,274,322 B1 | 8/2001 | Curiel et al. | | JP | 63253028 A | 10/1988 |
| 6,280,745 B1 | 8/2001 | Flore et al. | | JP | 1097861 A | 4/1989 |
| 6,281,192 B1 | 8/2001 | Leahy et al. | | JP | 2-204407 | 2/1990 |
| 6,281,341 B1 | 8/2001 | Mares-Guia et al. | | JP | 02169511 | 6/1990 |
| 6,303,752 B1 | 10/2001 | Olsen et al. ................. 530/350 | | JP | 2193914 A | 7/1990 |
| 6,306,993 B1 | 10/2001 | Rothbard et al. ........... 526/304 | | JP | 03038511 | 2/1991 |
| 6,323,278 B2 | 11/2001 | Rhee et al. | | JP | 03083908 | 4/1991 |
| 6,331,289 B1 | 12/2001 | Klaveness et al. | | JP | 4215760 A | 8/1992 |
| 6,331,525 B1 | 12/2001 | Chiou et al. | | JP | 4244015 A | 9/1992 |
| 6,348,508 B1 | 2/2002 | Denick, Jr. et al. | | JP | 05085924 | 4/1993 |
| 6,353,022 B1 | 3/2002 | Schneider et al. | | JP | 5-56785 | 5/1993 |
| 6,353,055 B1 | 3/2002 | Kabanov et al. | | JP | 7216000 A | 8/1995 |
| 6,355,690 B1 | 3/2002 | Tsuji | | WO | WO85/01442 | 4/1985 |
| 6,368,586 B1 | 4/2002 | Jacob et al. | | WO | WO90/13256 A1 | 11/1990 |

| | | |
|---|---|---|
| WO | WO91/04058 | 4/1991 |
| WO | WO91/08770 | 6/1991 |
| WO | WO 91/09958 | 7/1991 |
| WO | WO91/17761 A1 | 11/1991 |
| WO | WO 92/07871 | 5/1992 |
| WO | WO92/12238 | 7/1992 |
| WO | WO92/20316 | 11/1992 |
| WO | WO 93/04701 | 3/1993 |
| WO | WO 9309176 A2 | 5/1993 |
| WO | WO93/16733 | 9/1993 |
| WO | WO 93/21941 | 11/1993 |
| WO | WO 94/14464 | 7/1994 |
| WO | WO94/18945 | 9/1994 |
| WO | WO94/23738 | 10/1994 |
| WO | WO 95/11038 | 4/1995 |
| WO | WO95/18636 | 7/1995 |
| WO | WO 95/23611 A1 | 9/1995 |
| WO | WO95/24929 | 9/1995 |
| WO | WO 9530020 A1 | 11/1995 |
| WO | WO95/34647 | 12/1995 |
| WO | WO96/04001 | 2/1996 |
| WO | WO96/07731 | 3/1996 |
| WO | WO96/11990 | 4/1996 |
| WO | WO96/12405 A1 | 5/1996 |
| WO | 96/15810 * | 5/1996 |
| WO | WO96/15811 | 5/1996 |
| WO | WO 96/21036 | 7/1996 |
| WO | WO96/30536 | 10/1996 |
| WO | WO 97/33552 | 9/1997 |
| WO | WO 97/40854 | 11/1997 |
| WO | WO 97/41215 | 11/1997 |
| WO | WO98/13381 | 4/1998 |
| WO | WO98/35056 A1 | 8/1998 |
| WO | WO98/39011 | 9/1998 |
| WO | WO 98/52614 | 11/1998 |
| WO | WO99/02683 A1 | 1/1999 |
| WO | WO 99/36570 | 7/1999 |
| WO | WO99/65529 | 12/1999 |
| WO | WO00/10609 | 3/2000 |
| WO | WO00/50101 | 8/2000 |
| WO | WO 01/13957 | 3/2001 |
| WO | WO 01/32850 A1 | 5/2001 |
| WO | WO 01/62297 | 8/2001 |

OTHER PUBLICATIONS

Maruyama, et al. "Nanoparticel DNA Carrier with Poly(L–lysine) Grafted Polysaccharide Copolymer and Poly(D,Llactic acid)," Bioconjugate Chem., 1998, vol. 8, pp. 735–742.

Maruyama, et al. Communications "Comb–Type Polyctions Effectively Stabilize DNA Triplex," Bioconjugate Chem. 1997, vol. 8, pp. 3–6.

Wagner, et al. "Transferrin–polycation conjugates as carriers for DNA uptake into cells," Proc. Natl. Acad. Sci. USA, 1990, vol. 87, pp. 3410–3414.

Lemaitre, et al. "Specific antiviral activity of a poly (L–lysine)–conjugated oligodeoxyribonucleotide sequence complementary to vesicular stomatitis virus N protein mRNA initiation site," Proc. Natl. Acad. Sci. USA, 1987, vol. 84, pp. 648–652 Abstract.

International Search Report for PCT/US00/20211, mailed Nov. 15, 2000.

Kabanov, A.V., et al. "DNA Complexes with Polycations for the Delivery of Genetic Material into Cells" Bioconjugate Chem., 1995, vol. 6, pp. 7–20.

LeBaron, R.G., et al., "Hyaluronate Binding Properties of Versican" J Biol Chem, May 15, 1992; vol. 267, No. 14, pp. 10003–10010. Abstract.

Peach, R.J., et al. "Identification of Hyaluronic Acid Binding Sites in the Extracellular Domain of CD44" J Cell Biol., Jul. 1993; vol. 122, No. 1, pp. 257–64. Abstract.

Degols, G, et al. "Oligonucleotide–poly(L–lysine)–Heparin Complexes: Potent Sequences–Specific Inhibitors of HIV–1 infection" Bioconjugate Chem. Jan.–Feb. 1994; vol. 5, No. 1, pp. 8–13. Abstract.

Shen, W.C., et al. "Poly(L–lysine) has Different Membrane Transport and Drug–Carrier Properties when Complexed with Heparin" Proc. Natl Acad Sci USA, 1981, vol. 78, No. 12, pp. 7589–7593. Abstract.

Delmage, J.M., et al. "The Selective Suppression of Immunogenicity by Hyaluronic Acid." Ann Clin Lab Sci, Jul.–Aug. 1986, vol. 16, No. 4, pp. 303–310. Abstract.

Abuchowski, A., et al. "Effect of Covalent Attachment of Polyethylene Glycol on Immunogenicity and Circulating Life of Bovine Liver Catalase." J Biol Chem., Jun. 10, 1977; vol. 252, No. 11, pp. 3582–3586. Abstract.

Wu, G.Y., et al. "Evidence for Targeted Gene Delivery to Hep G2 Hepatoma Cells in vitro." Biochemistry. Feb. 9, 1988., vol. 27, No. 3, pp. 887–892. Abstract.

Jian et al., Biosci. Biotech. and Biochem., 61(1):188–190, 1997 Abstract only.

Chemical Abstracts, 89:18 (1978).

Chemical Abstracts, 89:292 (1978).

Nogawa et al., Proceed. Int'l. Symp. Control. Rel. Bioact. Mater., 26:821–822, 1999.

Blackwell et al., Federation Proceedings, 36(1):98–101, 1973.

Smith et al., Arthritis & Rheumatism, 37(1):125–136, 1994.

Hembry et al., Am. J. Path. 143(2):628–642, 1993.

Park et al., Proceed. Int'l. Symp. Control. Rel. Bioact. Mater., 26:823–824, 1999.

Anderson, Annals New York Academy of Sciences, Dept of Pathology and Macromolecular Science, Case Western Reserve University, Cleveland Ohio, 44106, "Poly (amino acids)", pp67–75.

Li et al., Cancer Res, 58:2404–2409, 1981.

Cera et al., Anti–Cancer Drug Design, 7:143–151, 1992.

Park et al., Prep Biochem Biotechnol, 29(4):353–370, 1990 Abstract only.

Hu et al., Tissue Engineering, 6(6):558–593(9), 2000.

Mayurama, et al., Bioconjug Chem, 9(2):292–299, 1998 Abstract only.

Asayama et al., Bioconjug Chem, 10(2):246–253, 1999 Abstract only.

Hu et al., J. Biomed Mat Res, 47(1):79–84, 1999 Abstract only.

Zu, et al. Biosci, Biotech Biochem, 61(1):188–190, 1997.

Asayama et al., Bioconjug Chem, 9:476–481, 1998.

Greenberg,"Transglutaminases: Multifunctional Cross–linking Enzymes that Stabilize Tissues," FASEB J., 5:3071–3077 (1991).

Hohl, "Cornified Cell Envelope," Dermatologica, 180:201–211 (1990).

Hohl, "Characterization of Human Loricrin," J. of Biological Chemistry, 266:6626–6636 (1991).

Kvedar, "Characterization of Sciellin, a Precursor to the Cornified Envelope of Human Keratinocytes,"Differentiation, 49:195–204 (1992).

Markova, Profilaggrin Is a Major Epiderman Calcium–Binding Protein, Molecular and Cellular Biology, 13:613–625 (1993).

Marvin, "Cornifin, a Cross–Linked Envelope Precursor in Keratinocytes that Is Down–Regulated by Retinoids," *Biochemistry*, 89:11029–11030 (1992).

Mehrel, "Identification of a Major Keratinocyte Cell Envelope Protein, Loricrin," *Cell*, 61:1103–1112 (1990).

Phillips, "Primary Structure of Keratinocyte Transglutaminase," *Biochemistry*, 87:9333–9337 (1990).

Rice, "Presence in Human Epidermal Cells of a Soluble Protein Precursor of the Cross–Linked Envelope: Activation of the Cross–Linking by Calcium Ions," *Cell*, 18:681–694 (1979).

Rice, "The Cornified Envelope of Terminally Differentiated Human Epidermal Keratinocytes Consists of Cross–Linked Protein," *Cell*, 11:417–422 (1977).

Simon, "Enzymatic Cross–Linking of Involucrin and Other Proteins by Keratinocyte Particulates in Vitro," *Cell*, 40:677–683 (1985).

Steven, "Biosynthetic Pathways of Filaggrin and Loricrin—Two Major Proteins Expressed by Terminally Differentiated Epidermal Keratinocytes," *J. of Structural Biology*, 104:150–162 (1990).

Highley, "The Epidermal Keratinization Process," *Cosmetics & Toiletries*, 99:57–62 (1984).

Rialdi et al., "Filaggrin Overview; Functions and Cosmetic Aim," *Cosmetics & Toiletries*, 103:89–94 (1988).

(Abstract) *Women's Wear Daily*, p. 6 (Oct. 9, 1992).

Banks–Schlegal, "Involucrin Synthesis and Tissue Assembly by Keratinocytes in Natural and Cultured Human Epithelia," *J. of Cell Biology*, 90:732, 737 (1981).

Eckert, "Structure and Evolution of the Human Involucrin Gene," *Cell*, 46:583–589 (1986).

Etoh, "Involucrin Acts as a Transglutaminase Substrate at Multiple Sites," *Biochemical and Biophysical Research Communications*, 136:51–56 (1986).

Fietz, "The cDNA–deduced Amino Acid Sequence for Trichohyalin, A Differentiation Marker in the Hair Follicle, Contains a 23 Amino Acid Repeat," *J. of Cell Biology*, 110:427–436 (1990).

Steven, M. et al., "Protein Composition of Cornified Cell Envelopes of Epidermal Keratinocytes," *J. Cell Science*, 107:693–700 (1994).

Folk, "Transglutaminase (Guinea Pig Liver)," *Methods in Enzymology*, vol. 17A, 1970, p. 889–894, Tabor H. and C. Tabor, Eds.

Green, "Terminal Differentiation of Cultured Human Epidermal Cells," *Cell*, 11:405–416 (1977).

Davies, et al., *Adv. Exp. Med. Biol.* 250, 391–401 (1988).

Pober, J.S., et al., *Biochemistry*, vol. 17, No. 11:2163–2169 (1978).

Lajemi, M., et al., *Histochemical Journal* 29:593–606 (1997).

Kahlem, et al., *Proc. Natl. Sci., USA*, vol. 93, pp. 14580–14585 (Dec. 1996)(Appendix A).

International Search Report:PCT/US99/01193 (related PCT Case—H0535/7007WO).

Rothman, "Primary Open Angle Glaucoma and Medical Therapy For Glaucoma", The New York Eye and Ear Infimary, OKAP Review –Glaucoma, revised 2002, 8 pages.

Del Covered Drug List, MaineCare, Health Care for Maine People, GHS Data Management, 2002, 21 pages.

* cited by examiner

CONJUGATES OF AGENTS AND TRANSGLUTAMINASE SUBSTRATE LINKING MOLECULES

This application is a continuation-in-part of U.S. patent application Ser. No. 09/234,358, filed Jan. 20, 1999, now U.S. Pat. No. 6,267,957, the entire disclosure of which is incorporated herein by reference, and which claims benefit of U.S. Provisional Patent Application Ser. No. 60/071,908, filed Jan. 20, 1998.

FIELD OF THE INVENTION

This invention relates to the linkage of agents to tissue by trarsglutaminase and involves methods, products and kits relating thereto.

BACKGROUND OF THE INVENTION

Transglutaminases are a family of calcium-dependent enzymes mediating covalent cross-linking reactions between specific peptide bound γ-glutanyl residues and various primary amino groups of peptide-bound lysines or polyamines, acting as amine donor substrates (Davies, et al., Adv. Exp. Med. Biol. 250, 391–401, 1988). These enzymes stabilize biological structures via the formation of isopeptide cross-links. In mammals, at least five enzymatically active transglutaminases have been identified, cloned and sequenced. The number of proteins acting as glutaminyl substrates for transglutaminases is restricted, and no obvious consensus sequence around these substrates' glutamines has been found.

Three main lines of investigation have been conducted surrounding transglutaminases. These enzymes have been used to label membrane proteins and, in the absence of exogenous amines, to catalyze the formation of (γ-glutamyl) lysyl cross-links between them. The labeling is quite specific and can be carried out under mild (physiological) reaction conditions. Thus, for example, transglutaminases were used to study rhodopsin in the intact disc membrane, as only residues of rhodopsin located in the aqueous phase in the exposed side of the disc membranes were expected to be labeled. In these experiments, rhodopsin was labeled by transglutaminase using putrescine and dansylcadaverine as detectable substrates.

The role of transglutaminases in living cells also has been studied, for example, using the cell-penetrating labeled substrate fluoresceincadaverine for detecting amine acceptor protein substrates accessible to active transglutaminase in living cells. A similar strategy was employed using 5-(biotinamido)-pentylamine as a label. Such labeled substrates can be detected directly, for example by fluorescence, or can be detected indirectly, for example using antibodies, to identify native proteins to which the labeled substrate has been covalently attached by transglutaminase. See, Pober, J. S. et al., Biochemistry, Vol. 17, No. 11:2163–2169 (1978); Lajemi, M. et al., Histochemical Journal 29:593–606 (1997).

More recently, an investigation was carried out to determine if polyglutamine is a transglutaminase substrate. It was determined that as long as polypeptides including stretches of polyglutamine are rendered sufficiently soluble by the flanking residues, all were excellent substrates of transglutaminase. Based upon these studies, it was speculated that certain diseases such as Spinocerebellar ataxia Type I, Machado-Joseph disease, and Dentato-Rubral pallidoluysian atrophy which are characterized by proteins having polyglutamine stretches, may arise as a result of aggregation of such proteins acted upon by a transglutaminase.

It also is described in U.S. Pat. No. 5,525,336 (the disclosure of which is incorporated herein by reference in its entirety) that transglutaminas and corneocyte proteins, the natural substrates of transglutaminas, can be used together as cosmetic treatments to cross-link preparations of corneocyte proteins to the outer layer of skin, hair or nails to form a protective layer on the skin, hair or nails.

U.S. Pat. No. 5,490,980 describes selecting agents having or modifying agents to have an aliphatic amine, and then attaching those agents to skin, hair or nails using transglutaminase. While the idea was sound in principle, in practice the '980 applicants achieved results that were barely above background. (See Example Section of '980 patent). An aliphatic amine was applied in the examples as a single linking molecule or prophetically in clusters (according to a formula in the '980 patent). In selecting the amine moiety of the pair of known transglutaminase substrate moieties, the '980 patent taught away from using the carboxamide substrate moiety.

SUMMARY OF THE INVENTION

It has been discovered, surprisingly, that certain substrates of transglutaminase are particularly desirable for use as linking molecules to attach agents to proteinaceous material such as body tissue. It also has been discovered that molecules, including native peptides and conjugates according to the invention, can be screened to determine those that can be substrates of transglutaminases, and then such molecules can be attached to body tissue. Methods of attaching agents to body tissue and methods of screening molecules using transglutaminase are provided. In addition, compositions of matter suitable as substrates for transglutaminase and kits containing such molecules together with transglutaminase are provided.

According to one aspect of the invention, a method is provided for attaching a non-corneocyte protein, non-labeling agent to a body tissue. A conjugate of the agent and a linking molecule having a carboxamide, the linking molecule being a carboxamide-bearing substrate of transglutaminase, is applied to the body tissue. Transglutaminase also is applied to the body tissue, in an amount effective for cross-linking the conjugate to the body tissue via the linking molecule. The cross-linking then is allowed to occur. In certain embodiments the agent is not fibronectin (i.e., a nonfibronectin agent). In certain embodiments the agent is not an extracellular matrix protein (i.e. a non-extracellular protein agent). Preferably the linking molecule comprises a polymer of at least 3, 4 or 5 linked units, each unit being a carboxamide substrate of transglutaminase.

According to another aspect of the invention, a method is provided for attaching a non-corneocyte protein, non-labeling agent to a body tissue. The method involves selecting a non-corneocyte protein, non-labeling agent that is a carboxamide substrate for transglutaminase. The agent, in an isolated form, then is applied to the body tissue in the presence of a sufficient amount of transglutaminase to cross-link the isolated agent to the body tissue. The cross-linking then is allowed to occur. In this embodiment, the agent can be a conjugate of a native, non-corneocyte, non-labeling active agent and a linking molecule not native to the agent. It also is the case that the agent can be a native agent free of conjugation with groups not native to the agent. The agent in certain embodiments is a non-extracellular matrix protein agent.

In either of the foregoing embodiments, the linking molecule can be any number of a variety of molecules. In some embodiments, the linking molecule is at least one glutamine. The linking molecule, likewise, can be one bearing multiple reactive carboxamides, such as two or more contiguous linked L or D glutamines. D glutamines have the advantage of being physiologically more stable than L glutamines. In a preferred embodiment, the linking molecule is a polymer rich in carboxamides that are substrates of transglutaminase, such as a polymer rich in glutamine. The linking molecule also can be a polymer rich in both carboxamides and aliphatic amines, such as one rich in both glutamine and lysine. A polymer rich in glutamine, lysine, or glutamine and lysine is a molecule wherein at least 20% of the units of the polymer are glutamine, lysine or glutamine and lysine, respectively or wherein the molecule includes at least three, preferably four and most preferably five contiguous, linked transglutamines substrates, preferably linked by peptide bonds. A polymer rich in glutamines, lysines or glutamines and lysines, can be a polymer that contains at least 30% glutamines, lysines or glutamines and lysines, at least 40% glutamines, lysines or glutamines and lysines, or even 50% or more glutamines, or glutamines and lysines.

In certain preferred embodiments, the methods described above involve first preparing the body tissue for the attachment of the agent to the body tissue. In one important embodiment, a separate "complementary" linking molecule that is attachable to the linking molecule by transglutaminase is first attached to the body tissue to provide multiple, accessible linking sites for the attachment of the linking molecule to the body tissue. As used herein a pair of molecules which are covalently joined by transglutaminase are said to be complementary molecules. The complementary linking molecule can be attached to the body tissue by any suitable means, but preferably is attached by applying the complementary linking molecule to the body tissue, and applying transglutaminase to the body tissue in an amount effective for cross-linking the complementary linking molecule to the body tissue. Cross-linking then is allowed to occur. Preferably, the complementary linking molecule is a polymer rich in lysine, glutamine, or both glutamine and lysine.

Layers of such linking molecules can be attached to body tissue. To exemplify, polyglutamine could first be attached to the surface of a body tissue using transglutaminase. Then, polylysine could be attached to the polyglutamine using transglutaminase. Subsequently polyglutamine could be attached to the polylysine by transglutaminase, and so forth, to create by amplification alternating layers of such molecules on the body tissues, for example, for bulking purposes or to provide an even, continuous bed of reactive groups for linking an active agent to the body tissue.

For example, polymers comprising polyglutamine may first be attached to a body tissue as primary linking molecules. Then, polymers comprising the complementary linker (e.g. polylysine) can be attached to the body tissue via the polymers comprising polyglutamine. Finally, agents conjugated with polyglutamine then may be applied to the coated body surface and easily attached to the exposed amines of the polylysines.

In important embodiments, the native agent is not itself a substrate of transglutaminase. Thus, it is required that the agent be conjugated to a substrate of transglutaminase whereby the agent may be attached to the body tissue by such a substrate which acts as the linking group. It also is possible to modify peptide agents by adding a side group, whereby the agent which itself is not a substrate of transglutaminase is converted to a substrate of transglutaminnase.

According to the foregoing methods, the agents and conjugates are attached to proteinaceous material. The preferred proteinaceous material is body tissue, including the integument, a wound bed, internal organs or internal tissue of a living subject.

According to the foregoing methods, the agent can be any variety of agents, including cosmetics such as bulking agents, coloring agents, sunscreen agents, hair conditioning agents, hair fixative agents, anti-foaming agents, moisturizing agents, including humectants, and depilatories (i.e., hair removal agents), vitamins, film forming agents such as those used in hair fixatives or wound healing, insect repellants including louse repellants, anti-nerve gas or anti-neurotoxin agents such as enzymes including cholinesterase and phosphodiesterase, pharmaceutical agents, ligands of ligand-receptor complexes, receptors of ligand-receptor complexes, and the like. In one important embodiment, the agent is a member of a noncovalent coupling pair, such as biotin and avidin, to provide a universal linker as discussed in greater detail below. In certain embodiments, particularly those employing pharmaceutical agents, the bond between the agent and the linking molecule can be a bond which cleaves under normal physiological conditions or which can be caused to cleave specifically, for example, by light. In many instances where the agent is not itself a substrate of transglutaminase, the agent is a non-protein.

According to another aspect of the invention, a method is provided for attaching an agent to a body tissue. A linking molecule, that is covalently bonded to the agent in the presence of transglutaminase, is attached to the body tissue. Then, an agent that is a substrate of transglutaminase is applied to the body tissue. Transglutaminase also is applied to the body tissue, in an amount effective to cross-link the agent to the linking molecule. Cross-linking then is allowed to occur. The linking molecule can be attached to the body tissue by any suitable means, but preferably is itself a substrate of transglutaminase and preferably is attached to the body tissue by applying the linking molecule to the body tissue together with transglutaminase, the transglutaminase being present in an amount effective to cross-link the linking molecule to the body tissue. Preferred agents and linkers are as discussed above. Most preferred linking molecules are glutamine, lysine and polymers of glutamine and/or lysine or polymers that are rich in glutamine, or lysine, or both glutamine and lysine.

In this embodiment, the agent can be any substance including those listed above (with or without conjugated complementary linking molecules depending on whether the agent is itself a substrate of transglutaminase) but also including visible labels, extracellular matrix proteins and corneocyte proteins. Preferred body tissues are as described above. The transglutaminase may be endogenous transglutaminase.

According to another aspect of the invention, a method is provided for attaching an agent to a body tissue. The method involves first attaching to the body tissue a linking molecule which is covalently bondable to the agent in the presence of transglutaminase. Then, the method involves applying to the body tissue having the linking molecule attached thereto an agent that is a substrate of transglutaminase and that is covalently bondable to the linking molecule in the presence of transglutaminases, the applying carried out in the presence of the sufficient amount of taansglutaminase effective to cross-link the agent to the cross-linking molecule. Cross-linking then is allowed to occur. Preferred agents, linking molecules and body tissues are as described above.

According to another aspect of the invention, a method for attaching a nonextracellular matrix protein, preferably nonlabeling, agent to a body tissue is provided. The method involves applying to the body tissue a conjugate of the agent and a linking molecule, the linking molecule being a polymer carrying at least 3 aliphatic amines spaced along the polymer, applying to the body tissue transglutaminase in an amount effective for crosslinking the linking molecule to the body tissue, and allowing crosslinking to occur. The aliphatic amines can be the side chain of L or D lysines. D lysines have the advantage of being physiologically more stable than L lysines. Most preferably, the linking molecule is selected from the group consisting of at least 3, at least 4 and at least 5 contiguous lysines attached to one another directly by peptide bonds. The polymer also can be one rich in aliphatic amines such as one rich in lysines, as described above. Preferred agents and body tissues are as described above.

According to another aspect of the invention, compositions of matter are provided. The compositions include conjugates of a non-corneocyte, non-labeling agent and a linking molecule having a carboxamide, the linking molecule being a carboxamide bearing substrate of transglutaminase, wherein the agent is selected from the group consisting of a sunscreen agent, a bulking agent, a cosmetic, a hair conditioning agent including an antifoaming agent or an anti-static agent, a hair fixative agent, a moisturizing agent, including a humectant, and a depilatory agent (i.e., a hair removal agent), a vitamin, a film forming agent such as those used in hair fixatives or wound healing, an enzyme, a coloring agent, a pharmaceutical agent, a member of a ligand/receptor pair, a component of a high-affinity non-covalent coupling pair, a tissue sealant, an insecticide including louse repellents, an insect repellant, a bactericide, a fungicide, an anti-nerve gas or anti-neurotoxin agent and the like. The linking group is not native to the agent. Preferred linking molecules are as described above. In certain embodiments, particularly those involving the pharmaceutical agents, the bond between the agent and the linking group or molecule is a hydrolyzable bond or light cleavable bond. In certain important embodiments, the agent is a non-protein. In other important embodiments, the agent is an active agent. In other important embodiments, the agent, in its native form free of conjugation to the linking molecule, is not itself a substrate of transglutaminase.

Another composition is as described above, except that the linking molecule is one bearing multiple, spaced aliphatic amines. Such linking molecules carry at least three, preferably at least 4 and more preferably, at least 5 aliphatic amines that are substrates of transglutaminase, attached to the backbone of the linking molecule and separated from one another and spaced at discrete intervals. The linking molecule can be a polymer, and, in one important embodiment has at least 3, 4 or 5 contiguous lysines attached directly to one another by peptide bonds. In another embodiment the polymer is rich in aliphatic amnines.

According to other aspects of the invention, kits are provided. One such kit includes a package housing a first container containing a composition of matter as described above and a second container containing transglutaminase. The kit can further comprise a third container housed by the package, the third container containing a linking molecule that is a substrate of transglutaminase and that is covalently bondable, in the presence of transglutaminase, to the composition contained in the first container. The various containers also can contain vehicles, preservatives, buffers, calcium chelators and calcium (which is necessary for the activity of transglutaminase).

As mentioned above, the tissue can be pretreated to make it more receptive to the action of transglutaminase. In one embodiment described above, this is accomplished by attaching polymers rich in glutamine, lysine or both glutamine and lysine to the body tissue. In other embodiments, the tissue is treated to expose reactive glutamines and/or lysines by washing, chemical treatment, etc. Detergents and lipases can be used to remove fatty acids and oils. Roughening agents such as pumice, silica and sandpaper can be employed to remove dead tissue and other obstructions, and chemical agents such as sodium hydroxide can be used to expose reactive groups. Combinations of the foregoing are contemplated.

The invention also involves the use of transglutaminase to 'glue' two tissues together. Two tissues are held under force in contact with one another in the presence of an effective amount of transglutaminase, whereby the transglutaminase causes the cross-linking of the tissue to occur. Preferably, the surfaces of the tissues to be glued to one another are treated with a substrate of transglutaminase such as polymers rich in glutamine, lysine or both glutamine and lysine to create highly reactive surfaces in the presence of transglutaminase. These highly reactive surfaces are bonded to one another. Even more preferably, the surfaces of the tissue are first treated with a linking molecule to crosslink the linking molecule to the surfaces, then a linking molecule complementary to the first is applied to crosslink the linking molecules to one another and glue the tissue. The transglutaminase may be exogenously supplied. The tissue may be held together by any conventional means, such as sutures, tape, stapes and the like.

The agent also can be in a vehicle such as a microparticle, e.g. a microsphere or a nanosphere, the microsphere or nanosphere being rich in carboxamide or aliphatic amine substrates of transglutaminase, such as glutamines, lysines, or glutamines and lysines, whereby the microsphere or nanosphere can be attached to a body tissue.

According to still another aspect of the invention, a composition of matter is provided comprising a conjugate of a linking molecule that is a substrate of transglutaminase and an agent that is selected from the group consisting of a component of a ligand-receptor pair, a component of a high-affinity noncovalent binding pair and a microparticle. In this embodiment the linking molecule can be a carboxyamine substrate of transglutaminase or a alaphatic amine substrate of transglutaminase, such as lysine or known alaphatic amine substrates.

These and other aspects of the invention are described in further detail below.

DETAILED DESCRIPTION

Figure 1:
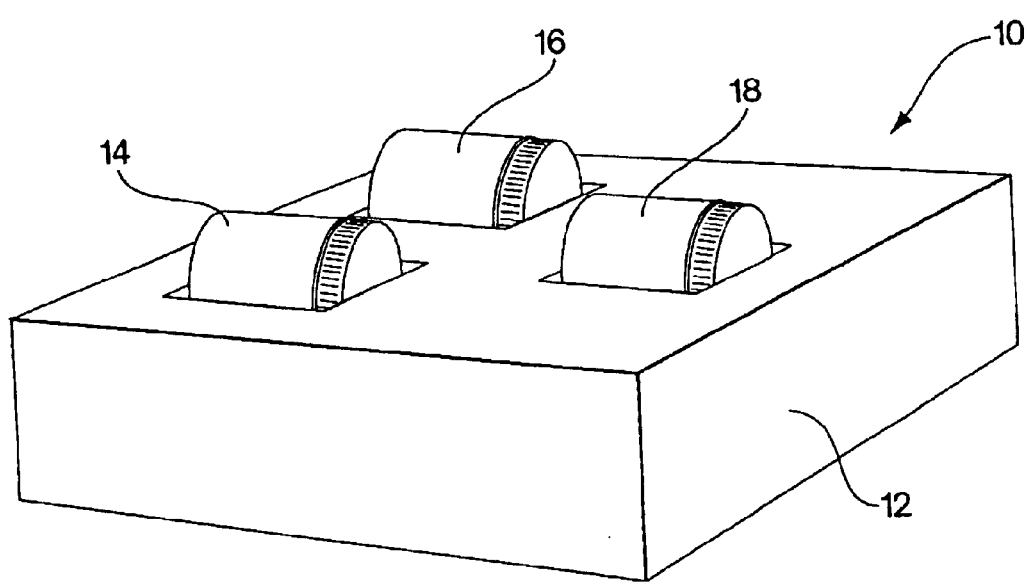
FIG. 1 depicts a kit according to the invention.

The invention is based in part on the discovery that polymers bearing multiple reactive (with transglutaminase) carboxamides or multiple reactive aliphatic amines are particularly useful linking molecules for attaching agents to proteinaceous material such as skin and hair. The closest prior art teaches away from using carboxamides and also from using polymers bearing multiple reactive aliphatic amines as defined herein, for such a purpose as described in greater detail below.

In general, the agents are chemical agents and include pharmaceutical agents, enzymes, cosmetics, bulking agents, hair conditioners and hair fixatives, anti-foaming agents, antistatic agents, moisturizing agents, including humectants, depilatories (i.e., hair removal agents), vitamins, film forming agents such as those used in hair fixatives or wound healing, anti-nerve gas or anti-neurotoxin agents, sunscreen agents, ligands of ligand-receptor pairs, receptors of ligand-receptor pairs, components of high affinity noncovalent bonding pairs, insecticides and repellants including louse repellents, bactericides, fungicides, tissue sealants, labels, structural proteins, chelating agents, microparticles and the like. Examples are listed below.

In certain embodiments the agent is a noncorneocyte, nonlabeling active agent. Thus, specifically excluded in these embodiments is corneocyte proteins. Corneocyte proteins have been shown in the prior art to be among the natural substrates of tnansglutaminase. In certain embodiments the agent also is a non-extracellular matrix protein agent. A non-extracellular matrix protein agent is one that is not an extracellular matrix protein. Fibronectin, an extracellular matrix protein, also has been shown in the prior art to be a substrate of transglutaminase. A nonlabeling active agent is one that is not simply a passive label with no function, when applied to a body tissue, other than being a label. Specifically excluded are labeled corneocyte proteins, labeled fibronectin, labeled extracellular matrix proteins, putrescine, dansylcadaverine, 5-(biotinanido)-pentylamine, fluoresceincadaverine and the like. Such compounds have been used in the prior art to detect on cells or cell extracts, substrates of transglutaminase.

By active agent it is meant that the agent, once coupled to a biological tissue in vivo or in vitro, has, maintains or can be released to have a desired activity such as a desired physiological activity or therapeutic activity. Examples of active agents are pharmaceutical agents, sunscreen agents, insecticides, bactericides, fungicides, etc. As used herein, an active agent is not a cosmetic agent and is not a labeling agent including diagnostic agents.

The agents are linked to proteinaceous material. When used in vivo, the agents are attached to a body tissue. Particularly important body tissues as sites of attachment are the integument (including specifically skin, nails, hair, mucous membranes and the surface of the eye), internal organs, internal tissue and wound beds. In in vitro applications, the tissue may be a body tissue, a tissue or cell isolate, isolated proteins, synthetic proteins, cell cultures and the like for use, for example, in assay systems according to the invention.

In certain embodiments, conjugates of agents and linking molecules are applied, for example, to body tissue and covalently linked to that tissue using transglutaminase.

As used herein, a conjugate means two entities stably bound to one another by any physiochemical means. It is important that the nature of the attachment be of such a nature that it does not impair substantially the effectiveness of the agent or the substrate binding ability of the linking molecule. Keeping these parameters in mind, any linkage known to those of ordinary skill in the art may be employed including covalent or noncovalent. Covalent linkage is preferred. Such means and methods of attachment are well known to those of ordinary skill in the art.

Typically the agents used according to the invention are not themselves, in their native form, substrates for transglutaminase. Such agents, however, can be modified according to the invention to render the agent a substrate of transglutaminase. This may be accomplished for example by adding a carboxamide side group(s) to an appropriate moiety of the agent (i.e. a "modified" agent) or by covalently coupling glutamine, lysine or both glutamine and lysine to the agent to form a conjugate that is a substrate of transglutaminase. The most preferred method is to couple polyglutamine, polylysine, a mixed polymer of glutamine and lysine, involucrin (a natural substrate of transglutaminase) or a fragment of involucrin to the agent to form an appropriate conjugate.

Preferred linking molecules are polymers bearing multiple reactive carboxamides and/or aliphatic amines that are substrates of transglutaminase. Carboxamides that are substrates of transglutaminase are well known and include glutamines. Aliphatic amines that are substrates of transglutaminase also are well known and are exemplified in, for example, U.S. Pat. No. 5,490,980, the disclosure of which is incorporated herein by reference. Unlike the '980 patent, however, which depicts single aliphatic amine moieties and plural such moieties as independent substituents in certain circumstances, the present invention involves in one aspect using a plurality of aliphatic amines spaced apart at discrete intervals, preferably along the length of a branched or unbranched polymer. It has been discovered, surprisingly, that the spacing of the reactive moieties can be important to achieving the results of the present invention.

One embodiment involves linking molecules that are polymers having multiple units, which units each bear an aliphatic amine substrate of transglutaminase. The polymer can be a homopolymer or a heteropolymer. As used herein in connection with linking molecules, a polyaliphatic amine substrate of transglutaminase is a linking molecule with at least three aliphatic amines spaced apart from one another at discrete intervals along the backbone of the linking molecule, separated by one or more backbone atoms. This is most easily envisioned, for example, with polymers rich in lysine, whereby discrete units of the polymer carry the aliphatic amine, each being separately a substrate for transglutamiinase. The linking molecule itself may be a polymer of contiguous lysines, preferably at least 3, at least 4 and at least 5 such contiguous lysines. Polymers of contiguous units, each carrying an aliphatic amine, are preferred.

The most preferred linking molecules are polymers rich in a carboxamide moiety or an aliphatic amine moiety, such as glutamine, lysine or both glutamine and lysine. A polymer rich in glutamine or lysine is a molecule wherein at least 20% of the units of the polymer carry a carboxamide, an aliphatic amine, or both, such as glutamine, lysine or glutamine and lysine, or wherein the molecule includes at least 3, preferably 4 and most preferably 5 separate and discretely spaced by a regular distance carboxamides or aliphatic amines, such as occurs with contiguous, linked glutamines or lysines. It should be understood, however, that a chain of as few as two glutamnines or lysines can be attached to or tethered to an agent to render the agent a substrate of transglutaminase.

As noted above, the invention in one aspect involves attaching active agents to proteinaceous materials using transglutaminase, wherein the native agent itself is a substrate of transglutaminase. Such agents typically will be polypeptides or proteins and most typically will contain reactive glutamines, lysines or both. To determine whether an agent itself is a substrate of transglutaminase (or a modified agent, or a covalent conjugate), a simple screening method is employed.

The screening method involves selecting a nonextracellular matrix protein, nonlabeling agent, preferably an active agent, that is a substrate for transglutaminase. The agent is applied, in an isolated form, to a proteinaceous material such as a body tissue, a body tissue isolate, or more preferably, a polymer rich in glutamine, a polymer rich in lysine or a polymer rich in glutamine and lysine. Then, transglutaminase is applied to the proteinaceous material in an amount sufficient and under appropriate conditions to cross-link the agent to the proteinaceous material if the agent is a substrate of transglutaminase. Then it is determined whether the agent covalently binds to the proteinaceous material. The amounts of materials and conditions employed for these assays are derivable from the examples below and, in general, can be derived by those of ordinary skill in the art without undue experimentation from, for example, the publication by Kahlem, et al., *Proc. Natl. Acad. Sci., USA*, Vol. 93, pp. 14580–14585, December, 1996.

In constructing conjugates, it may be desirable to vary not only the number of glutamines and/or lysines in the linking molecule, but it also may be desirable to tether the linking molecule to the active agent via a spacer. This can remove, for example, any problems that might arise from steric hindrance, wherein access by transglutaminase to the reactive moiety of the linking molecule is hindered. These spacers can be any of a variety of molecules, preferably nonactive, such as straight or even branched carbon chains of $C_1$–$C_{30}$, saturated or unsaturated, phospholipids, amino acids, and in particular glycine, and the like, naturally occurring or synthetic. Additional spacers include alkyl and alkenyl carbonates, carbamates, and carbamides. These are all related and may add polar functionality to the spacers such as the $C_1$–$C_{30}$ previously mentioned.

The conjugations or modifications described herein employ routine chemistry, which chemistry does not form a part of the invention and which chemistry is well known to those skilled in the art of chemistry. The use of protecting groups and known linkers such as mono and heterobifunctional linkers are well documented in the literature and will not be repeated here.

Attachment according to the invention thus need not be directed attachment. The components of the compositions of the invention may be provided with functionalized groups to facilitate their attachment and/or linker groups may be interposed between the components of these compositions to facilitate their attachment. In addition, the components of the compositions of the present invention may be synthesized in a single process, whereby the components could be regarded as one and the same entity. For example, a protein agent may be synthesized recombinantly to include a polyglutamine at one end for linking the polypeptide via transglutaminase.

Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Cross-linkers preferentially reactive with carbohydrates include azidobenzoyl hydrazine. Cross-linkers preferentially reactive with carboxyl groups include 4-[p-azidosalicylamido] butylamine. Heterobifunctional cross-linkers that react with amines and sulfhydryls include N-succinimidyl-3-[2-pyridyldithio]propionate, succinimidyl[4-iodoacetyl] aminobenzoate, succinimidyl 4-[N-maleimidomethyl] cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[[3-dimethylaminopropyl]-carbodiimide hydrochloride. Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio] propionyl hydrazide. The cross-linkers are bis-[$-4-azidosalicylamido)ethyl]disulfide and glutaraldehyde. Amine or thiol groups may be added at any nucleotide of a synthetic nucleic acid so as to provide a point of attachment for a bifunctional cross-linker molecule. The nucleic acid may be synthesized incorporating conjugation-competent reagents such as Uni-Link AminoModifier, 3'-DMT-C6-Amine-ON CPG, AminoModifier II, N-TFA-C6-AminoModifier, C6-ThiolModifier, C6-Disulfide Phosphoramidite and C6-Disulfide CPG (Clontech, Palo Alto, Calif.).

In constructing conjugates, it also may be desirable to attach the agent to the linking molecule by a bond that cleaves under normal physiological conditions or that can be caused to cleave specifically upon application of a stimulus such as light, whereby the agent can be released. In certain instances, the agent may be inactive in its conjugated form and activated only when released. In other instances, the agent would be released to exert an activity remote from its point of attachment to the body tissue. In still other instances, the agent would be released in a sustained fashion, to prolong the release of the agent versus an agent applied to tissue but not covalently coupled to the tissue. Readily cleavable bonds include readily hydrolyzable bonds, for example, ester bonds, amide bonds and Schiff's base-type bonds. Bonds which are cleavable by light are well known.

Noncovalent methods of conjugation may also be used. Noncovalent conjugation includes hydrophobic interactions, ionic interactions, high affinity interactions such as biotin-avidin and biotin-streptavidin complexation and other affinity interactions. In one embodiment, a molecule such as avidin is attached to a linking molecule such as polyglutamine. This conjugate, once attached to tissue according to the invention, then becomes a universal linking moiety for any agent attached to a biotin molecule.

As mentioned above, the linking molecules may be part of a microparticle such as a microsphere or a nanosphere and the agent may be contained in the microparticle, either physically entrapped therein, covalently bonded thereto or otherwise physiochemically attached to the microparticle. In preferred embodiments, the microspheres or nanospheres carry, at least on their surface, polymers rich in glutamine, lysine, or both glutamine and lysine. The methods for manufacturing mnicroparticles according to the prior art are well documented and do not form a basis for the present invention. The present invention differs from those of the prior art only in that either the polymers of the mnicroparticle structure themselves contain or are derivatized to contain glutamines and/or lysines, or polymers of glutamine, lysine or glutamine and lysine are included within the mixture of polymers forming the matrix, whereby such polymers are entrapped throughout and at the surface of the microparticles. Examples of microspheres and nanospheres and their method of manufacture may be found in U.S. Pat. No. 5,075,019, PCT WO95/24929, PCT WO94/23739 and PCT/US96/11990, the disclosures of which are incorporated herein by reference.

Agents in an isolated form are sometimes applied according to the invention. Isolated as used herein will depend upon the agent employed. In general, isolated as used herein means that the material is essentially free of other substances to an extent practical and appropriate for the intended use of the material. In the case of pharmaceuticals and cosmetics, the materials are likely to be substantially pure. In the case of proteins, the proteins are sufficiently pure and sufficiently free from other biological constituents of the host cells from which the proteins are derived so as to be useful in the methods according to the invention. Typically, such agents will be at least 95% or more pure.

Agents are sometimes described as native agents herein. A native agent is one as it occurs in nature (isolated or synthesized to duplicate a naturally occurring molecule), without modification or conjugation as described herein.

As mentioned above, the body tissue, to which the agents and conjugates of the invention are to be applied, may be pretreated to facilitate the reaction with transglutaminase. Such treatments include washings, abrasive treatments including physical agents such as pumice, silica and oatmeal, enzymes such as papain, bromelins and the like and chemical agents such as alpha hydroxy acids and glycolic acids. The main object is to treat the body tissue so as to expose or create reactive glutamines and/or lysines. Likewise, as mentioned above, the body tissue may be pretreated by putting down a layer or reactive groups, such as by applying to the body tissue polymers rich in lysine, glutamine or both lysine and glutamine. These materials may be attached to the body tissue by any conventional means, but, according to the invention, also may be attached using transglutaminase.

It should be noted that glutamnine, lysine, and polymers of glutamine and lysine are described above. As used herein, such terms embrace nonpeptidic multimers of glutamine and lysine whereby amino acid analogs are used to replace these amino acids in the polyglutamine or polylysine substrates. Some well known classes of peptide mimetics and pseudopeptides are: azabicycloalkane amino acids; thiazabicycloalkane amino acids; oxazabicycloalkane amino acids; diazabicycloalkane amino acids. D-amino acids are an important embodiment.

The transglutaminase may be exogenously added transglutaminase or may be endogenous transglutaminase present at the tissue.

In one embodiment transglutaminase is used to glue two tissues to one another. This can be accomplished in a variety of ways. Transglutaminase, a substrate of transglutaminase, or both can be supplied to the surfaces of two tissues which then are held in contact with one another for a period of time sufficient to permit transglutaminase to crosslink the tissues to one another. In one circumstance, exogenously supplied transglutaminase is applied to the surfaces of the tissues to crosslink substrates of transglutaminase to one another, which substrates are present and are endogenous on the surfaces of the tissue. In another circumstance, exogenously supplied substrates of transglutaminase are applied to the surfaces of the tissues and are acted upon by endogenous transglutaminase to crosslink the tissue surfaces to one another. In another circumstance both transglutaminase and substrate of transglutaminase are applied to the surfaces of the tissue to crosslink the surfaces to one another. In this situation, a single substrate such as polyglutamine could be applied, one end attaching to one surface and the other end attaching to the opposing surface of the tissues to be crosslinked to one another. Alternatively, a first substrate (a linking molecule such as polyglutamine) could be applied to create first reactive surfaces and a second substrate (a complementary linking molecule such as polylysine) could be applied to crosslink the primary linking molecules on opposing surfaces to one another.

The invention also involves kits. Referring to FIG. 1, the kit is a package 10 comprising a housing 12 holding a first container 14, a second container 16 and a third container 18. The first container can contain any of the agents or conjugates that are substrates of transglutaminase, as described above. The second container can contain transglutaminase. The third container can contain, for example, a linking molecule for preparing the surface of the body tissue for application of the agents and conjugates of the invention. The transglutaminase preferably is stored in the presence of a chelating agent such as EDTA, and either one of the first or third containers contains calcium for activating the transglutaminase when applied to the tissue. The various containers may also contain preservatives, buffers, vehicles, and the like, as is conventional. The package also may house instructions for using the materials according to the invention.

The conjugates and agents of the invention are applied in effective amounts. An effective amount, in general, means that amount necessary to achieve the purpose for which the agent is applied. If the agent is a pharmaceutical agent, then the amount is that amount necessary to delay the onset of, slow the progression of, halt altogether the onset or progression of or diagnose a particular condition being treated. In the case of a cosmetic agent, the effective amount will be that amount necessary to achieve the desired cosmetic result. In the case of a sunscreen agent, an effective amount will be that amount necessary to achieve suitable protection from the sun as is conventional. Effective amounts will, of course, depend on the particular condition being treated, severity of the condition, the needs of the patient, individual patient parameters including age, physical condition, size and weight, concurrent treatment, frequency of treatment and mode of treatment. These factors are well-known to those of ordinary skill in the art and can be addressed with no more than routine experimentation. The mode of delivery typically will be topical. Other modes of delivery are, nonetheless, appropriate depending on the condition being treated. Aerosols are an example of an appropriate mode of delivery.

The agent may be a sunscreen agent. Examples of sunscreen agents include: p-aminobenzoate analogs such as 2-ethylhexyl-4-dimethylaminobenzoate (Padimate O); p-methoxy-2-ethyl-hexyl-cinnamate (Parsol 1789); oxybenzone (benzophenone-3); ethylhexylsalicylate; diphenylacrylate polyisobutylene; alkyl-$\beta,\beta$-diphenylacrylate and $\alpha$-cyano-$\beta,\beta$-diphenylacrylate; 1-(4-aminophenyl)-2-morpholinylethanone; (1-(4-methoxylphenyl)-3-(4-tert-butyl-phenyl))-propan-1-3-dione; methyl anthranilate; octocrylene; Tretinoin"-hydroxyacid; diphenylacrylate polyisobutylene; 1-(4-aminophenyl)-2-morpholinylethanone; diphenylacrylate polyisobutylene; digalloyl trioleate; glyceryl p-aminobenzoate; 4-(omega-dialkylaminoalkoxy)phenylmethylene)-1,3,3-trimethyl-2-oxabicyclo(2.2.2)octan-6-ones; 5-(arylmethylene)-1,3,3-trimethyl-2-oxabicyclo(2.2.2)octan-6-ones; melanin.

Further examples of sunscreen agents include: 3-benzylidene camphor; 4-methylbenzylidene camphor; allantoin PABA benzalphthalide; benzophenone; benzophenone-1; benzophenone-10; benzophenone-11; benzophenone-12; benzophenone-2; benzophenone-3; benzophenone4; benzophenone-5; benzophenone-6; benzophenone-7; benzophenone-8; benzophenone-9; benzyl salicylate; benzylidene camphor sulfonic acid; bornelone; bumetrizole; butyl methoxydibenzoylmethane; camphor benzalkonium methosulfate; cinoxate; DEA-methoxycinnamate; diisopropyl methyl cinnamate; dimethyl PABA ethyl cetearyldimonium tosylate; drometrizole; ethyl cinnamate; ethyl dihydroxypropyl PABA; ethyl diisopropylcinnamate; ethyl methoxycinnamate; ethyl urocanate; etocrylene; lyceryl octanoate dimethoxycinnamate; glyceryl PABA; glycol salicylate; homosalate; soamyl p-methoxycinnamate; isopropyl dibenzoylmethane; isopropyl methoxycinnamate; isopropylbenzyl salicylate; menthyl anthranilate; menthyl salicylate; n-ethyl-3-nitro PABA; octocrylene; octrizole; octyl dimethyl PABA; octyl methoxycinnamate; octyl salicylate; octyl triazone; PABA; PEG-25 PABA; phenylbenzimidazole sulfonic acid; polyacrylamidomethyl benzylidene camphor; potassium methoxycinnamate; potassiun phenylbenzimidazole sulfonate; red petrolatum; sodium phenylbenzimidazole sulfonate; TEA-phenylbenzimidazole sulfonate; TEA-salicylate; terephthalylidenc dicamphor sulfonic acid; tripaba panthenol; urocanic acid.

Further examples of compounds which are suitable sunscreen agents include: derivatives of para-amine benzoic acid (PABA); salicylates; cinnamates; benzophenones; camphors; 4-aminobenzoic acid; N,N,N-trimethyl-4-(2-oxoborn-3-yldenemethyl)anilinium methyl sulphate; homosalate (INN); oxybenzone (INN); 2-phenylbenzimidazole-5-sulphonic acid and its potassium, sodium and triethanolamine salts; 3,3'-(1,4-phenylenedimethylene) bis (7,7-dimethyl-2-oxobicyclo-[2.2.1]hept-1-ylmethanesulphonic acid) and its salts; 1-(4-tertbutylphenyl)-3-(4-(methoxyphenyl)propane-1,3-dione; alpha-(2-oxoborn-3-ylidene)toluene-4-sulphonic acid and its salts; 2-cyano-3,3-diphenyl acrylic acid, 2-ethylhexyl ester (octrocrylene); polymer of N-{(2 and 4)-[(2-oxoborn-3-ylidene)methyl]benzyl}acrylamide; octyl methoxycinnamate; ethoxylated ethyl-4-aminobenzoate (PEG-25 PABA); isopentyl4 methoxycinnamate (isoamyl p-methoxycinnamate); 2,4,6-trianilino-(p-carbo-2ethylhexyl-1-'oxy)-1,3,5-triazine (octyl triazone); phenol 2-(2h-benzotriazol-2-yl)-4-methyl-6-(2-methyl-3-(1,3.3,3-tetramethyl-1-(trimethylsilyl)oxy)-disiloxanyl)propyl) (drometrizole trisiloxane); 3-(4'-methylbenzylidene)-d-1 camphor (4-methylbenzylidene camphor); 3-benzylidene camphor (3-benzylidene camphor); 2-ethylhexyl salicyclate (octyl-salicylate); 2-ethylhexyl-4-dimethylaminobenzoate; 2-hydroxy-4-methoxybenzo-phenone-5-sulphonic acid and sodium salt (sulisobenzone and sulisobenzone sodium); 4-isopropylbenzyl salicylate; cinnamic derivatives, such as, for example, 2-ethylhexyl p-methoxycinnamate; salicylic derivatives, such as, for example, 2-ethylhexyl salicylate; camphor derivatives, such as, for example, (4-methylbenzylidene)carmphor or benzene-1,4-di(3-methylidene-10-camphorsulfonic) acid; benzimidazole derivatives, such as 2-phenylbenzimidazole-5-sulfonic acid; benzophenone derivatives, such as 2-hydroxy-4-methoxybenzophenone; dibenzoylmethane derivatives, such as 4-tert-butyl-4'-methoxydibenzoylmethane, or β,β-diphenylacrylate derivatives, such as 2-ethylhexyl α-cyano-β,β-diphenylacrylate; p-aminobenzoic acid, cinoxate, diethanolamine, p-methoxycinnamate, digalloyl trioleate, dioxybenzone, ethyl 4->bis>hydroxypropyl!aminobenzoate, 2-ethylhexyl 2-cyano-3,3-diphenylacrylate, ethylhexyl p-methoxycinnamate, 2-ethyhexyl salicylate, glyceryl aminobenzoate, homosalate (3,3,5-trimethylcyclohexylsalicylate), lawsone (2-hydroxy-1,4-naphthoquinone) with or without dihydroxyacetone, methyl anthranilate, oxybenzone, Padimate A, Padimate 0, 2-phenylbenzimidazole-5-sulfonic acid, triethanolamine salicylate, red petrolatum, and suisobenzone; titanium dioxide or zinc oxide.

The agent may also be a cosmetic agent. Examples of cosmetic components include: Vitamin C; Alpha-tocopherol (Vitamin E analog); Ammonium lauryl Sulfate; Cocamidopropyl Betaine; Lauramide DEA; Cocamide DEA; Methyl paraben; Propyl paraben; Butyl paraben; Salicylic acid; Propylene glycol; EDTA; BHT; BHA; TBHQ; DMDM hydantoin; Imidazolidinyl urea; Potassium sorbate; Sodium Benzoate; phenoxyethanol; Polysorbate 20 and 80; Sodium laurylether sulfate; Oleyl betaine; Tego betaine; Sorbitol; Glycerin monolaurate; Glycerol stearate.

The agent may also be a coloring agent for coloring hair or skin. A coloring agent is one which is able to change the color of skin, hair or nails. Color change may be effected through for example, a lightening or darkening of skin, hair or nails. Examples of coloring agents for hair include: 1,2,4-benzenetriacetate; 1,2,4-trihydroxybenzene; 1,3-bis-(2,4-diaminophenoxy)propane; 1,5-naphthalenediol; 1-naphthol; 2,3-naphthalenediol; 2,4-diamino-5-methylphenetol HCl; 2,4-diamino-5-methylphenoxyethanol HCl; 2,4-diaminodiphenylamine; 2,4-diaminophenol; 2,4-diaminophenol HCl; 2,4-diamninophenoxyethanol HCl; 2,6-bis(2-hydroxyethoxy)-3,5-pyridinediamine HCl; 2,6-diaminopyridine; 2,6-dimethoxy-3,5-pyridinediamine HCl; 2,7-naphthalenediol; 2-amino-3-hydroxypyridine; 2-amino-3-nitrophenol; 2-amino-4-hydroxyethylaminoanisole; 2-amino-4-hydroxyethylaminoanisole sulfate; 2-amino-6-chloro-4-nitrophenol; 2-aminomethyl-p-aminophenol HCl; 2-chloro-5-nitro-n-hydroxyethyl p-phenylenediamine; 2-chloro-6-ethylamino-4-nitrophenol; 2-chloro-p-phenylenediamine; 2-chloro-p-phenylenediamine sulfate; 2-hydroxyethyl picramic acid; 2-hydroxyethylamino-5-nitroanisole; 2-methoxymethyl-p-aminophenol HCl; 2-methyl-5-hydroxyethylaminophenol; 2-methylresorcinol; 2-nitro-5-glyceryl methylaniline; 2-nitro-n-hydroxyethyl-p-anisidine; 2-nitro-p-phenylenediamine; 3,4-diaminobenzoic acid; 3,4-methylenedioxyaniline; 3,4-methylenedioxyphenol; 3-methylamino-4-nitrophenoxyethanol; 3-nitro-4-aminophenoxyethanol; 3-nitro-p-cresol; 3-nitro-p-hydroxyethylaminophenol; 4,4-diaminodiphenylamine; 4,5-diaamino-1-methylpyrazole HCl; 4,6-bis(2-hydroxyethoxy)-m-phenylenediamine HCl; 4-amino-2-hydroxytoluene; 4-amino-2-nitrodiphenylamine-2-carboxylic acid; 4-amino-3-nitrophenol; 4-amino-m-cresol; 4-chlororesorcinol; 4-hydroxyindole; 4-hydroxypropylamino-3-nitrophenol; 4-methoxytoluene-2, 5-diamine HCl; 4-nitro-m-phenylenediamine; 4-nitro-o-phenylenediamine; 4-nitro-o-phenylenediamine HCl; 4-nitrophenyl aminoethylurea; 5-amino-2,6-dimethoxy-3-hydroxypyridine; 5-amino-6-chloro-o-cresol; 6-amino-m-cresol; 6-amino-o-cresol; 6-hydroxyindole; 6-methoxy-2,3- pyridinediamine HCl; 6-nitro-2,5-pyridinediamine; 6-nitro-o-toluidine; acacia catechu; acid black 1; acid black 52; acid blue 1; acid blue 3; acid blue 62; acid blue 74; acid blue 9; acid brown 13; acid green 1; acid green 25; acid green 50; acid orange 24; acid orange 3; acid orange 6; acid orange 7; acid red 14; acid red 18; acid red 27; acid red 33; acid red 35; acid red 51; acid red 52; acid red 73; acid red 87; acid red 92; acid red 95; acid violet 43; acid violet 9; acid yellow 1; acid yellow 23; acid yellow 3; acid yellow 73 sodium salt; basic blue 26; basic blue 41; basic blue 6; basic blue 7; basic blue 9; basic blue 99; basic brown 16; basic brown 17; basic brown 4; basic green 1; basic red 2; basic red 22; basic red 76; basic violet 14; basic yellow 11; basic yellow 57; brilliant black 1; chromium hydroxide green; chromium oxide greens; curry red; dihydroxyindole; direct black 51; direct blue 86; direct red 23; direct red 80; direct red 81; direct violet 48; direct yellow 12; disperse black 9; disperse blue 1; disperse blue 3; disperse blue 7; disperse brown 1; disperse orange 3; disperse red 11; disperse red 15; disperse red 17; disperse violet 1; disperse violet 4; fast green FCF; HC blue No. 10; HC blue No. 11; HC blue No. 12; HC blue No. 2; HC blue No. 4; HC blue No. 5; HC blue No. 6; HC blue No. 7; HC blue No. 8; HC blue No. 9; HC brown No. 1; HC brown No. 2; HC green No. 1; HC orange No. 1; HC orange No. 2; HC orange No. 3; HC red No. 1; HC red No. 10; HC red No. 11; HC red No. 13; HC red No. 3; HC red No. 7; HC red No. 8; HC red No. 9; HC violet No. 1; HC violet No. 2; HC yellow No. 10; HC yellow No. 11; HC yellow No. 12; HC yellow No. 13; HC yellow No. 2; HC yellow No. 4; HC yellow No. 5; HC yellow No. 6; HC yellow No. 7; HC yellow No. 8; HC yellow No. 9; henna; hydroquinone; hydroxyanthraquinoneaminopropyl methyl morpholinium methosulfate; hydroxybenzomorpholine; hydroxyethyl-2,6-dinitro-p-anisidine; hydroxyethyl-2-nitro-p-toluidine; hydroxyethyl-3,4-methylenedioxyaniline HCl; hydroxyethyl-p-phenylenediamine sulfate; hydroxyethylaminomethyl-p-aminophenol HCl; hydroxypropyl bis(n-hydroxyethyl-p-phenylenedianine) HCl; lawsone; lead acetate; m-aminophenol; m-aminophenol HCl; m-aminophenol sulfate; m-phenylenediamine; m-phenylenediamine sulfate; N,N-bis(2-hydroxyethyl)-p-phenylenediamine sulfate; N,N-diethyl-m-aminophenol; N,N-diethyl-m-aminophenol sulfate; N,N-dimethyl 2,6-pyridinediamine HCl; N,N-dimethyl-p-phenylenediamine; N,N-dimethyl-p-phenylenediamine sulfate; N,N-bis(2-hydroxyethyl)-2-nitro-p-phenylenediamine; N,N-dimethyl-n-hydroxyethyl-3-nitro-p-phenylendiamine; n-ethyl-3-nitro PABA; n-methoxyethyl-p-phenylenediamine HCl; n-methyl-3-nitro-p-phenylenediamine; n-phenyl-p-phenylenediamine; n-phenyl-p-phenylenediamine HCl; n-phenyl-p-phenylenediamine sulfate; o-aminophenol; p-aminophenol; p-aminophenol HCl; p-aminophenol sulfate; p-methylaminophenol; p-methylaminophenol sulfate; p-phenylenediamine; p-phenylenediamine HCl; p-phenylenediamine sulfate; phenyl methyl pyrazolone; phloroglucinol; picramic acid; pigment blue 15; pigment green 7; pigment red 112; pigment red 172 aluminum lake; pigment red 4; pigment red 48; pigment red 5; pigment red 57; pigment red 57:1; pigment red 63:1; pigment red 64:1; pigment red 83; pigment red 90:1 aluminum lake; pigment violet 19; pigment violet 23; pigment yellow 12; pigment yellow 13; pigment yellow 73; ponceau sx; resorcinol; silver nitrate; sodium picramate; solvent black 3; solvent green 3; solvent green 7; solvent orange 1; solvent red 1; solvent red 23; solvent red 3; solvent red 43; solvent red 48; solvent red 72; solvent red 73; solvent violet 13; solvent yellow 29; solvent yellow 33; solvent yellow 44; sunset yellow; thymol; toluene-2,5-diamine; toluene-2,5-diamine sulfate; toluene-3,4-diamine; ultramarines; VAT red 1; m- and p-phenylenediamines, their N-substituted derivatives and their salts; N-substituted derivatives of o-phenylenediamines; methylphenylenediamines, their N-substituted derivatives and their salts; diaminophenols; hydroquinone; alpha-naphthol; lead acetate.

Coloring agents also include bleaching agents such as ammonium persulfate; hydroquinone and strontium dioxide.

Other examples of coloring agents are cosmetic colorants which include: acid red 195; aluminum stearate; anthocyanins; beta vulgaris; beta vulgaris; bismuth oxychloride; bromocresol green; bromothymol blue; calcium stearate; capsanthin/capsorubin caramel; CI 10006; CI 10020; CI 10316; CI 10316; CI 11680; CI 11710; CI 11725; CI 11920; CI 12010; CI 12085; CI 12120; CI 12150; CI 12370; CI 12420; CI 12480; CI 12490; CI 12700; CI 13015; CI 14270; CI 14700; CI 14700; CI 14720; CI 14815; CI 15510; CI 15510; CI 15525; CI 15580; CI 15620; CI 15630; CI 15800; CI 15850; CI 15850; CI 15850; CI 15850; CI 15850; CI 15850; CI 15850; CI 15850; CI 15850; CI 15850; CI 15850; CI 15865; CI 15865; CI 15880; CI 15980; CI 15985; CI 15985; CI 16035; CI 16185; CI 16185; CI 16230; CI 16255; CI 16290; CI 17200; CI 17200; CI 18050; CI 18130; CI 18690; CI 18736; CI 18820; CI 18965; CI 19140; CI 19140; CI 19140; CI 20040; CI 20170; CI 20470; CI 21100; CI 21108; CI 21230; CI 24790; CI 26100; CI 27290; CI 27755; CI 28440; CI 40215; CI 40800; CI 40820; CI 40825; CI 40850; CI 42045; CI 42051; CI 42053; CI 42080; CI 42090; CI 42090; CI 42090; CI 42100; CI 42170; CI 42510; CI 42520; CI 42735; CI 44045; CI 44090; CI 45100; CI 45190; CI 45220; CI 45350; CI 45350; CI 45370; CI 45370; CI 45370; CI 45370; CI 45380; CI 45380; CI 45380; CI 45380; CI 45396; CI 45405; CI 45410; CI 45410; CI 45410; CI 45410; CI 45410; CI 45410; CI 45410; CI 45425; CI 45425; CI 45425; CI 45430; CI 45430; CI 47000; CI 47005; CI 47005; CI 50325; CI 50420; CI 51319; CI 58000; CI 59040; CI 60724; CI 60725; CI 60730; CI 61565; CI 61570; CI 61585; CI 62045; CI 69800; CI 69825; CI 71105; CI 73000; CI 73015; CI 73015; CI 73360; CI 73385; CI 73900; CI 73915; CI 74100; CI 74160; CI 74180; CI 74260; CI 75100; CI 75120; CI 75125; CI 75130; CI 75135; CI 75170; CI 75300; CI 75470; CI 75810; CI 75810; CI 75810; CI 75810; CI 77000; CI 77002; CI 77004; CI 77004; CI 77004; CI 77007; CI 77015; CI 77120; CI 77163; CI 77220; CI 77231; CI 77266; CI 77267; CI 77268:1; CI 77288; CI 77289; CI 77346; CI 77400; CI 77480; CI 77489; CI 77491; CI 77492; CI 77499; CI 77510; CI 77713; CI 77742; CI 77745; CI 77820; CI 77891; CI 77947; lactoflavin; magnesium stearate; riboflavin and zinc stearate.

The agent may also be a moisturizing agent. A moisturizing agent is an agent which softens and smoothens skin and in some instances hair. Some moisturizing agents are also humectants in that they are able to hold and retain moisture. Emollient agents can be moisturing agents. Moisturizing agents can be used soften skin prior to abrasive events such as shaving. In these latter embodiments, the composition of the invention comprising a moisturizing agent can be supplied in a shaving gel or creme. Examples of moisturizing agents include: proteoglycans and glycosaminoglycans including hyaluronic acid, crosslinked hyaluronic acid, derivatized hyaluronic acid, chondroitin sulfate; mono- and poly-hydroxyl containing chemicals such as glycerin, sorbitol; pyrrolidine carboxylic acid; proteins such as hydrolyzed animal and vegetable protein, collagens, derivatized collagens, elastins; allantoin; polymer skin conditioning agents; polyols such as glycerol; chitosans; derivatized chitosans; and polyglutamine.

Other examples of moisturizing agents include D,L-panthenol, D-panthenol, vitamin A palmitate, vitamin E acetate, methylsilanetriol mannuronate, natural oils such as tallow oil, macadamia nut oil, borage oil, evening primrose oil, kukui nut oil, rice bran oil, tea tree oil, a medium chain fatty acid ester of glycerol, such as glycerol triheptanoate, glyceryl trioctanoate, glycerol trioctanoate, mineral water, silicones, silicone derivatives; allantoin; dipotassium glycyrrhizinate; stearyl glycyrrhizinate; squalane NF; squalane EX; cetyl ester wax; orange roughy oil; hydrogenated phospholipids; hydrocarbon oils and waxes, such as mineral oil, polyethylene and paraffin; triglyceride esters, such as olive oil, avocado oil, and squalene; lanolin and derivatives; ether-esters, such as fatty acid esters of ethoxylated fatty alcohols; and fatty acids having 10 to 20 carbon atoms, such as lauric, myristic, oleyl, and stearate.

Emollients useful in the invention as moisturizers include: acetamidoethoxybutyl trimonium chloride; acetyl trioctyl citrate; acetylated castor oil; acetylated cetyl hydroxyprolinate; acetylated glycol stearate; acetylated hydrogenated cottonseed glyceride; acetylated hydrogenated lanolin; acetylated hydrogenated lard glyceride; acetylated hydrogenated tallow glyceride; acetylated hydrogenated tallow glycerides; acetylated hydrogenated vegetable glyceride; acetylated lanolin; acetylated lanolin alcohol; acetylated lanolin ricinoleate; acetylated lard glyceride; acetylated palm kernel glycerides; acetylated sucrose distearate; adeps bovis; adeps suillus; aleurites moluccana; allyl caproate; almond oil peg-6 esters; aloe barbadensis; althea officinalis; aluminum hydroxide; aluminum stearates; aluminum tristearate; amodimethicone/dimethicone copolyol; amp-isostearoyl hydrolyzed collagen; anacardium occidentale; apple peel wax; apricot kernel oil PEG-6 esters; arachidonic acid; arachidyl alcohol; arachidyl behenate; arachidyl glycol isostearate; arachidyl propionate; arachis hypogaea; arctium lappa; avena sativa; avocado oil PEG-11 esters; bassia latifolia; batyl alcohol; batyl isostearate; batyl stearate; bayberry wax; behenoxy dimethicone; behenyl/isostearyl beeswax; behenyl alcohol; behenyl behenate; behenyl erucate; behenyl isostearate; benzyl laurate; bis-diglyceryl/caprylate/caprate/isostearate/hydroxystearate adipate; bis-diglyceryl caprylate/caprate/isostearate/stearate/hydroxystearate adipate; bisphenylhexamethicone; borago officinalis; borago officinalis; brassica botrytis; brassica oleifera; brassica oleifera; brevoortia; bubulum; butyl acetyl ricinoleate; butyl isostearate; butyl myristate; butyl oleate; butyl stearate; butylene glycol dicaprylate/dicaprate; butylene glycol montanate; butyloctyl beeswax; butyloctyl oleate; butyrospermwn parkii; butyroyl trihexyl citrate; butyrum; buxus chinensis; C10–18 triglycerides; C11–15 pareth-12 stearate; C11–15 pareth-3 oleate; C11–15 pareth-3 stearate; C12–13 alcohols; C12–13 alkyl lactate; C12–13 alkyl octanoate; C12–15 alcohols; C12–15 alkyl benzoate; C12–15 alkyl lactate; C12–15 alkyl octanoate; C12–15 pareth-12 oleate; C12–16 alcohols; C12–18 acid triglyceride; C13–14 isoparaffin; C15–18 glycol; C18–28 alkyl acetate; C18–36 acid glycol ester; C18–36 acid triglyceride; C18–38 alkyl beeswax; C18–70 isoparaffin; C20–40 alkyl behenate; C20–40 isoparaffin; C24–28 alkyl methicone; C30–45 alkyl methicone; C9–11 alcohols; Calendula officinalis; camelina sativa; cananga odorata; candelilla cera; canola; capryl glycol; caprylic/capric/diglyceryl succinate; caprylic/capric/lauric triglyceride; caprylic/capric/linoleic triglyceride; caprylic/capric/myristic/stearic triglyceride; caprylic/capric/stearic triglyceride; caprylic/capric glycerides; caprylic/capric triglyceride; carnauba; carthamus tinctorius; carthamus tinctorius; cera alba; ceratonia siliqua; ceratonia siliqua; cetearyl alcohol; cetearyl behenate; cetearyl candelillate; cetearyl isononanoate; cetearyl octanoate; cetearyl palmitate; cetyl acetate; cetyl acetyl ricinoleate; cetyl alcohol; cetyl C12–15-pareth-9 carboxylate; cetyl caprylate; cetyl dimethicone; cetyl esters; cetyl glycol; cetyl glycol isostearate; cetyl isononanoate; cetyl lactate; cetyl laurate; cetyl myristate; cetyl octanoate; cetyl oleate; cetyl palmitate; cetyl ricinoleate; cetyl stearate; cetylarachidol; chamomilla recutita; chimyl isostearate; cholesterol; cholesteryl hydroxystearate; cholesteryl isostearate; cholesteryl macadamiate; cholesteryl nonanoate; cholesteryl stearate; cistus ladaniferus; cocaminobutyric acid; cocaminopropionic acid; coco-caprylate/caprate; coco-rapeseedate; cocoglycerides; coconut acid; coconut alcohol; cocos nucifera; cocoyl glutamic acid; coenzyme a; corn acid; corn oil PEG-6 esters; corn oil PEG-8 esters; corylus americana; corylus avellana; cottonseed acid; cottonseed glyceride; cucumis sativus; cucurbita pepo; curcuma zedoaria; cyatheaceae; cyclomethicone; dalea spinosa; daucus carota; decyl alcohol; decyl isostearate; decyl myristate; decyl oleate; decyl succinate; decyltetradecanol; di-C12–13 alkyl malate; di-C12–13 alkyl tartrate; di-C12–15 alkyl adipate; dibutyl adipate; dibutyl sebacate; dicapryl adipate; dicaprylyl maleate; dicetyl adipate; dicocamine; dicocodimethylamine dilinoleate; dicocoyl pentaerythrityl distearyl citrate; didecene; diethyl palmitoyl aspartate; diethyl sebacate; diethyl succinate; diethylene glycol dibenzoate; diethylene glycol diisononanoate; diethylene glycol dioctanoate; diethylene glycol dioctanoate/diisononanoate; dihexyl adipate; dihydroabietyl behenate; dihydrocholesterol; dihydrocholesteryl octyldecanoate; dihydrogenated tallow phthalate; dihydrophytosteryl octyldecanoate; dihydroxycthyl soyamine dioleate; dihydroxyethylamino hydroxypropyl oleate; diisobutyl adipate; diisocetyl adipate; diisodecyl adipate; diisononyl adipate; diisopropyl adipate; diisopropyl dimer dilinoleate; diisopropyl sebacate; diisostearyl adipate; diisostearyl dimer dilinoleate; diisostearyl fumarate; diisostearyl glutarate; diisostearyl malate; dilaureth-7 citrate; dilauryl citrate; dilinoleic acid; dimethicone; dimethicone copolyol; imethicone copolyol almondate; dimethicone copolyol avocadoate; dimethicone copolyol beeswax; dimethicone copolyol cocoa butterate; dimethicone copolyol olivate; dimethicone copolyol phthalate; dimethicone copolyol shea butterate; dimethicone propylethylenediamine behenate; dimethiconol; dimethiconol hydroxystearate; dimethiconol isostearate; dimethiconol stearate; dimethyl adipate; dimethyl lauramine dimer dilinoleate; dimethyl lauramine isostearate; dimethyl maleate; dimethyl succinate; dimethyl tallowamine; dioctyl adipate; dioctyl dimer dilinoleate; dioctyl malate; dioctyl sebacate; dioctyl succinate; dioctylcyclohexane; dioctyldodecyl dimer dilinoleate; dipentaerythrityl hexaheptanoate/hexacaprylate/hexacaprate dipropyl adipate; dipropylene glycol dibenzoate; distearyldimethylamine dilinoleate; ditridecyl adipate; ditridecyl dimer dilinoleate; dodecyltetradecanol; dromiceius; elaeis guineensis; elaeis guineensis; epoxidized soybean oil; erucyl arachidate; erucyl erucate; erucyl oleate; ethiodized oil; ethyl arachidonate; ethyl avocadate; ethyl ester of hydrolyzed animal protein; ethyl isostearate; ethyl laurate; ethyl linoleate; ethyl linolenate; ethyl minkate; ethyl morrhuate; ethyl myristate; ethyl oleate; ethyl olivate; ethyl palmitate; ethyl pelargonate; ethyl persate; ethyl stearate; fish glycerides; gadi iecur; glycereth-7 triacetate; glycerin/oxybutylene copolymer stearyl ether; glyceryl/sorbitol oleate/hydroxystearate; glyceryl abietate; glyceryl adipate; glyceryl arachidate; glyceryl arachidonate; glyceryl behenate; glyceryl caprate; glyceryl caprylate; glyceryl caprylate/caprate; glyceryl cocoate; glyceryl diarachidate; glyceryl dibehenate; glyceryl dierucate; glyceryl dihydroxystearate; glyceryl diisopalmitate; glyceryl diisostearate; glyceryl dilaurate; glyceryl dilinoleate; glyceryl dimyristate; glyceryl dioleate; glyceryl dipalmitate; glyceryl dipalmitoleate; glyceryl diricinoleate; glyceryl distearate; glyceryl erucate; glyceryl hydroxystearate; glyceryl isostearate; glyceryl lanolate; glyceryl laurate; glyceryl lauratetoleate; glyceryl linoleate; glyceryl linolenate; glyceryl myristate; glyceryl octanoate/stearate/adipate; glyceryl oleate; glyceryl palmitate; glyceryl palmitate/stearate; glyceryl palmitate lactate; glyceryl ricinoleate; glyceryl sesquioleate; glyceryl stearate; glyceryl stearate citrate; glyceryl stearate diacetate; glyceryl stearate lactate; glyceryl triacetyl hydroxystearate; glyceryl triacetyl ricinoleate; glycine soja; glycine soja; glycol/butylene glycol montanate; glycol cetearate; glycol dibehenate; glycol dilaurate; glycol dioctanoate; glycol dioleate; glycol distearate; glycol ditallowate; glycol hydroxystearate; glycol oleate; glycol ricinoleate; glycol stearate; glycosaminoglycans; glycosphingolipids; gossypium; helianthus annus; helianthus annuus; heptylundecanol; hexadecyl methicone; hexamethyldisiloxane; hexanediol distearate; hexyl isostearate; hexyl laurate; hexyldecyl oleate; hordeum vulgare; hordeum vulgare; hydrogenated butylene/ethylene/styrene copolymer; hydrogenated C12–18 triglycerides; hydrogenated c6–14 olefin polymers; hydrogenated castor oil; hydrogenated castor oil laurate; hydrogenated coco-glycerides; hydrogenated coconut acid; hydrogenated coconut oil; hydrogenated cottonseed glyceride; hydrogenated cottonseed oil; hydrogenated ethylene/propylene/styrene copolymer; hydrogenated fish oil; hydrogenated jojoba oil; hydrogenated jojoba wax; hydrogenated lanolin; hydrogenated lard; hydrogenated menhaden oil; hydrogenated mink oil; hydrogenated olive oil unsaponifiables; hydrogenated orange roughy oil; hydrogenated palm/palm kernel oil PEG-6 esters; hydrogenated palm glyceride; hydrogenated palm glycerides; hydrogenated palm kernel glycerides; hydrogenated palm kernel oil; hydrogenated palm oil; hydrogenated peanut oil; hydrogenated polyisobutene; hydrogenated rapeseed oil; hydrogenated shark liver oil; hydrogenated soy glyceride; hydrogenated soybean glycerides; hydrogenated soybean oil; hydrogenated tallow; hydrogenated tallow acid; hydrogenated tallow alcohol; hydrogenated tallow glyceride; hydrogenated tallow glyceride citrate; hydrogenated tallow glyceride lactate; hydrogenated tallow glycerides; hydrogenated tallow glycerides citrate; hydrogenated vegetable glyceride; hydrogenated vegetable glycerides; hydrogenated vegetable glycerides phosphate; hydrogenated vegetable oil; hydrolyzed collagen; hydroxylated lanolin; hydroxylated milk glycerides; hydroxyoctacosanyl hydroxystearate; hyptis suaveolens; isatis tinctoria; isoamyl laurate; isobutyl myristate; isobutyl palmitate; isobutyl pelargonate; isobutyl stearate; isobutyl tallowate; isobutylated lanolin oil; isocetyl alcohol; isocetyl behenate; isocetyl isodecanoate; isocetyl linoleoyl stearate; isocetyl myristate; isocetyl palmitate; isocetyl salicylate; isocetyl stearate; isocetyl stearoyl stearate; isodeceth-2 cocoate; isodecyl citrate; isodecyl cocoate; isodecyl hydroxystearate; isodecyl isononanoate; isodecyl laurate; isodecyl myristate; isodecyl neopentanoate; isodecyl octanoate; isodecyl oleate; isodecyl palmitate; isodecyl stearate; isododecane; isododecene; isoeicosane; isohexadecane; isohexyl laurate; isohexyl neopentanoate; isohexyl palmitate; isolauryl behenate; isomerized jojoba oil; isononyl isononanoate; isopropyl arachidate; isopropyl avocadate; isopropyl behenate; isopropyl C12–15-pareth-9 carboxylate; isopropyl hydroxystearate; isopropyl isostearate; isopropyl lanolate; isopropyl laurate; isopropyl linoleate; isopropyl myristate; isopropyl oleate; isopropyl palmitate; isopropyl PPG-2-isodeceth-7 carboxylate; isopropyl ricinoleate; isopropyl stearate; isopropyl tallowate; isopropyl titanium triisostearate; isostearyl alcohol; isostearyl avocadate; isostearyl behenate; isostearyl benzoate; isostearyl erucate; isostearyl glyceryl pentaerythrityl ether; isostearyl isononanoate; isostearyl isostearate; isostearyl lactate; isostearyl myristate; isostearyl neopentanoate; isostearyl octanoate; isostearyl palmitate; isostearyl stearoyl stearate; isotridecyl isononanoate; isotridecyl myristate; jojoba alcohol; jojoba wax; juglans regia; lactis lipida; laneth-10 acetate; laneth-9 acetate; lanolin; lanolin; lanolin acid; lanolin alcohol; lanolin cera; lanolin linoleate; lanolin ricinoleate; lanosterol; lard glycerides; laureth-2 acetate; laureth-2 benzoate; laureth-2 octanoate; lauric/palmitic/oleic triglyceride; lauryl alcohol; lauryl behenate; lauryl cocoate; lauryl glycol; lauryl isostearate; lauryl lactate; lauryl myristate; lauryl oleate; lauryl palmitate; lauryl stearate; lauryldimonium hydroxypropyl hydrolyzed collagen; laurylmethicone copolyol; lavandula hybrida; lecithin; lesquerella fendleri; limnanthes alba; linoleic acid; linolenic acid; linoleyl lactate; linseed acid; linum usitatissimum; macadamia ternifolia; maleated soybean oil; mangifera indica; mango seed oil PEG-70 esters; MEL; methicone; methyl acetyl ricinoleate; methyl caproate; methyl caprylate; methyl caprylate/caprate; methyl cocoate; methyl dehydroabietate; methyl gluceth-20 benzoate; methyl glucose dioleate; methyl glucose laurate; methyl glucose sesquicaprylate/sesquicaprate; methyl glucose sesquicocoate; methyl glucose sesquiisostearate; methyl glucose sesquilaurate; methyl glucose sesquioleate; methyl glucose sesquistearate; methyl hydroxystearate; methyl laurate; methyl linoleate; methyl myristate; methyl oleate; methyl palmitate; methyl pelargonate; methyl ricinoleate; methyl stearate; mink oil PEG-13 esters; moringa pterygosperma; mortierella isabellina; musa sapientum; mustela; mustela; myreth-2 myristate; myreth-3 caprate; myreth-3 laurate; myreth-3 myristate; myreth-3 octanoate; myreth-3 palmitate; myristoyl hydrolyzed collagen; myristyl alcohol; myristyl isostearate; myristyl lactate; myristyl lignocerate; myristyl myristate; myristyl neopentanoate; myristyl octanoate; myristyl propionate; myristyl stearate; neopentyl glycol dicaprate; neopentyl glycol dicaprylate/dicaprate; neopentyl glycol dicaprylate/dipelargonate/dicaprate; neopentyl glycol dioctanoate; nonyl acetate; octacosanyl glycol; octacosanyl glycol isostearate; octyl acetoxystearate; octyl cocoate; octyl hydroxystearate; octyl isononanoate; octyl isopalmitate; octyl isostearate; octyl laurate; octyl myristate; octyl neopentanoate; octyl octanoate; octyl oleate; octyl palmitate; octyl pelargonate; octyl stearate; octyldecanol; octyldodecanol; octyldodecyl behenate; octyldodecyl benzoate; octyldodecyl erucate; octyldodecyl lactate; octyldodecyl myristate; octyldodecyl neodecanoate; octyldodecyl neopentanoate; octyldodecyl octanoate; octyldodecyl oleate; octyldodecyl ricinoleate; octyldodecyl stearate; octyldodecyl stearoyl stearate; oenothera biennis; olea europaea; olea europaca; oleic/linoleic triglyceride; oleic/palmitic/lauric/myristic/linoleic triglyceride; oleic acid; oleostearine; oleoyl hydrolyzed collagen; oleyl acetate; oleyl alcohol; oleyl arachidate; oleyl erucate; oleyl lactate; oleyl lanolate; oleyl linoleate; oleyl myristate; oleyl oleate; oleyl stearate; olive oil PEG-10 esters; olive oil PEG-6 esters; olus; omental lipids; orange peel wax; orbignya oleifera; oryza sativa; oryza sativa; ovum; ozonized jojoba oil; palm glyceride; palm glycerides; palm kernel acid; paln kernel alcohol; paln kernel glycerides; palm kernel wax; palmitic acid; palmitoyl hydrolyzed collagen; pantethine; papaver orientale; paraffin; paraffinum liquidum; PCA glyceryl oleate; peanut oil PEG-6 esters; PEG/PPG-125/30 copolymer; PEG/PPG-35/9 copolymer; PEG-10 coconut oil esters; PEG-10 hydrogenated lanolin; PEG-10 lanolin; PEG-10 polyglyceryl-2 laurate; PEG-11 castor oil; PEG-2 milk solids; PEG-20 hydrogenated lanolin; PEG-20 methyl glucose distearate; PEG-200 hydrogenated glyceryl palmate; PEG-4 proline linoleate; PEG4 proline linolenate; PEG-5 glyceryl triisostearate; PEG-5 hydrogenated lanolin; PEG-5 pentaerythrityl ether; PEG-5 tricetyl citrate; PEG-5 tridecyl citrate; PEG-5 trilauryl citrate; PEG-5 trimyristyl citrate; PEG-S tristearyl citrate; PEG-75 lanolin; PEG-8 hydrogenated fish glycerides; PEG-8 linoleate; PEG-8 linolenate; pellis lipida; pentadecyl alcohol; pentadesma butyracea; pentadoxynol-200; pentaerythrityl dioleate; pentaerythrityl isostearate/caprate/caprylate/adipate; pentaerythrityl stearate; pentaerythrityl stearate/caprate/caprylate adipate; pentaerythrityl tetraabietate; pentaerythrityl tetraacetate; pentaerythrityl tetrabehenate; pentaerythrityl tetrabenzoate; pentaerythrityl tetracaprylate/caprate; pentaerythrityl tetracocoate; pentaerythrityl tetraisononanoate; pentaerythrityl tetraisostearate; pentaeryrthrityl tetralaurate; pentaerythrityl tetrarynistate; pentaerythrityl tetraoctanoate; pentaerythrityl tetraoleate; pentaerythrityl tetrapelargonate; pentaerythrityl tetrastearate; pentaerythrityl trioleate; pentahydrosqualene; perfluoropolymethylisopropyl ether; persea gratissima; persea gratissima; petrolatum; petroleum hydrocarbon; phenyl dimethicone; phenyl methicone; phenyl trimethicone; phosphatidylcholine; pimenta acris; piscum iecur; pistacia vera; placental lipids; polyglyceryl-4 cocoate; polygonum aviculare; polyisoprene; polypentene; polyquaternium-2; polysilicone-3; polysilicone-4; polysilicone-5; PPG-1 trideceth-6; PPG-1-ceteth-1; PPG-1-ceteth-10; PPG-1-ceteth-20; PPG-1-ceteth-5; PPG-10 butanediol; PPG-10 cetyl ether phosphate; PPG-10 jojoba acid; PPG-10 jojoba alcohol; PPG-10 methyl glucose ether; PPG-10 oleyl ether; PPG-11 stearyl ether; PPG-12; PPG-12/SMDI copolymer; PPG-12 butyl ether; PPG-12-PEG-50 lanolin; PPG-12-PEG-65 lanolin oil; PPG-15; PPG-15 stearyl ether; PPG-15 stearyl ether benzoate; PPG-17; PPG-17 butyl ether; PPG-17 dioleate; PPG-2 butyl ether; PPG-2 hydrogenated tallowamine; PPG-2 isostearate; PPG-2 lanolin alcohol ether; PPG-2 myristyl ether propionate; PPG-2-buteth-2; PPG-2 ceteth-1; PPG-2-ceteth-5; PPG-20; PPG-20 butyl ether; PPG-20 lanolin alcohol ether; PPG-20 methyl glucose ether acetate; PPG-20 oleyl ether; PPG-23 oleyl ether, PPG-23-steareth-34; PPG-25 butyl ether phosphate; PPG-26; PPG-26 butyl ether; PPG-26 oleate; PPG-3 myristyl ether; PPG-3-deceth-2 carboxylic acid; PPG-3-ISODECETH-1; PPG-30; PPG-30 cetyl ether; PPG-30 isocetyl ether; PPG-30 lanolin alcohol ether; PPG-30 oleyl ether; PPG-34; PPG-36 oleate; PPG-36-buteth-36; PPG-37 oleyl ether; PPG-4 jojoba acid; PPG-4 jojoba alcohol; PPGA laureth-2; PPG-4 laureth-7; PPG-4 lauryl ether; PPG-4 myristyl ether; PPG-4-buteth-4; PPG-4-ceteth-20; PPG-4-deceth4; PPG-40-PEG-60 lanolin oil; PPG-5 lanolin alcohol ether; PPG-5 lanolin wax; PPG-5 lanolin wax glyceride; PPG-5 pentaerythrityl ether; PPG-5-buteth-5; PPG-5-laureth-5; PPG-50 oleyl ether; PPG-52 butyl ether; PPG-6-deceth-4; PPG-6-deceth-9; PPG-6-laureth-3; PPG-6-sorbeth-245; PPG-6-sorbeth-500; PPG-68-PEG-10 trimethylolpropane; PPG-7/succinic acid copolymer; PPG-7 lauryl ether; PPG-8 deceth-6; PPG-8 polyglyceryl-2 ether; PPG-9; PPG-9 diglyceryl ether; PPG-9 laurate; PPG-9-steareth-3; pristane; propylene glycol behenate; propylene glycol capreth-4; propylene glycol caprylate; propylene glycol ceteth-3 acetate; propylene glycol ceteth-3 propionate; propylene glycol citrate; propylene glycol cocoate; propylene glycol dicaprate; propylene glycol dicaproate; propylene glycol dicaprylate; propylene glycol dicaprylate/dicaprate; propylene glycol dicocoate; propylene glycol diisostearate; propylene glycol dilaurate; propylene glycol dioctanoate; propylene glycol dioleate; propylene glycol dipelargonate; propylene glycol distearate; propylene glycol hydroxystearate; propylene glycol isoceteth-3 acetate; propylene glycol isostearate; propylene glycol laurate; propylene glycol linoleate; propylene glycol linolenate; propylene glycol myristate; propylene glycol myristyl ether; propylene glycol myristyl ether acetate; propylene glycol oleate; propylene glycol oleth-5; propylene glycol ricinoleate; propylene glycol soyate; propylene glycol stearate; prunus armeniaca; prunus armeniaca; prunus avium; prunus dulcis; prunus persica; rapeseed glyceride; rapeseed glycerides; red petrolatum; rhus succedanea; ricinoleic acid; ricinus communis; rosa canina; rosa moschata; safflower glyceride; salmo; salvia hispanica; sesamum indicum; sesamum indicum; shellac; shellac cera; shorea stenoptera; silica dimnethyl silylate; silica silylate; simethicone; sorbitan distearate; soy acid; sphingolipids; squalane; squalene; squali iecur; stearoxy dimethicone; stearoxymethicone/dimethicone copolymer; stearoxytrimethylsilane; stearyl/aminopropyl methicone copolymer; stearyl acetate; stearyl alcohol; stearyl behenate; stearyl benzoate; stearyl caprylate; stearyl citrate; stearyl dimethicone; stearyl erucate; stearyl glycol; stearyl glycol isostearate; stearyl heptanoate; stearyl lactate; stearyl linoleate; stearyl methicone; stearyl octanoate; stearyl stearate; stearyl stearoyl stearate; sucrose distearate; sulfurized jojoba oil; sunflower seed oil glyceride; sunflower seed oil glycerides; synthetic candelilla wax; synthetic carnauba; synthetic japan wax; synthetic jojoba oil; synthetic wax; tall oil acid; tall oil glycerides; tall oil sterol; tallol; tallow acid; tallow alcohol; tallow glyceride; tallow glycerides; taraktogenos kurzii; tetrabutoxypropyl trisiloxane; tetradecyleicosanol; tetradecyleicosyl stearate; tetradecyloctadecanol; tetramethyl tetraphenyl trisiloxane; theobroma cacao; tri-C12–13 alkyl citrate; triarachidin; tribehenin; tricaprin; tricaprylin; tricaprylyl citrate; tridecyl alcohol; tridecyl behenate; tridecyl cocoate; tridecyl erucate; tridecyl isononanoate; tridecyl myristate; tridecyl neopentanoate; tridecyl octanoate; tridecyl stearate; tridecyl stearoyl stearate; tridecyl trimellitate; trierucin; triheptylundecanoin; trihydroxymethoxystearin; trihydroxystearin; triisocetyl citrate; triisononanoin; triisopalmitin; triisopropyl trilinoleate; triisostearin; triisostearin PEG-6 esters; triisostearyl citrate; triisostearyl trilinoleate; trilaurin; trilauryl citrate; trilinoleic acid; trilinolein; trilinolenin; trimethyl pentaphenyl trisiloxane; trimethylolpropane tricaprylate/tricaprate; trimethylolpropane tricocoate; trimethylolpropane triisostearate; trimethylolpropane trilaurate; trimethylolpropane trioctanoate; trimethylolpropane tristearate; trimethylsiloxysilicate; trimethylsilylamodimethicone; trimyristin; trioctanoin; trioctyldodecyl citrate; triolein; triolein PEG-6 esters; trioleyl phosphate; tripalmitin; tripadmitolein; triphenyl trimethicone; tripropylene glycol citrate; triricinolein; tris(tributoxysiloxy)methylsilane; trisebacin; tristearin; tristearyl citrate; triticum vulgare; triticum vulgare; triundecanoin; undecylpentadecanol; vegetable glycerides phosphate; vitis vinifera; wheat germ acid; wheat germ glycerides; *zea mays*.

Humectants useful in the invention as moisturizing agents include: 1,2,6-hexanetriol; acetamide MEA; aluminum hydroxide; arachidyl glycol; arginine PCA; butoxypropanol; butylene glycol; butyloctanol; capryl glycol; carboxymethyl chitosan succinamide; chitosan PCA; copper acetyl tyrosinate methylsilanol; copper PCA; copper PCA methylsilanol;

cyclomethicone; diglycerin; dimethicone copolyol acetate; dimethicone copolyol adipate; dimethicone copolyol behenate; dimethicone copolyol butyl ether; dimethicone copolyol hydroxystearate; dimethicone copolyol isostearate; dimethicone copolyol laurate; dimethicone copolyol methyl ether; dimethicone copolyol phosphate; dimethicone copolyol stearate; dimethicone copolyolamine; dimethicone silylate; dimethyl imidazolidinone; dimethylsilanol hyaluronate; dipotassium glycyrrhizate; erythritol; ethoxydiglycol; fructose; glucamine; gluconic acid; glucose; glucose glutamate; glucuronic acid; glutamic acid; glutamic acid; glycereth-12; glycereth-20; glycereth-26; glycereth-7; glycerin; glycogen; glycyrrhetinyl stearate; glycyrrhizic acid; heilmoor clay; hexacosyl glycol; hexanediol beeswax; hexanetriol beeswax; hexyldecanol; histidine; histidine; hyaluronic acid; hydrogenated honey; hydrogenated starch hydrolysate; hydrolyzed collagen; hydrolyzed elastin; hydrolyzed glycosaminoglycans; hydrolyzed keratin; hydrolyzed silk; hydrolyzed soy protein; hydrolyzed wheat protein/ dimethicone copolyol phosphate copolymer; hydroxyethyl sorbitol; inositol; inositol hexa-PCA; isopropyl hydroxybutyramide dimethicone copolyol; lactamide MEA; lactic acid; lactitol; lactose; lauryl PCA; lysine PCA; lysine PCA; lysine PCA; magnesium PCA; maltitol; manganese PCA; mannitol; MEL; menthyl PCA; methoxy PEG-10; methoxy PEG-100; methoxy PEG-16; methoxy PEG-40; methyl gluceth-10; methyl gluceth-20; methyl glucose dioleate; methylsilanol PCA; octyl PCA; PCA; PEG-10; PEG-10 propylene glycol; PEG-100; PEG-12; PEG-135; PEG-14; PEG-150; PEG-16; PEG-18; PEG-180; PEG-2 lactamide; PEG-20; PEG-20 stearate; PEG-200; PEG-240; PEG-25M; PEG-3 stearate; PEG-32; PEG-4; PEG-40; PEG-45M; PEG-6; PEG-60; PEG-75; PEG-8; PEG-8 stearate; PEG-9; PEG-90; placental protein; polydextrose; polyglucuronic acid; polyglycerin-3; polyglyceryl sorbitol; polysilicone-1; polysilicone-2; potassium dimethicone copolyol panthenyl phosphate; potassium dimethicone copolyol phosphate; potassium PCA; PPG-20 methyl glucose ether; PPG-20 methyl glucose ether distearate; PPG-38-buteth-37; propylene glycol; pyridoxine dilaurate; saccharide isomerate; serica; serum albumin; silk amino acids; sodium carboxymethyl chitin; sodium lactate; sodium mannuronate methylsilanol; sodium PCA; sodium PCA; sodium PCA methylsilanol; sodium PG-propyl thiosulfate dimethicone; sodium polyglutamate; soluble collagen; sorbitol; soy sterol; sucrose; sulfated castor oil; TEA-lactate; TEA-PCA; trehalose; tricontanyl PVP; trifluoromethyl C1–4 alkyl dimethicone; trilactin; urea; xylitol; *zea mays* ; zinc PCA.

The agent can also be a depilatory agent. A depilatory agent is an agent which removes body hair. Examples of depilatory agents include: alkali sulphides; alkaline earth sulphides; ammonium thioglycolate; ammonium thiolactate; barium sulfide; calcium sulfide; calcium thioglycolate; ethanolamine thioglycolate; glyceryl thioglycolate; isooctyl thioglycolate; lithium sulfide; magnesium sulfide; magnesium thioglycolate; mercaptopropionic acid; potassium sulfide; potassium thioglycolate; sodium sulfide; sodium thioglycolate; strontium sulfide; strontium thioglycolate; thioglycerin; thioglycollic acid and its salts; thiolactic acid; and zinc sulfide.

A preferred cosmetic agent is any of the known bulking agents which can be added to the hair or nails to provide 'body' and strength. Bulking agents are well known to those of ordinary skill in the art. Examples of bulking agents generally include cationic surfactantipolymers, fatty alcohols (non-ionic surfactant), waxes or esters, non-ionic polymers (e.g. polyglycols) for thickening, and insoluble silicone. The preferred bulking agent is the cationic surfactant, which places a dispersive charge on the hair. Examples of cationic surfactants include: quaternary ammonium hydroxides, e.g., tetramnethylammonium hydroxide, alkyltrimethylammonium hydroxides wherein the alkyl group has from about 8 to 22 carbon atoms, for example octyltrimethylammonium hydroxide, dodecyltrimethy-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides; cetylpyridinium hydroxide or salts thereof, e.g., chloride; Quaternium-5, Quaternium-31, Quaternium-18 and mixtures thereof. Additional bulking agents can be solutions of proteins, peptides, and polynucleotides or combinations thereof. Particular bulking agents include collagen, keratins, plant structural proteins, silk, fibrin, mucopolysaecharide and elastin. Other examples of bulking agents include: polylysine; biotin, panthenol, glycoprotein, and mucopolysaccharide; amodimethicone; acrylates; dimethicone copolymer; di-isobutyl adipate; isododecane; polypropylene glycol, glycerol, disaccharides, urea, dithiothreitol, edta, methyl paraben, propylparaben; polyvinylpyrrolidone and copolymers or derivatives thereof; for example, copolymers with the ethyl or butyl ester of PVA/MA (partially neutralized), copolymers with vinyl acetate/crotonic acid, copolymers of PVP/VA in all proportions, Polyquaternium-11, and copolymers with ethyl methacrylate/oleyl methacrylate/ diethylaminoethyl methacrylate quaternized with dimethyl sulfate, as well as carboxyvinyl polymers, such as hydroxyethyl cellulose, hydroxypropyl methylcellulose, and guar gum, zanthan gum, tragacanth gum, and other natural viscosity boosters; ceramide; copolymers of vinyl acetate and crotonic acid, terpolymers of vinyl acetate, crotonic acid and a vinyl ester of an alpha-branched saturated aliphatic monocarboxylic acid such as vinyl neodecanoate, and copolymers of methyl vinyl ether and maleic anhydride (molar ratio about 1:1) wherein such copolymers are 50% esterified with a saturated aliphatic alcohol containing from 1 to 4 carbon atoms such as ethanol or butanol; and acrylic copolymers and terpolymers containing acrylic acid or methacrylic acid as the anionic radical containing moiety such as terpolymers of methacrylic acid, butylacrylate and ethyl methacrylate which is presently the preferred acrylic polymer.

Bulking agents can be used as hair conditioning or hair fixative agents. Hair conditioning agents are agents which improve the appearance, texture and sheen of hair as well as increasing hair body or suppleness. Usually these compounds facilitate hair styling. Examples of hair conditioning agents include: Acetamide MEA; Acetamidoethoxybutyl Trimonium Chloride; Acetylated Lanolin; Acetylated Lanolin Alcohol; Acetylmethionyl Methylsilanol Elastinate; Acrylates/Carbamate Copolymer; Alanine; Albumen; Alfalfa (Medicago Sativa) Oil Unsaponifiables; Almondamidopropalkonium Chloride; Almondamidopropyl Betaine; Aluminum Capryloyl Hydrolyzed Collagen; Aluminum Undecylenoyl Collagen Amino Acids; Amino Bispropyl Dimethicone; Aminopropyl Dimethicone; Aminopropyl Laurylglutamine; Ammonium Caseinate; Ammonium Hydrolyzed Collagen; Ammmoniun Lauroyl Sarcosinate; Amodimethicone; Amodimethicone/Dimethicone Copolyol; Amodimethicone Hydroxystearate; AMP-Isostearoyl Gelatin/Keratin Amino Acids/Lysine Hydroxypropyltrimonium Chloride; AMP-Isostearoyl Hydrolyzed Collagen; AMP-Isostearoyl Hydrolyzed Soy Protein; AMP-Isostearoyl Hydrolyzed Wheat Protein; AMPD-Isostearcyl Hydrolyzed Collagen; AMPD-Rosin Hydrolyzed Collagen; Apricotamidopropyl Betaine; Apricotamidopropyl Ethyldimonium Ethosulfate; Argemone Mexicana Oil; Arginine; Arginine Aspartate; Asparagine; Aspartic Acid; Atelocollagen; Avocadamidopropyl Betaine; Avocado (Persea Gratissima) Oil Unsaponifiables; Babassuamide DEA; Babassuamidopropalkonium Chloride; Babassuamidopropylamine Oxide; Babassuamidopropyl Betaine; Beer; Behenamide DEA; Behenamide MEA; Behenamidopropyl Betaine; Behenamidopropyl Dimethylamine Behenate; Behenamidopropyl Dimethylamine Lactate; Behenamidopropyl Ethyldimonium Ethosulfate; Behenamidopropyl PG-Dimonium Chloride; Behenoyl PG-Trimonium Chloride; Behentrimonium Chloride; Behentrimonium Methosulfate; Behenyl Betaine; Behenyl Hydroxyethyl Imidazoline; Benzyltrimonium Hydrolyzed Collagen; Biotin; Bisphenylhexamethicone; Butoxy Chitosan; Buttermilk Powder; Butyloctyl Salicylate; Calcium Caseinate; Calcium Pantothenate; Canolamidopropyl Betaine; Canolamidopropyl Ethyldimonium Ethosulfate; Caproyl Sphingosine; Capryl/Capramidopropyl Betaine; Capryl Hydroxyethyl Imidazoline; Caproyl Collagen Amino Acids; Capryloyl Glycine; Capryloyl Hydrolyzed Collagen; Capryloyl Hydrolyzed Keratin; Capryloyl Keratin Amino Acids; Capryloyl Pea Amino Acids; Capryloyl Quinoa Amino Acids; Capryloyl Silk Amino Acids; Caprylyl Glycol; Caprylyl Hydroxyethyl Imidazoline; Caprylyl Pyrrolidone; Carboxybutyl Chitosan; Carboxymethyl Chitin; Carboxymethyl Chitosan Succinamide; Carboxymethyl Isostearamidopropyl Morpholine; Carnitine; Carpronium Chloride; Casein; Catalase; Cauliflower (Brassica Oleracea Botrytis) Oil Unsaponifiables; Ceramide 1; Ceramide 2; Ceramnide 3; Ceramide 4; Ceramide 5; Ceramide 1 A; Ceramide 6 II; Ceteartrimonium Chloride; Cetearyl Dimethicone/Vinyl Dimethicone Crosspolymer; Cetearyl Isononanoate; Cetearyl Octanoate; Cetearyl Palmitate; Cetyl Betaine; Cetyl Glycol; Cetyl Pyrrolidonylmethyl Dimonium Chloride; Cetyl Triethylammonium Dimethicone Copolyol Phthalate; Cholecalciferol Polypeptide; Cocamidoethyl Betaine; Cocamidopropylamine Oxide; Cocamidopropyl Amine Oxide; Cocamidopropyl Betaine; Cocamidopropyl Dimethylamine Dihydroxymethylpropionate; Cocamidopropyl Dimethylamine Hydrolyzed Collagen; Cocamidopropyl Dimethylamine Lactate; Cocamidopropyl Dimethylamine Propionate; Cocamidopropyl Dimethylaminohydroxypropyl Hydrolyzed Collagen; Cocamidopropyl Dimethylammonium C8–16 Isoalkylsuccinyl Lactoglobulin Sulfonate; Cocamidopropyldimonium Hydroxypropyl Hydrolyzed Collagen; Cocamidopropyl Ethyldimonium Ethosulfate; Cocamidopropyl Hydroxysultaine; Cocamidopropyl Morpholine; Cocamidopropyl Morpholine Lactate; Cocamidopropyl PG-Dimonium Chloride; Cocamidopropyl PG-Dimonium Chloride Phosphate; Cocamidopropyltrimonium Chloride; Cocamine Oxide; Cocaminobutyric Acid; Cocaminopropionic Acid; Cocoalkonium Chloride; Cocoamphodipropionic Acid; Cocobetainamido Amphopropionate; Coco-Betaine; Cocodimonium Hydroxypropyl Hydrolyzed Casein; Cocodimonium Hydroxypropyl Hydrolyzed Collagen; Cocodimonium Hydroxypropyl Hydrolyzed Hair Keratin; Cocodimonium Hydroxypropyl Hydrolyzed Keratin; Cocodimonium Hydroxypropyl Hydrolyzed Rice Protein; Cocodimonium Hydroxypropyl Hydrolyzed Silk; Cocodimonium Hydroxypropyl Hydrolyzed Soy Protein; Cocodimonium Hydroxypropyl Hydrolyzed Wheat Protein; Cocodimonium Hydroxypropyl Silk Amino Acids; Coco-Ethyldimoniun Ethosulfate; Coco-Hydroxysultaine; Coco-Morpholine Oxide; Coconut (Cocos Nucifera) Oil; Coco/Oleamidopropyl Betaine; Coco-Sultaine; Cocotrimonium Chloride; Cocotrimonium Methosulfate; Cocoyl Benzyl Hydroxyethyl Imidazolinium Chloride; Cocoyl Glutamic Acid; Cocoyl Hydrolyzed Collage; Cocoyl Hydrolyzed Keratin; Cocoyl Hydrolyzed Soy Protein; Cocoyl Hydroxyethyl Imidazoline; Cocoyl Hydroxyethylimidazolinium PG-Chloride phosphate; cocoyl sarcosinamide DEA; Cocyl sarcosine; Collagen; Collagen Amino Acids; Corn (Zea Mays) Gluten Protein; Corn (Zea Mays) Oil; Corn (Zea Mays) Oil Unsaponifiables; Crystallins; Cylcomethicone; Cysteine; Cysteine HCl; Cystine; DATEM; DEA-Cocoamphodipropionate; DEA-Cyclocarboxypropyloleate; DEA-Hydrolyzed Lecithin; DEA-Lauraminopropionate; Decyl Betaine; Decyl Mercaptomethylimidazole; Desamido Collagen; Dextran Hydroxypropyltrimonium Chloride; Diaminopyrimidine Oxide; Dibehenamidopropyldimethylamine Dilinoleate; DibehenyiDjarachidyl Dimonium Chloride; Dibehenyldimionium Chloride; Dibehenyldimonium Methosulfate; Dibutyl Lauroyl Glutamide; Di-C12–15 Alkyl Dimonium Chloride; Di-C12–18 Alkyl Dimonium Chloride; Di-C14-18 Alkyl Dimonium Chloride; Dicapryl/Dicaprylyl Dimonium Chloride; Dicapryloyl Cystine; Dicetyldiminium Chloride; Dicocodimethylamine Dilinoleate; Dicocodimonium Chloride; Dicocoylethyl Hydroxyethylmonium Methosolufate; Didecyldimonium Chloride; Diethylaminoethyl Cocoate; Diethylaminoethyl PEG-5 Cocoate; Diethylaminoethyl PEG-S Laurate; Diethylaminoethyl Stearate; Diethylene Glycol Dibenzoate; Diethylene Glycol Diisononanoate; Diethylene Glycol Dioctanoate; Diethylene Glycol Dioctanoate/Diisononanoate; Diethylene Tricaseinamide; Dihyrogenated Palmoylethyl Hydroxyethylmonium Methosulfate; Dihydrogenated Palmoyl Hydroxyethylmonium Methosulfate; Dihydrogenated.Tallowamidoethyl Hydroxyethylmonium Chloride; Dihydrogenated Tallowamidoethyl Hydroxyethylmonium Methosulfate; Dihydrogenated Tallow Benzylmonium Chloride; Dihyrodgenated Tallowethyl Hydroxyethylmonium Methosulate; Dihydrogenated Tallow Hydroxyethylmonium Methosulfate; Dihydrogenated Tallowoylethyl Hydroxyethylmonium Methosulfate; Dihydroxyethylamino Hydroxypropyl Oleate; Dihydroxyethyl C12–15 Alkoxypropylamine Oxide; Dihidroxyethyl Cocamine Oxide; Dihyroxyethyl Oleyl Glycinate; Dihydroxyethyl Soy Glycinate; Dihydroxyethyl Stearamine Oxide; Dihydroxyethyl Stearyl Glycinate; Dihydroxyethyl TallowaminetIPDI Copolymer; Dihydroxyethyl Tallowamine Oleate; dihydroxyethyl Tallowamine Oxide; dihydroxyethyl Tallow Glycinate; Dihydroxypropyl PEG-5 Linoleammonium Chloride Phosphate; Diisostearamidopropyl Epoxypropylmonium Chloride; Dilaureth4 Dimonium Chloride; Dilauryl Acetyl Dimonium Chloride; Dilauryldimonium Chloride; Dilinoleamidopropyl Dimethylanine Dimethicone Copolyol Phosphate; Dimenthicone Bisamino Hydroxypropyl Copolyol; Dimenthicone Copolyol; Dimethicone Copolyol Acetate; Dimethicone Copolyol Adipate; Dimethicone Copolyol Almondate; Dimethicone Copolyol Avocadoate; Dimethicone Copolyol Beeswax; Dimethicone Copolyol Bishydroxyethylamine; Dimethiocone Copolyol Borageate; Dimethicone Copolyol Butyl Ether; Dimethicone Copolyol Cocoa Butterate; Dimnethicone Copolyol Dhupa Butterate; Dimethicone Copolyol Ethyl Ether; Dimethicone Copolyol Kokum Butterate; Dimethicone Copolyol Lactate; Dimethicone Copolyol Mango Butterate; Dimethicone Copolyol Methyl Ether; Dimethicone Copolyol Mohwa Butterate; Dimethicone Copolyol Olivate; Dimethicone Copolyol Phthalate; Dimethicone Copolyol Sal Butterate; Dimethicone Copolyol Shea Butterate; Dimethicone Copolyol Undecylenate; Dimethicone Hydroxyptropyl Trimonioum Chloride; Dimethicone/Mercaptopropyl Methicone Copolymer; Dimethicone Propyl PG-Betaine; Dimethicone/Sodium PG-Propyidimethicone Thiosulfate- .Copolymer; Dimethiconol Arginine; Dimethiconol Cysteine; Dimethiconol Lactate; Dimethiconol Panthenol; Dimethiconolt Silsesquioxane Copolymer; Dimethaxysilyl Ethylenediaminopropyl Dimethicone; Dimethylaminopropylamido PCA Dimethicone; Dimethyl Aspartic Acid; Dimethyl Glutamic Acid; Dimethyl Lauramine Dimer Dilinoleate; Dimethyl Lauramine Isostearate; Dimethyl Lauramine Oleate; DimethylPABAmidopropyl Laurdimonium Tosylate; Dioctyldodeceth-2 Lauroyl Glutamate; Dioctyldodecyl Dodecanedioate; Dioctyldodecyl Lauroyl Glutamate; Dioleoyl EDTHP-Monium Methosulfate; Dioleoylethyl Hydroxyethylmonium Methosulfate; Dioleoylisopropyl Dimonium Methosulfate; Dipalmitoyl Cystine; Dipalmitoylethyl Dimonium Chloride; Dipalmitoylethyl Hydroxyethylmonium Methosulfate; Dipalmoylethyl Hydroxyethylmonium Methosulfate; Disodium Caproamphodiacetate; Disodium Caproamphodipropionate; Disodium Capryloamphodiacetate; Disodium Capryloamphodipropionate; Disodium Cocaminopropyl Iminodiacetate; Disodium Cocoamphocarboxyethylhydroxypropyisulfonate; Disodium Cocoamphodiacetate; Disodium Cocoamphodipropionate; Disodium Cystinyl Disuccinate; Disodium Dicarboxyethyl Cocopropylenediamine; Disodium Hydrogenated Tallow Glutamate; Disodium Isostearoamphodiacetate; Disodium lsostearoamphodipropionate; Disodium Laureth-5 Carboxyamphodiacetate; Disodium Lauriminodipropionate; Disodium Lauroamphodiacetate; Disodium Lauroamphodipropionate; Disodium Oleoamphodipropionate; Disodium PPG-2 Isodeceth-7 Carboxyamphodiacetate; Disodium Steariminodipropionate; Disodium Stearoamphodiacetate; Disodium Stearoyl Glutamate; Disodium Tallowamphodiacetate; Disodium Tallowiminodipropionate; Disodium Wheatgermamphodiacetate; Disoyamidoethyl Hydroxyethyl Ammonium Lactate; Disoydimoniun Chloride; Disoyoylethyl Hydroxyethylmonium Methosulfate; Disteareth-6 Dimonium Chloride; Disteareth-2 Lauroyl Glutamate; Disteareth-5 Lauroyl Glutamate; Distearoylethyl Dimonium Chloride; Distearoylethyl Hydroxyethyimonium Methosulfate; Distearoylpropyl Trimonium Chloride; Distearyldimethylamine Dilinoleate; Distearyldimonium Chloride; Distearyl Epoxypropylmonium Chloride; Ditallowamidoethyl Hydroxypropylamine; Ditallowamidoethyl Hydroxypropylmonium Methosulfate; Ditallow Dimonium Cellulose Sulfate; Ditallowdimonium Chloride; Ditallowethyl Hydroxyethylmonium Methosulfate; Ditallowoylethyl Hydroxyethylmonium Methosulfate; Ditridecyldimonium Chloride; Dodecylbenzyltrimonium Chloride; Dodecylhexadecyltrimonium Chloride; Dodecylxylylditrimonium Chloride; Egg; Egg Oil; Egg Powder; Elastin; Elastin Amino Acids; Erucalkonium Chloride; Erucamidopropyl Hydroxysultaine; Ethyl Almondate; Ethyl Apricot Kemelate; Ethyl Biotinate; Ethyl Ester of Hydrolyzed Animal Protein; Ethyl Ester of Hydrolyzed Keratin; Ethyl Ester of Hydrolyzed Silk; Ethyl Glutamate; Ethyl Hydroxymethyl Oleyl Oxazoline; Ethyl Minkate; Ethyl Morrhuate; Ethyl Myristate; Ethyl Oleate; Ethyl Olivate; Ethyl Palmitate; Ethyl Pelargonate; Ethyl Persate; Ethyl Serinate; Ethyl Stearate; Ethyl Wheat Germate; Fibronectin; Gelatin; Gelatin/Keratin Amino Acids/Lysine Hydroxypropyltrimonium Chloride; Gelatin/Lysine/Polyacrylamide Hydroxypropyltrimonium Chloride; Ginseng Hydroxypropyltrimonium Chloride; Glucaric Acid; Glucose Oxidase; Glutamic Acid; Glutamine; Glutamyl Histamine; Glyceryl Collagenate; Glyceryl Lanolate; Glycine; Glycoproteins; Glycyl Glycine; Guar Hydroxypropyltrimonium Chloride; Hair Keratin Amino Acids; Hexyldecyl Ester of Hydrolyzed Collagen; Hexyldodecyl Salicylate; Hinokitiol; Histidine; Histidine HCl; Human Placental Enzymes; Human Placental Lipids; Human Placental Protein; Hydrogenated Lanolin; Hydrogenated Olive Oil Unsaponifiables; Hydrogenated Palmtrimonium Chloride; Hydrogenated Tallowalkonium Chloride; Hydrogenated Tallow Betaine; Hydrogenated Tallowoyl Glutamic Acid; Hydrogenated Tallowtrimonium Chloride; Hydrolyzed Actin; Hydrolyzed Casein; Hydrolyzed Collagen; Hydrolyzed Conchiorin Protein; Hydrolyzed Corn Protein; Hydrolyzed DNA; Hydrolyzed Egg Protein; Hydrolyzed Elastin; Hydrolyzed Extensin; Hydrolyzed Fibronectin; Hydrolyzed Glycosarminoglycans; Hydrolyzed Hair Keratin; Hydrolyzed Hemoglobin; Hydrolyzed Human Placental Protein; Hydrolyzed Keratin; Hydrolyzed Lupine Protein; Hydrolyzed Maple Sycamore Protein; Hydrolyzed Milk Protein; Hydrolyzed Oat Flour; Hydrolyzed Oat Protein; Hydrolyzed Oats; Hydrolyzed Pea Protein; Hydrolyzed Placental Protein; Hydrolyzed Potato Protein; Hydrolyzed Reticulin; Hydrolyzed Rice Bran Protein; Hydrolyzed Rice Protein; Hydrolyzed RNA; Hydrolyzed Serum Protein; Hydrolyzed Silk; Hydrolyzed Soy Protein; Hydrolyzed Soy Protein/Dimethicone Copolyol Acetate; Hydrolyzed Spinal Protein; Hydrolyzed Sweet Almond Protein; Hydrolyzed Vegetable Protein; Hydrolyzed Wheat Gluten; Hydrolyzed Wheat Protein; Hydrolyzed Wheat Protein/Dimethicone Copolyol Acetate; Hydrolyzed Wheat Protein Hydroxypropyl Polysiloxane; Hydrolyzed Wheat Protein/PEG-20 Acetate Copolymer; Hydrolyzed Yeast; Hydrolyzed Yeast Protein; Hydrolyzed Zein; Hydroxycaproyl Phytosphingosine; Hydroxycapryloyl Phytosphingosine; Hydroxycetyl Hydroxyethyl Dimonium Chloride; Hydroxyethyl Behenamidopropyl Dimonium Chloride; Hydroxyethyl Carboxymethyl; Cocamidopropylamine; Hydroxyethyl Cetyldimonium Chloride; Hydroxyethyl Cetyldimonium Phosphate; Hydroxyethyl Diphenyl Imidazoline; Hydroxyethyl Hydroxypropyl C12–15 Alkoxypropylamine Oxide; Hydroxyethyl Laurdimonium Chloride; Hydroxyethyl Tallowdimonium Chloride; Hydroxylauroyl Phytosphingosine; Hydroxyphenyl Glycinamide; Hydroxyproline; Hydroxypropyl Biscetearyldimonium Chloride; Hydroxypropyl Bisisostearamidopropyldimonium Chloride; Hydroxypropyl Bisoleyldimonium Chloride; Hydroxypropyl Bisstearyidimonium Chloride; Hydroxypropyldimethicone; Hydroxypropyl Guar Hydroxypropyltrimonium Chloride; Hydroxypropyltrimonium Gelatin; Hydroxypropyitrimonium Honey; Hydroxypropyltrimonium Hydrolyzed Casein; Hydroxypropyltrimonium Hydrolyzed Collagen; Hydroxypropyltrimonium Hydrolyzed Keratin; Hydroxypropyltrimonium Hydrolyzed Rice Bran Protein; Hydroxypropyltrimonium Hydrolyzed Silk; Hydroxypropyltrimonium Hydrolyzed Soy Protein; Hydroxypropyltrimonium Hydrolyzed Vegetable Protein; Hydroxypropyltrimonium Hydrolyzed Wheat Protein; Hydroxystearamidopropyl Trimonium Chloride; Hydroxystearamidopropyl Trimonium Methosulfate;lnositol; Iodized Corn Protein; Isobutylated Lanolin Oil; Isoleucine; Isostearamidopropylamine Oxide; Isostearamidopropyl Betaine; Isostearamidopropyl Epoxypropylmorpholinium Chloride; Isostearamidopropyl Ethyldimonium Ethosulfate; Isostearamidopropyl Ethylmorpholinium Ethosulfate; Isostearamidopropyl Laurylacetodimnonium Chloride; Isostearamidopropyl Morpholine Oxide; Isostearamidopropyl PG-Dimonium Chloride; Isostearaminopropalkonium Chloride; Isostearoyl Hydrolyzed Collagen; Isostearoyl PG-Trimonium Chloride; Isostearyl Benzylimidonium Chloride; Isostearyl Ethyldimonium Chloride; Isostearyl Ethylimidazolinium Ethosulfate; Isostearyl Glyceryl Pentaerythrityl Ether; Isostearyl Hydroxyethyl Imidazoline; Isostearyl Laurdimonium Chloride; Isotridecyl Laurate; Isotridecyl Myristate; Jojoba Butter; Jojoba (Buxus Chinensis) Oil; Jojoba Wax; Juniperus Oxycedrus Tar; Keratin; Keratin Amino Acids; Lactamide MEA; Lactoferrin; Lactoglobulin; Lactoyl Methylsilanol Elastinate; Lactoyl Phytosphingosine; Laneth-9 Acetate; Laneth-10 Acetate; Lanolin; Lanolin Alcohol; Lanolin Linoleate; Lanolin Oil; Lanolin Ricinoleate; Lanolin Wax; Lanosterol; Lauramidopropylamine Oxide; Lauramidopropyl Betaine; Lauramidopropyl PG-Dimonium Chloride; Lauramine Oxide; Lauraminopropionic Acid; Laurdimonium Hydroxypropyl Hydrolyzed Soy Protein; Laurdimonium Hydroxypropyl Hydrolyzed Wheat Protein; Lauroamphodipropionic Acid; Lauroyl Collagen Amino Acids; Lauroyl Hydrolyzed Collagen; Lauroyl Hydrolyzed Elastin; Lauroyl Lysine; Lauroyl PG-Trimonium Chloride; Lauroyl Sarcosine; Lauroyl Silk Amino Acids; Laurtrimonium Bromide; Laurylamine Dipropylenediamine; Lauryl Aminopropylglycine; Lauryl Betaine; Lauryl Diethylenediaminoglycine; Lauryl Dimethylanine Cyclocarboxypropyloleate; Lauryldimonium Hydroxypropyl Hydrolyzed Casein; Lauryldimonium Hydroxypropyl Hydrolyzed Collagen; Lauryldimonium Hydroxypropyl Hydrolyzed Keratin; Lauryldimonium Hydroxypropyl Hydrolyzed Silk; Lauryldimonium Hydroxypropyl Hydrolyzed Soy Protein; Lauryl Glycol; Lauryl Hydroxyethyl Imidazoline; Lauryl Hydroxysultaine; Lauryl Methyl Gluceth-10 Hydroxypropyldimonium Chloride; Lauryl Myristate; Lauryl Pyrrolidone; Lauryl Sultaine; Lecithinamide DEA; Leucine; Linoleamide; Linoleamide DEA; Linoleamide MEA; Linoleamide MIPA; Linoleamidopropalkonium Chloride; Linoleamidopropyl Dimethylamine Dimer Dilinoleate; Linoleamidopropyl Ethyldimonium Ethosulfate; Linoleamidopropyl PG-Dimonium Chloride Phosphate Dimethicone; Linoleic Acid; Linolenic Acid; Lupin (Lupinus Albus) Oil Unsaponiflables; Lysine; Lysine Aspartate; Maltodextrin; Marmot Oil; MEA-10 Hydrolyzed Collagen; MEA-Hydrolyzed Silk; Methionine; Methyl Aspartic Acid; Methyl Glutamic Acid; Methyl Hydroxycetyl Glucaminium Lactate; Methyl Hydroxymethyl Oleyl Oxazoline; Methylsilanol Acetylmethionate; Methylsilanol Elastinate; Milkamidopropyl Amine Oxide; Milkamidopropyl Betaine; Milk Amino Acids; Milk Protein; Mineral Oil; Minkamidopropalkonium Chloride; Minkamidopropylamine Oxide; Minkamidopropyl Betaine; Minkanidopropyl Ethyldimonium Ethosulfate; Mink Oil; Mink Wax; Mixed Isopropanolamines Lanolate; Myristamidopropylamine Oxide; Myristamidopropyl Betaine; Myristamine Oxide; Myristaminopropionic Acid; Myristoyl Glutamic Acid; Myristoyl Hydrolyzed Collagen; Myristoyl Sarcosine; Myristyl Betaine; MyristyVCetyl Amine Oxide; Myristyl Hydroxyethyl Imidazoline; Niacin; Niacinamide; Nonfat Dry Colostrum; Nonfat Dry Milk; Norvaline; Oat (Avena Sativa) Protein; Octyldodecyl Lanolate; Octyldodecyltrimonium Chloride; Olealkonium Chloride; Oleamidopropylamine Oxide; Oleamidopropyl Betaine; Oleamidopropyl Dimethylamine Glycolate; Oleamidopropyl Dimethylamine Hydrolyzed Collagen; Oleamidopropyl Dimethylamine Lactate; Oleamidopropyl Dimethylamine Propionate; Oleamidopropyldimonium Hydroxypropyl Hydrolyzed Collagen; Oleamidopropyl Hydroxysultaine; Oleamidopropyl PG-Dimonium Chloride; Oleamine Bishydroxypropyltrimonium Chloride; Oleamine Oxide; Oleoyl Hydrolyzed Collagen; Oleoyl PG-Trimonium Chloride; Oleoyl Sarcosine; Oleyl Betaine; Oleyl Epoxypropyldimonium Chloride; Oleyl Hydroxyethyl Imidazoline; Oleyl Lanolate; Oleyl Linoleate; Oleyl Myristate; Oleyl Oleate; Oleyl Stearate; Olivamidopropylamine Oxide; Olivamidopropyl Betaine; Olivamidopropyl Dimethyiamine Lactate; Olive (Olea Europaea) Oil Unsaponifiables; Ostrich Oil; Oxidized Keratin; Palmamidopropyl Betaine; Palmitamidopropylanine Oxide; Palmitamidopropyl Betaine; Palmitamine Oxide; Palmitoyl Collagen Amino Acids; Palmitoyl Glycine; Palmitoyl Hydrolyzed Collagen; Palmitoyl Hydrolyzed Milk Protein; Palmitoyl Hydrolyzed Wheat Protein; Palmitoyl Keratin Amino Acids; Paimitoyl Pea Amino Acids; Palmitoyl PG-Trimonium Chloride; Paimitoyl Quinoa Amino Acids; Palmitoyl Silk Amino Acids; Palm Kernelamidopropyl Betaine; Pancreatin; Pantethine; Panthenol; Panthenyl Ethyl Ether; Panthenyl Ethyl Ether Acetate; Panthenyl Hydroxypropyl Steardimonium Chloride; Panthenyl Triacetate; Pantothenic Acid; Pantothenic Acid Polypeptide; Papain; PCA Dimethicone; PCA Ethyl Cocoyl Arginate; PEG-105 Behenyl Propylenediamine; PEG-2 Dimeadowfoanamidoethylmonium Methosulfate; PEG-3 Dioleoylamidoethylmonium Methosulfate; PEG-5 Ditridecylmonium Chloride; PEG-5 Hydrogenated Lanolin; PEG-10 Hydrogenated Lanolin; PEG-20 Hydrogenated Lanolin; PEG-24 Hydrogenated Lanolin; PEG30 Hydrogenated Lanolin; PEG-70 Hydrogenated Lanolin; PEG-5 Lanolinamide; PEG-3 Lauramine Oxide; PEG-2 Milk Solids; PEG-5 Oleamide Dioleate; PEG-2 Oleammonium Chloride; PEG-8/SMDI Copolymer; PEG-15 Stearmonium Chloride; PEG-20 Tallow Ammonium Ethosulfate; PEG-I 5 Tallow Polyamine; PEG-3 Tallow Propylenedimonium Dimethosulfate; Pepsin; Petrolatum; PG-Hydroxyethylcellulose Cocodimonium Chloride; PG-Hydroxyethylcellulose Lauryldimonium Chloride; PG-Hydroxyethylcellulose Stearyldimonium Chloride; Phenylalanine; Phenyl Trimethicone; Phytosphingosine; Phytosteryl Macadamiate; Placental Enzymes; Placental Lipids; Placental Protein; Polybeta-Alanine; Polyglyceryl-2 Oleyl Ether; Polyglyceryl4 Oleyl Ether; Polylysine; Polymethacrylamidopropyltrimonium Chloride; Polymethacrylamidopropyltrimoniun Methosulfate; Potymethylglutamate; Polyquaternium43; Polyquaternium-44; Polysilicone-1; Polysilicone-2; Polysilicone-3; Polysilicone4; Polysilicone-5; Polysilicone-6; Polysilicone-7; Polysilicone-8; Polysilicone-10; Potassium Abietoyl Hydrolyzed Collagen; Potassium Caseinate; Potassium Cocoyl Glutamate; Potassium Cocoyl Glycinate; Potassium Coccyl Hydrolyzed Casein; Potassium Cocoyl Hydrolyzed Collagen; Potassium Cocoyl Hydrolyzed Corn Protein; Potassium Cocoyl Hydrolyzed Keratin; Potassium Cocoyl Hydrolyzed Potato Protein; Potassium Cocoyl Hydrolyzed Rice Bran Protein; Potassium Cocoyl Hydrolyzed Rice Protein; Potassium Cocoyl Hydrolyzed Silk; Potassium Cocoyl Hydrolyzed Soy Protein; Potassium Cocoyl Hydrolyzed Wheat Protein; Potassium Dihydroxyethyl Cocamine Oxide Phosphate; Potassium Dimethicone Copolyol Panthenyl Phosphate; Potassium Lauroyl Collagen Amino Acids; Potassium Lauroyl Glutamate; Potassium Lauroyl Hydrolyzed Collagen; Potassium Lauroyl Hydrolyzed Soy Protein; Potassium Lauroyl Wheat Amino Acids; Potassium Myristoyl Glutamate; Potassium Myristoyl Hydrolyzed Collagen; Potassium Oleoyl Hydrolyzed Collagen; Potassium Palmitoyl Hydrolyzed Wheat Protein; Potassium Stearoyl Hydrolyzed Collagen; Potassium Undecylenoyl Alginate; Potassium Undecylenoyl Carrageenan; Potassium Undecylenoyl Hydrolyzed Collagen; Potassium Undecylenoyl Hydrolyzed Corn Protein; Potassium Undecylenoyl Hydrolyzed Soy Protein; Potassium Undecylenoyl Hydrolyzed Wheat Protein; PPG-2-Buteth-2; PPG-2-Buteth-3; PPG-3-Buteth-5; PPG-4-Buteth4; PPG-5-Buteth-5; PPG-5-Buteth-7; PPG-7-Buteth-10; PPG-9 Buteth-12; PPG-10-Buteth-9; PPG-12-Buteth-12; PPG-12-Buteth-16; PPG-15-Buteth-20; PPG-17-Buteth-17; PPG-20-Buteth-30; PPG-24-Buteth-27; PPG-26-Buteth-26; PPG-2810 Buteth-35; PPG-30-Buteth-30; PPG-33-Buteth45; PPG-36-Buteth-36; PPG-38-Buteth-37; PPG-2 Butyl Ether; PPG-4 Butyl Ether; PPG-5 Butyl Ether; PPG-9 Butyl Ether; PPG-12 Butyl Ether-, PPG-14 Butyl Ether; PPC-15 Butyl Ether; PPG-16 Butyl Ether; PPG-17 Butyl Ether; PPG-18 Butyl Ether; PPG-20 Butyl Ether; PPG-22 Butyl Ether; PPG-24 Butyl Ether; PPG-26 Butyl Ether; PPG-30 Butyl Ether; PPG-33 Butyl Ether; PPG-40 Butyl Ether; PPG-52 Butyl Ether; PPG-53 Butyl Ether; PPG-9 Diethylmonium Chloride; PPG-2 Lanolin Alcohol Ether; PPG-5 Lanolin Alcohol Ether; PPG-10 Lanolin Alcohol Ether; PPG-20 Lanolin Alcohol Ether; PPG-30 Lanolin Alcohol Ether; PPG-10 Methyl Glucose Ether; PPG-20 Methyl Glucose Ether; PPG-20-PEG-20 Hydrogenated Lanolin; PPG-12-PEG-50 Lanolin; PPG-12-PEG-65 Lanolin Oil; PPG-40-PEG-60 Lanolin Oil; PPG-12/SMDI Copolymer; PPG-51/SMDI Copolymer; PPG-7/Succinic Acid Copolymer; Procollagen; Proline; Propyltrimonium Hydrolyzed Collagen; Propyltrimonium Hydrolyzed Soy Protein; Propyltrimonium Hydrolyzed Wheat Protein; Pyridoxine; Pyridoxine Dicaprylate; Pyridoxine Dilaurate; Pyridoxine Dioctenoate; Pyridoxine Dipalrnitate; Pyridoxine HCl; Pyridoxine Tripalmitate; Quaternium-8; Quaterniumr-14; Quaternium-16; Quaternium-22; Quaternium-25 Quaternium-26; Quaternium-27; Quaternium-33; Quaternium-52; Quaternium-53; Quaternium-56; Quaternium-60; Quaternium-61; Quaternium-63; Quaternium-70; Quaternium-72; Quaternium-75; Quaternium-76 Hydrolyzed Collagen; Quaternium-77; Quaternium-78; Quaternium-79 Hydrolyzed Collagen; Quaternium-79 Hydrolyzed Keratin; Quaternium-79 Hydrolyzed Milk Protein; Quaterniurn-79 Hydrolyzed Silk; Quaterniun-79 Hydrolyzed Soy Protein; Quaternium-79 Hydrolyzed Wheat Protein; Quaternium-80; Quaternium-81; Quaternium-82; Quaternium-83; Quaternium-85; Quaternium-86; Quinine; Rapeseed (Brassica; Campestris) Oil Unsaponifiables; Resorcinol Acetate; Ricinoleamidopropyl Betaine; Ricinoleamidopropyltrimonium Chloride; Ricinoleamnidopropyltrimonium Methosulfate; Rosin Hydrolyzed Collagen; Rutin; Saffloweramidopropyl Ethyldimonium Ethosulfate; Salicylic Acid; Selenium Sulfide; Sericin; Serine; Serum Albumin; Serun Protein; Sesame (Sesamum Indicum) Oil Unsaponifiables; Sesamidopropylamine Oxide; Sesamidopropyl Betaine; Shea Butter (Butyrospernum Parkii) Unsaponifiables; Shellac Wax; Silicone Quaternium-1; Silicone Quaternium-2; Silicone Quaternium-3; Silicone Quaternium4; Silicone Quaternium-5; Silicone Quaternium6; Silicone Quaternium-7; Silicone Quaternium-8; Silicone Quaternium-9; Silicone Quaternium-10; Silicone Quaternium-1 1; Silicone Quaternium-12; Silicone Quaternium-13; Silk Amino Acids; Sodium C12–15 Alkoxypropyl Iminodipropionate; Sodiun Caproamphoacetate; Sodium Caproamphohydroxypropylsulfonate; Sodium Caproamphopropionate; Sodium Capryloamphoacetate; Sodium Capryloamphohydroxypropylsulfonate; Sodium Capryloamphopropionate; Sodium Caseinate; Sodium Chondroitin Sulfate; Sodium C8–16 Isoalkylsuccinyl Lactoglobulin Suffonate; Sodium Cocaminopropionate; Sodium Cocoamphoacetate; Sodium Cocoamphohydroxypropylsulfonate; Sodium Cocoamphopropionate; Sodium Cocoyl Collagen Amino Acids; Sodium Cocoyl Hydrolyzed Collagen; Sodium Cocoyl Hydrolyzed Keratin; Sodium Cocoyl Hydrolyzed Rice Protein; Sodium Cocoyl Hydrolyzed Soy Protein; Sodium Cocoyl Hydrolyzed Wheat Protein; Sodium Cocoyl Sarcosinate; Sodium Commamphopropionate; Sodium Dicarboxyethylcoco Phosphoethyl Imidazoline; Sodium Diethylaminopropyl Cocoaspartamide; Sodium Dimethicone Copolyol Acetyl Methyltaurate; Sodium Glutamate; Sodium Hydrolyzed Casein; Sodium Hydroxymethylglycinate; Sodium Isostearoamphoacetate; Sodium Isostearoamphopropionate; Sodiun Lauraminopropionate; Sodium Lauraminodipropionate; Sodium Lauroanphoacetate; Sodium Lauroamphohydroxypropylsulfonate; Sodium Lauroampho PG-Acetate Phosphate; Sodium Lauroamphopropionate; Sodium Lauroyl Aspartate; Sodium Lauroyl Collagen Amino Acids; Sodium Lauroyl Glutamate; Sodium Lauroyl Hydrolyzed Collagen; Sodium Lauroyl Hydrolyzed Silk; Sodium Lauroyl Oat Amino Acids; Sodium Lauroyl Sarcosinate; Sodium Lauroyl Silk Amino Acids; Sodium Lauroyl Wheat Amino Acids; Sodium Milkamidopropyl PG-Dimonium Chloride Phosphate; Sodium Myristoamphoacetate; Sodium Myristoyl Hydrolyzed Collagen; Sodium Myristoyl Isethionate; Sodium Myristoyl Sarcosinate; Sodium Oleoamphoacetate; Sodium Oleoamphohydroxypropylsulfonate; Sodium Oleoamphopropionate; Sodium Oleoyl Hydrolyzed Collagen; Sodium Oleoyl Isethionate; Sodium Palmitoyl Chondroitin Sulfate; Sodium Palmitoyl Hydrolyzed Collagen; Sodium Palmitoyl Hydrolyzed Wheat Protein; Sodiun Pantothenate; Sodium PCA; Sodium PG-Propyl Thiosulfate Dimethicone; Sodium Polyaspartate; Sodium Polyglutamate; Sodium Ricinoleoamphoacetate; Sodium Soy Hydrolyzed Collagen; Sodium Stearoamphoacetate; Sodium Stearoamphohydroxypropylsulfonate; Sodium Stearoamphopropionate; Sodium Stearoyl Casein; Sodium Stearoyl Chondroitin Sulfate; Sodium Stearoyl Glutanate; Sodium Stearoyl Hyaluronate; Sodium Stearoyl Hydrolyzed Collagen; Sodium Stearoyl Hydrolyzed Corn Protein; Sodium Stearoyl Hydrolyzed Silk; Sodium Stearoyl Hydrolyzed Soy Protein; Sodium Stearoyl Hydrolyzed id Wheat Protein; Sodiumn Stearoyl Lactalbumin; Sodium Stearoyl Oat Protein; Sodiun Stearoyl Pea Protein; Sodium Stearoyl Soy Protein; Sodium Tallamphopropionate; Sodium Tallowamphoacetate; Sodium/TEA-Lauroyl Collagen Amino Acids; Sodium/TEA-Lauroyl Hydrolyzed Collagen; Sodium/TEA-Lauroyl Hydrolyzed Keratin; Sodium/TEA-Lauroyl Keratin Amino Acids; Sodium/TEA-Undecylenoyl Alginate; Sodium/TEA-Undecylenoyl Carrageenan; Sodium/TEA-Undecylenoyl Collagen Amino Acids; Sodium/TEA-Undecylenoyl Hydrolyzed Collagen; Sodium/TEA-Undecylenoyl Hydrolyzed Corn Protein; Sodium/TEA-Undecylenoyl Hydrolyzed Soy Protein; Sodium/TEA-Undecylenoyl Hydrolyzed Wheat Protein; Sodium Undecylenoamphoacetate; Sodium Undecylenoamphopropionate; Sodium Wheat Germamphoacetate; Soluble Collagen; Soluble Proteoglycan; Soyamidoethyldimonium/Trimonium Hydroxypropyl Hydrolyzed Wheat Protein; Soyamidopropyl Betaine; Soybean (Glycine Soja) Oil Unsaponiflables; Soybean (Glycine Soja) Protein; Soybean Lipid; Soy Dihydroxypropyldimonium Glucoside; Soydimonium Hydroxypropyl Hydrolyzed Wheat Protein; Soycthyldimonium Ethosulfate; Soy Hydroxyethyl Imidazoline; Soytrimonium Chloride; Squalane; Squalene; Stearalkonium Dimethicone Copolyol Phthalate; Stearamidoethyl Diethylamine; Stearamidoethyl Diethylamine Phosphate; Stearamidopropylamine Oxide; Stearamidopropyl Betaine; Stearamidopropyl Dimethylamine; Stearamidopropyl Dimethylamine Lactate; Stearamidopropyl Dimethylamine Stearate; Stearamidopropyl Ethyldimonium Ethosulfate; Stearamidopropyl PG-Dimonium Chloride Phosphate; Stearamidopropyl Pyrrolidonylmethyl Dimonium Chloride; Stearamidopropyl Trimonium Methosulfate; Stearamine Oxide; Steardimonium Hydroxypropyl Hydrolyzed Casein; Steardimonium Hydroxypropyl Hydrolyzed Collagen; Steardimonium Hydroxypropyl Hydrolyzed Keratin; Steardimonium Hydroxypropyl Hydrolyzed Rice Protein; Steardimonium Hydroxypropyl Hydrolyzed Silk; Steardimonium Hydroxypropyl Hydrolyzed Vegetable Protein; Steardimonium Hydroxypropyl Hydrolyzed Wheat Protein; Stearoyl Glutamic Acid; Stearoyl Leucine; Stearoyl PG-Trimonium Chloride; Stearoyl Sarcosine; Steartrimonium Bromide; Steartrimonium Chloride; Steartrimonium Hydroxyethyl Hydrolyzed Collagen; Steartrimonium Methosulfate; Steartrimonium Saccharinate; Stearyl/Aminopropyl Methicone Copolymer; Stearyl Betaine; Stearyl Hydroxyethyl Imidazoline; Stearyl Hydroxyethylimidonium Chloride; Stearyl Octyldimonium Chloride; Stearyl Octyldimonium Methosulfate; Stearyl PG-Dimonium Chloride Phosphate; Sulfur; Sulfurized Hydrolyzed Corn Protein; Sulfilrized TEA-Ricinoleate; Sunflower (Helianthus Annuus) Seed Oil Unsaponifiables; Sweet Almond (Prunus Amygdalus; Dulcis) Protein; Tall Oil Benzyl Hydroxyethyl Imidazolinium Chloride; Tall Oil Hydroxyethyl Imidazoline; Tallowamidopropylamine Oxide; Tallowamidopropyl Betaine; Tallowamidopropyl Hydroxysultaine; Tallowamine Oxide; Tallow Betaine; Tallow Dihydroxyethyl Betaine; Tallow Hydroxyethyl Imidazoline; Tallowtrimonium Chloride; TEA-Abietoyl Hydrolyzed Collagen; TEA-Cocoyl Glutamate; TEA-Cocoyl Hydrolyzed Collagen; TEA-Cocoyl Hydrolyzed Soy Protein; TEA-Cocoyl Sarcosinate; TEA-Hydrogenated Tallowoyl Glutamate; TEA-Isostearoyl Hydrolyzed Collagen; TEA-Lauraminopropionate; TEA-Lauroyl Collagen Amino Acids; TEA-Lauroyl Glutamate; TEA-Lauroyl Hydrolyzed Collagen; TEA-Lauroyl Keratin Amino Acids; TEA-20 Lauroyl Sarcosinate; TEA-Myristarinopropionate; TEA-Myristoyl Hydrolyzed Collagen; TEA-Oleoyl Hydrolyzed Collagen; TEA-Oleoyl Sarcosinate; TEA-Palm Kernel Sarcosinate; TEA-Undecylenoyl Hydrolyzed Collagen; Tetrabutoxypropyl Trisiloxane; Thenoyl Methionate; Thiodiglycolamide; Threonine; Tricetylmonium Chloride; Triethonium Hydrolyzed Collagen Ethosulfate; Trimethylsilyamodimethicone; Trioctanoin; TriPABA Panthenol; Trisodium Lauroampho PG-Acetate Chloride Phosphate; Triundecanoin; Tryptophan; Tyrosine; Undecylenamide DEA; Undecylenamide MEA; Undecylenamidopropylamine Oxide; Undecylenamidopropyl Betaine; Undecylenanidopropyltrimonium Methosulfate; Undecylenoyl Hydrolyzed Collagen; Undecylenoyl Wheat Amino Acids; Undecylenoyl Xanthan Gum; Valine; Vegetable Oil; Wheat Amino Acids; Wheat Germamidopropalkonium Chloride; Wheat Germamidopropylamine Oxide; Wheat Germamidopropyl Betaine; Wheatgermamidopropyl Dimethylamine Hydrolyzed Collagen; Wheatgermamidopropyl Dimethylamine Hydrolyzed Wheat Protein; Wheat Germamidopropyldimonium Hydroxypropyl Hydrolyzed Wheat Protein; Wheat Germamidopropyl Epoxypropyldimonium Chloride; Wheatgermamidopropyl Etbyldimonium Ethosulfate; Wheat (Triticum Vulgare) Germ Oil Unsaponifiables; Wheat (Triticum Vulgare) Germ Protein; Wheat (Triticum Vulgare) Gluten; Wheat (Triticum Vulgare) Protein; Whey Protein; Yogurt; Zein; Zinc Hydrolyzed Collagen.

Antistatic agents can sometimes also be used as hair conditioning agents, Antistatic agents are agents reduce static electricity by neutralizing electrical charge on a surface. Antistatic agents include: acetamide MEA; acetamidoethoxybutyl trimonium chloride; acetamidopropyl trimonium chloride; acetum; acetylated lanolin; acetylated lanolin alcohol; acetylated lanolin ricinoleate; acetylmethionyl methylsilanol elastinate; acrylamide/sodium acrylate copolymer; acrylamides copolymer; acrylates/ammonium methacrylate copolymer acrylates/pvp copolymer; acrylates copolymer; adipic acid/dimethylaminohydroxypropyl diethylenetriamine copolymer; adipic acid/epoxypropyl diethylenetriamine copolymer; alanine; allantoin acetyl methionine; almondamidopropalkonium chloride; almonda. midopropyl dimethylamine; aluminum capryloyl hydrolyzed collagen; aluminum undecylenoyl collagen amino acids; aminoethylacrylate phosphate/acrylates copolymer aminopropyl laurylglutamine; ammonium acrylates copolymer; ammonium caseinate; ammionium hydrolyzed collagen; ammonium lauroyl sarcosinate; ammonium VA/acrylates copolymer; amodimethicone; amodimethicone/dimethicone copolyol; amp-isostearoyl hydrolyzed collagen; apricotamidopropyl ethyldimonium ethosulfate; arginine; asparagine; aspartic acid; avocadamidopropalkonium chloride; avocadamidopropyl dirnethylamine; babassuamidopropalkonium chloride; babassuarnidopropyl dimethylamine; behenalkonium chloride; behenarnidopropyl dimethylamine; behenamidopropyl dimethylamine behenate; behenamidopropyl dimethylamine lactate; behenarnidopropyl ethyldimonium ethosulfate; behenanidopropyl PG-dimonium chloride; behenoyl PG-trimonium chloride; behentrimonium methosulfate; behenyl betaine; behenyl hydroxyethyl imidazoline; benzyl nicotinate; benzyl triethyl ammonium chloride; benzyltrimonium hydrolyzed collagen; betaine; bishydroxyethyl dihydroxypropyl stearaminium chloride; butyl ester of ethylene/MA copolymer butyl ester of PVM/MA copolymer; C12–15 allyl salicylate; C12–16 alcohols; C14–20 isoalkylamidopropylethyldimonium ethosulfate; C18–22 isoalkylamidopropylethyldimonium ethosulfate; calcium pantothenate; calcium pantothenate; canolamidopropyl ethyldimonium ethosulfate; capramide DEA; capryl hydroxyethyl imidazoline; capryloyl collagen amino acids; capryloyl hydrolyzed collagen; capryloyl hydrolyzed keratin; capryloyl keratin amino acids; caprylyl hydroxyethyl imidazoline; carpronium chloride; casein; ceresin; cetethyl morpholinium ethosulfate; cetethyldimonium bromide; cetrimonium methosulfate; cetrimonium saccharinate; cetrimonium tosylate; cetyl betaine; cetyl pyrrolidonylmethyl dimonium chloride; cetylpyridinium chloride; cholecalciferol polypeptide; cocamidopropyl dimethylamine; cocamidopropyl dimethylamine hydrolyzed collagen; cocamidopropyl dimethylamine propionate; cocamidopropyl dimethylaminohydroxypropyl hydrolyzed collagen; cocamidopropyl dimethylammonium C8–16 isoalkylsuccinyl lactoglobulin sulfonate; cocamidopropyl ethyldimonium ethosulfate; cocamidopropyl morpholine; cocamidopropyl morpholine lactate; cocamidopropyl PG-dimonium chloride; cocamidopropyl PG-dimonium chloride phosphate; cocamidopropyldimonium hydroxypropyl hydrolyzed collagen; cocanidopropyltrimonium chloride; cocamine oxide; coco/oleamidopropyl betaine coco-ethyldimonium ethosulfate; coco-hydroxysultaine; coco-morpholine oxide; cocoalkonium chloride; cocodimonium hydroxypropyl hydrolyzed casein; cocodimonium hydroxypropyl hydrolyzed collagen; cocodimonium hydroxypropyl hydrolyzed hair keratin; cocodimonium hydroxypropyl hydrolyzed keratin; cocodimonium hydroxypropyl hydrolyzed rice protein; cocodimonium hydroxypropyl hydrolyzed silk; cocodimonium hydroxypropyl hydrolyzed soy protein; cocodimonium hydroxypropyl hydrolyzed wheat protein; cocodimonium hydroxypropyl silk amino acids; cocotrimonium chloride; cocoyl benzyl hydroxyethyl imidazolinium chloride; cocoyl hydrolyzed collagen; cocoyl hydrolyzed keratin; cocoyl hydrolyzed soy protein; cocoyl polyglyceryl4 hydroxypropyl dihydroxyethylamine; corn starch/acrylamide/sodium acrylate copolymer; cyclomethicone; cysteine; cystine; DEA-lauraminopropionate; DEA-linoleate; decyl betaine; decylamine oxide; dibehenyl/diarachidyl dimonium chloride; dibehenyl methylamine; dibehenyldimonium chloride; dibehenyldimonium methosulfate; dicaprylidicaprylyl dimoniun chloride dicapryloyl cystine; dicetyldimonium chloride; dicocodimonium chloride; dicocoylethyl hydroxyethylmonium methosulfate; didecyldimonium chloride; diethyl aspartate; diethyl glutamate; diethylaminoethyl PEG-5 laurate; diethylene tricaseinamide; dihydrogenated tallow benzylmonium chloride; dihydrogenated tallow benzylmonium hectorite; dihydrogenated tallow hydroxyethylmonium methosulfate; dihydrogenated tallowamidoethyl hydroxyethylmoniwn chloride; dihydrogenated tallowamidoethyl hydroxyethylmonium methosulfate; dihydrogenated tallowdimonium chloride; dihydrogenated tallowethyl hydroxyethylmonium methosulfate; dihydrogenated tallowoylethyl hydroxyethylmonium methosulfate; dihydroxyethyt C12–15 alkoxypropylamine oxide; dihydroxyethyl cocamine oxide; dihydroxyethyl soya glycinate; dihydroxyethyl stearamnine oxide; dihydroxyethyl stearyl glycinate; dihydroxyethyl tallowamine oxide; dilaureth-4 dimonium chloride; dilauryl acetyl dimonium chloride; dilauryldimonium chloride; dilinoleamidopropyl dimethylamine; dimethicone copolyol; dimethicone propyl PG-betaine; dimethyl aspartic acid; dimethyl behenamine; dimethyl cystinate; dimethyl glutamic acid; dimethyl glutarate; dimethyl lauramine; dimethyl lauramine oleate; dimethyl myristamine; dimethyl palmitamine; dimethyl soyamine; dimethyl stearamine; dioctylamine; dioctyldodecyl dodecanedioate; dioleoyl edthp-monium methosulfate; dioleyl edthp-monium methosulfate; dipaimitoyl cystine; dipalmitoyl hydroxyproline; dipalmitoylethyl hydroxyethylmonium methosulfate; dipalmoylethyl hydroxyethylmonium methosulfate; disodium caproamphodiacetate; disodium capryloamphodiacetate; disodium hydrogenated cottonseed glyceride sulfosuccinate; disodium lauriminodipropionate; disodium lauroamphodiacetate; disodium lauroamphodipropionate; disodium oleamido MIPA-sulfosuccinate; disodium steariminodipropionate; disodium stearoamphodiacetate; disoyadimonium chloride; disteareth-6 dimonium chloride; distearoylethyl hydroxyethylmonium methosulfate; distearyldimonium chloride; ditallowamidoethyl hydroxypropylmonium methosulfate; ditallowdimonium chloride; ditallowethyl hydroxyethypponium methosulfate; ditallowoylethyl hydroxyethylmonium methosulfate; ditridecyldimonium chloride; docosahexaenoic acid; dodecylbenzyltrimonium chloride; dodecylxylylditrimonium chloride; erucalkonium chloride; erucamidopropyl hydroxysultaine; ethyl aspartate; ethyl ester of hydrolyzed animal protein; ethyl ester of hydrolyzed keratin; ethyl ester of hydrolyzed silk; ethyl ester of PVMtMA copolymer; ethyl glutamate; ethyl hydroxymethyl oleyl oxazoline; ethyl PEG-15 cocamine sulfate; ethyl serinate; gelatin/keratin amino acids/lysine hydroxypropyl trimonium chloride; gelatinllysine/polyacrylamide hydroxypropyltrimonium chloride; ginseng hydroxypropyltrimonium chloride; glucosamine HCl; glutamic acid; glutamic acid; glutamine; glyceryl distearate; glyceryl lanolate; glycine; glycol oleate; glycol ricinoleate; guar hydroxypropyltrimonium chloride; hair keratin amino acids; hexadimethrine chloride; hexyl nicotinate; hinokitiol; histidine; hyaluronic acid; hydrogenated lanolin; hydrogenated tallowalkonium chloride; hydrogenated tallowamine oxide; hydrogenated tallowtrimonium chloride; hydrolyzed albumen; hydrolyzed casein; hydrolyzed collagen; hydrolyzed corn protein; hydrolyzed elastin; hydrolyzed hair keratin; hydrolyzed human placental protein; hydrolyzed keratin; hydrolyzed lupine protein; hydrolyzed milk protein; hydrolyzed oat protein; hydrolyzed oats; hydrolyzed pea protein; hydrolyzed placental protein; hydrolyzed potato protein; hydrolyzed rice bran protein; hydrolyzed rice protein; hydrolyzed senrun protein; hydrolyzed silk; hydrolyzed soy protein; hydrolyzed spinal protein; hydrolyzed sweet almond protein; hydrolyzed vegetable protein; hydrolyzed wheat protein; hydrolyzed yeast protein; hydrolyzed zein; hydroxycetyl hydroxyethyl dimonium chloride; hydroxyethyl cetyldimonium chloride; hydroxyethyl cetyldimonium phosphate; hydroxyethyl stearamide-mipa; hydroxylated lanolin; hydroxyproline; hydroxypropyl biscetearyldimonium chloride; hydroxypropyl bisisostearamidopropyldimonium chloride; hydroxypropyl bisoleyldimonium chloride; hydroxypropyl bisstearyldimonium chloride; hydroxypropyl guar; hydroxypropyl guar hydroxypropyltrimonium chloride; hydroxypropyltrimonium amylopectin/glycerin crosspolymer, hydroxypropyltrimonium gelatin; hydroxypropyltrimonium hydrolyzed casein; hydroxypropyltrimonium hydrolyzed collagen; hydroxypropyltrimonium hydrolyzed keratin; hydroxypropyltrimonium hydrolyzed rice bran protein; hydroxypropyltrimonium hydrolyzed silk; hydroxypropyltrimoniun hydrolyzed soy protein; hydroxypropyltrimonium hydrolyzed vegetable protein; hydroxypropyltrimonium hydrolyzed wheat protein; hydroxystearamnide MEA; hydroxystearamidopropyl triinonium chloride; hydroxystearamidopropyl trimonium methosulfate; hydroxystearyl methylglucamine; inositol; isobutylated lanolin oil; isodecyl isononanoate; isodecyl salicylate; isoleucine; isononamidopropyl ethyldimonium ethosulfate; isononyl isononanoate; isopropyl ester of PVM/MA copolymer; isopropyl lanolate; isopropyl palmitate; isostearamide DEA; isostearamide MEA; isostearamide MIPA; isostearamidopropyl betaine; isostearamidopropyl dimethylamine; isostearamidopropyl dimethylamine gluconate; isostearamidopropyl dimethylamine glycolate; isostearamidopropyl dimethylamine lactate; isostearamidopropyl epoxypropyl dimonium chloride; isostearamidopropyl ethyldimonium ethosulfate; isostearamidopropyl ethylmorpholinium ethosulfate; isostearamidopropyl laurylacetodimonium chloride; isostearamidopropyl morpholine; isostearamidopropyl morpholine lactate; isostearamidopropyl PG-dimonium chloride; isostearaminopropalkonium chloride; isostearoyl hydrolyzed collagen; isostearoyl PG-trimonium chloride; isostearyl benzylimidonium chloride; isostearyl diglyceryl succinate; isostearyl ethyldimonium chloride; isostearyl ethylimidoniun ethosulfate; isostearyl hydroxyethyl imidazoline; keratin amino acids; lactamide MEA; lactamidopropyl trimoniun chloride; lactoglobulin; lactoyl methylsilanol elastinate; lanolin; lanolin alcohol; lanolin cera; lanolin linoleate; lanolin ricinoleate; lanosterol; lapyrium chloride; lauramide DEA; lauramide MEA; lauramide MIPA; lauamidopropyl acetamidodimonium chloride; lauramidopropyl betaine; lauramidopropyl dimethylamine; lauramidopropyl dimethylamine propionate; lauramidopropyl PG-dimonium chloride; lauramidopropylamine oxide; lauramine; lauramine oxide; lauraminopropionic acid; laurdimnonium chloride; laurdimonium hydroxypropyl hydrolyzed soy protein; laurdimonium hydroxypropyl hydrolyzed wheat protein; lauroyl collagen amino acids; lauroyl hydrolyzed collagen; lauroyl PG-trimonium chloride; lauroyl sarcosine; laurtrimonium bromide; laurtrimonium trichlorophenoxide; lauryl aminopropylglycine; lauryl betaine; lauryl diethylenediaminoglycine; lauryl dimethylamine cyclocarboxypropyloleate; lauryl glycol; lauryl hydroxyethyl imidazoline; lauryl isoquinolinium bromide; lauryl isoquinolinium saccharinate; lauryl methyl gluceth-10 hydroxypropyldimonium chloride; lauryl myristate; lauryl palritate; lauryl sultaine; lauryldimonium hydroxypropyl hydrolyzed casein; lauryldimonium hydroxypropyl hydrolyzed collagen; lauryldimonium hydroxypropyl Imhydrolyzed keratin; lauryldimonium hydroxypropyl hydrolyzed silk; lauryldimonium hydroxypropyl hydrolyzed soy protein; lauryldimonium hydroxypropyl hydrolyzed wheat protein; laurylpyridinium chloride; lecithin; lecithinamide DEA; leucine; linoteamide; linoearide DEA; linoleamide MEA; linoleamide MIPA; linoleamidopropalkonium chloride; linoleamidopropyl dimethylamine; linoleamidopropyl dimethylamine dimer dilinoleate; linoleamidopropyl dimethylamine lactate; linoleamidopropyl ethyldimonium ethosulfate; linoleamidopropyl PG-dimonium chloride phosphate; linoleic acid; linolenic acid; lysine; lysine; lysine PCA; methacryloyl ethyl betaine/acrylates copolymer; methenammonium chloride; methicone; methionine; methyl aspartic acid; methyl glutamic acid; methyl hydroxycetyl glucaminium lactate; methyl hydroxymethyl oleyl oxazoline; methylbenzethonium chloride; methylenebis tallow acetamidodimonium chloride; methylsilanol acetylmethionate; methylsilanol acetyltyrosine; methylsilanol elastinate; methylsilanol hydroxyproline; methylsilanol hydroxyproline aspartate; methylsilanol mannuronate; milk amino acids; minkamidopropalkoniumr chloride; minkamidopropyl dimethylamine; minkamidopropyl ethyldimonium ethosulfate; monosaccharide lactate condensate; montan acid wax; montan cera; myristamide DEA; myristamide MEA; myristamide MIPA; myristamidopropyl betaine; myristamidopropyl dimethylamine; myristamidopropylamine oxide; myristamine oxide; myristaminopropionic acid; myristoyl hydrolyzed collagen; myristoyl sarcosine; myristyl betaine; myristyl hydroxyethyl imidazoline; niacin; norvaline; norvaline; norvaline; octylacrylamide/acrylates/butylaminoethyl methacrylate copolymer; octyldecyl trimonium chloride; octyldodecyltrimoniun chloride; oleamide DEA; oleamide MEA; oleamide MIPA; oleamidopropyl betaine; oleamidopropyl dimethylamine; oleamidopropyl dimethylamine glycolate; oleamidopropyl dimethylamine hydrolyzed collagen; oleamidopropyl dimethylamine lactate; oleamidopropyl dimethylamine propionate; oleamidopropyl ethyldimonium ethosulfate; oleamidopropyl hydroxysultaine; oleamidopropyl PG-dimonium chloride; oleamidopropylamine oxide; oleamidopropyldimonium hydroxypropyl hydrolyzed collagen; oleamine; oleamine bishydroxypropyltrimonium chloride; oleamine oxide; oleoyl hydrolyzed collagen; oleoyl PG-trimonium chloride; oleoyl sarcosine; oleyl betaine; oleyl hydroxyethyl imidazoline; oleyl lanolate; olivamidopropyl dimethylamine; olivamidopropyl dimethylamlne lactate; oryzanol; ouricury wax; palm kemelamidopropyl betaine; palmamidopropyl betaine; palmitamide DEA; palmitamide MEA; palmitamidopropyl betaine; palmitamidopropyl diethylamine; palmitamidopropyl dimethylamine; palmitamidopropyl dimethylamine lactate; palmitamidopropyl dimethylamine propionate; palmitamidopropylamine oxide; palmitamine; palmitamine oxide; palmnitoleamidopropyl dimethylamine lactate; palmitoleamidopropyl dimethylamine propionate; palmitoyl collagen amino acids; palmitoyl hydrolyzed collagen; palmitoyl hydrolyzed milk protein; palmitoyl keratin amino acids; palmitoyl PG-trimonium chloride; panthenol; panthenyl ethyl ether; panthenyl ethyl ether acetate; panthenyl hydroxypropyl steardimonium chloride; panthenyl triacetate; pantothenic acid; pantothenic acid polypeptide; parffinum liquidum; PCA ethyl cocoyl arginate; PEG-10 coco-benzonium chloride; PEG-10 coconut oil esters; PEG-10 stearamine; PEG-10 stearyl benzonium chloride; PEG-105 behenyl propylenediamine; PEG-15 cocomonium chloride; PEG-15 cocopolyamine; PEG-15 oleammonium chloride; PEG-15 stearamine; PEG-15 stearmonium chloride; PEG-15 tallow polyamine; PEG-2 coco-benzonium chloride; PEG-2 cocomonium chloride; PEG-2 milk solids; PEG-2 oleammonium chloride; PEG-2 stearamine; PEG-2 stearnonium chloride; PEG-20 tallow ammonium ethosulfate; PEG-25 diethylmonium chloride; PEG-3 lauramine oxide; PEG-3 tallow propylenedimonium dimethosulfate; PEG-5 cocomonium methosulfate; PEG-5 ditridecylmonium chloride; PEG-5 stearamine; PEG-5 stearyl ammonium chloride; PEG-5 stearyl ammonium lactate; PEG-5 tall oil sterol ether; PEG-S tallow benzonium chloride; PEG-50 stearamine; PEG-8 palmitoyl methyl diethonium methosulfate; petrolatum; PG-hydroxyethylcellulose cocodimonium chloride; PG-hydroxyethylcellulose lauryldimonium chloride; PG-hydroxyethylcellulose stearyldimonium chloride; phenyl trimethicone; phenylalanine; phenylalanine; phosphatidylcholine; phthalic anhydride/glycerin/glycidyl decanoate copolymer pix ex carbone; polyacrylamide; polybutylene terephthalate; polyethylacrylate; polyethylene; polymethacrylamidopropyltrimonium chloride; polyquaternium-1; polyquaternium-10; polyquaternium-1; polyquaternium-12; polyquaternium-13; polyquaternium-14; polyquaternium-15; polyquaternium-16; polyquaternium-17; polyquaterniun-18; polyquaternium-19; polyquaternium-2; polyquaternium-20; polyquaternium-22; polyquaternium-24; polyquaternium-27; polyquaternium-28; polyquaternium-29; polyquaternium-30; polyquaterniun-31; polyquaternium-32; polyquaternium-33; polyquaternium-34; polyquaternium-35; polyquaternium-36; polyquaternium-37; polyquaternium-39; polyquaternium-4; polyquaternium-42; polyquaternium-5; polyquaternium-6; polyquaternium-7; polyquaternium-8; polyquaternium-9; polysilicone-7; polyvinyl acetate; polyvinyl butyral; polyvinyl imidazolinium acetate; polyvinyl methyl ether; potassium caseinate; potassium cocoyl hydrolyzed casein; potassium cocoyl hydrolyzed collagen; potassium cocoyl hydrolyzed keratin; potassium cocoyl hydrolyzed rice bran protein; potassium cocoyl hydrolyzed rice protein; potassium cocoyl hydrolyzed silk; potassium cocoyl hydrolyzed soy protein; potassium cocoyl hydrolyzed wheat protein; potassium lauroyl collagen amino acids; potassium lauroyl hydrolyzed collagen; potassium lauroyl hydrolyzed soy protein; potassium lauroyl wheat amino acids; potassium lauryl hydroxypropyl sulfonate; potassium myristoyl hydrolyzed collagen; potassium oleoyl hydrolyzed collagen; potassium stearoyl hydrolyzed collagen; potassium tallate; potassium undecylenoyl hydrolyzed collagen; PPG-12-buteth-16; PPG-14 butyl ether; PPG-15 butyl ether; PPG-15-buteth-20; PPG-16 butyl ether; PPG-18 butyl ether; PPG-2-buteth-3; PPG-20 methyl glucose ether; PPG-20-buteth-30; PPG-22 butyl ether; PPG-24-buteth-27; PPG-25 diethylmonium chloride; PPG-26-buteth-26; PPG-28-buteth-35; PPG-3 tallow aminopropylamine; PPG-3-buteth-5; PPG-30 butyl ether; PPG-33 butyl ether; PPG-33-buteth45; PPG-4 butyl ether; PPG-40 butyl ether; PPG-40 diethylmonium chloride; PPG-5 butyl ether; PPG-5-buteth-7; PPG-53 butyl ether; PPG-7-buteth-10; PPG-9 butyl ether; PPG-9 diethylmonium chloride; PPG-9-buteth-12; proline;

proline; propyltrimonium hydrolyzed collagen; propyltrimonium hydrolyzed soy protein; propyltrimonium hydrolyzed wheat protein; PVM/MA copolymer; PVP/ dimethylaminoethylnethacrylate copolymer; PVP/eicosene copolymer; PVP/hexadecene copolymer; PVP/VAlitaconic acid copolymer; PVP/VA/vinyl propionate copolymer; PVP/ va copolymer; pyridoxine; pyridoxine dicaprylate; pyridoxine dilaurate; pyridoxine dioctenoate; pyridoxine dipalmitate; pyridoxine HCl; pyridoxine tripalmitate; quaternium-1; quaternium-14; quaternium-16; quaternium-18; quaternium-18 methosulfate; quaternium-22; quaternium-24; quaternium-26; quaternium-27; quaterniwn-30; quaternium-33; quaternium-43; quaternium-45; quatenuum-51; quaternium-52; quaternium-53; quaternium-56; quaternium-60; quaternium-61; quaternium-62; quaternium-63; quaternium-70; quaternium-71; quaternium-72; quaternium-73; quaternium-75; quaternium-76 hydrolyzed collagen; quaternium-77; quaternium-78; quaternium-79 hydrolyzed collagen; quaternium-79 hydrolyzed keratin; quaternium-79 hydrolyzed milk protein; quaternium-79 hydrolyzed silk; quaternium-79 hydrolyzed soy protein; quaternium-79 hydrolyzed wheat protein; quaternium-8; quaternium-80; quaternium-81; quaternium-82; quaternium-83; quaternium-84; quaternium-85; rapeseedamidopropyl benzyldimonium chloride; rapeseedamidopropyl epoxypropyl dimonium chloride; rapeseedamidopropyl ethyldimonium ethosulfate; resorcinol acetate; ricinoleamide DEA; ricinoleamide MEA; ricinoleamide MIPA; ricinoleamidopropyl betaine; ricinoleamidopropyl dimethylamine; ricinoleamidopropyl dimethylamine lactate; ricinoleamidopropyl ethyldimonium ethosulfate; ricinoleamidopropyltrimonium chloride; ricinoleamidopropyltrimonium methosulfate; safflowerarnidopropyl ethyldimonium ethosulfate; serica; sericin; serine; silicone quaternium-1; silicone quaternium-2; silicone quaternium-3; silicone quaternium-4; silicone quaternium-5; silicone quaternium-6; silicone quaternium-7; silicone quaternium-8; silicone quaternium-9; sine adipe lac; sodium/TEA-lauroyl collagen amino acids; sodium/TEA-lauroyl hydrolyzed collagen; sodium/TEA-lauroyl hydrolyzed keratin; sodium/TEA-lauroyl keratin amino acids; sodium/TEA-undecylenoyl collagen amino acids; sodium/ TEA-undecylenoyl hydrolyzed collagen; sodium acrylate/ vinyl alcohol copolymer; sodiun carrageenan; sodium caseinate; sodium chondroitin sulfate; sodium cocoyl collagen amino acids; sodium cocoyl hydrolyzed collagen; sodium cocoyl hydrolyzed keratin; sodium cocoyl hydrolyzed rice protein; sodium cocoyl hydrolyzed soy protein; sodium isethionate; sodium lauraminopropionate; sodium lauriminodipropionate; sodium lauroamphohydroxypropylsulfonate; sodium lauroamphopropionate; sodium lauroyl collagen amino acids; sodium lauroyl glutamate; sodium lauroyl hydrolyzed collagen; sodium lauroyl hydrolyzed silk; sodium lauroyl isethionate; sodium lauroyl sarcosinate; sodium lauroyl taurate; sodium lauroyl wheat amino acids; sodium methyl oleoyl taurate; sodium myristoamphoacetate; sodium myristoyl hydrolyzed collagen; sodium myristoyl isethionate; sodium myristoyl sarcosinate; sodium oleoamphoacetate; sodium oleoamphopropionate; sodium oleoyl hydrolyzed collagen; sodium oleoyl isethionate; sodium PCA; sodium PCA; sodium soya hydrolyzed collagen; sodium stearoamphoacetate; sodium stearoyl hydrolyzed collagen; sodium tallamphopropionate; sodium urocanate; soluble collagen; soy dihydroxypropyldimonium polyglucose; soyaethyl morpholinium ethosulfate; soyamidopropalkonium chloride; soyamidopropyl ethyldimonium ethosulfate; soyamine; soydimonium hydroxypropyl hydrolyzed wheat protein; soyethyldimonium ethosulfate; soytrimonium chloride; squalene; starch diethylaminoethyl ether; steapyrium chloride; stearamide DEA; stearamide MEA; stearamide MEA-stearate; stearamide MIPA; stearamidoethyl diethanolamine; stearamidoethyl diethylamine; stearamidoethyl diethylamine phosphate; stearamidoethyl ethanolamine; stearamidoethyl ethanolamine phosphate; stearamidopropalkonium chloride; stearamidopropyl betaine; stearamidopropyl cetearyl dimonium tosylate; stearamidopropyl dimethylamine; stearamidopropyl dimethylamine lactate; stearamidopropyl ethyldimonium ethosulfate; stearamidopropyl morpholine; stearamidopropyl morpholine lactate; stearamidopropyl PG-dimonium chloride phosphate; stearamidopropyl pyrrolidonylmethyl dimonium chloride; stearamidopropyl trimonium methosulfate; steararnidopropylamine oxide; stearaunine; stearamine oxide; steardimonium hydroxypropyl hydrolyzed casein; steardimonium hydroxypropyl hydrolyzed collagen; steardimoniun hydroxypropyl hydrolyzed keratin; steardimonium hydroxypropyl hydrolyzed rice protein; steardimonium hydroxypropyl hydrolyzed silk; steardimonium hydroxypropyl hydrolyzed vegetable protein; steardimonium hydroxypropyl hydrolyzed wheat protein; stearoyl PG-trimonium chloride; stearoyl sarcosine; steartrimonium hydroxyethyl hydrolyzed collagen; steartrimonium methosulfate; stearyl betaine; stearyl hydroxyethyl irnidazoline; stearyl hydroxyethylimidonium chloride; stearyl octyldimonium chloride; stearyl octyldimonium methosulfate; stearylvinyl ether/MA copolymer; sucrose cocoate; sulfur; synthetic wax; tall oil benzyl hydroxyethyl imidazolinium chloride; tall oil hydroxyethyl imidazoline; tallamide DEA; tallow trihydroxyethylammonium acetate; tallowalkonium chloride; tallowamide DEA; tallowamide MEA; tallowamidopropylamine oxide; tallowamine oxide; tallowdimonium propyltrimonium dichloride; tallowtrimonium chloride; TEA-abietoyl hydrolyzed collagen; TEAcocoyl hydrolyzed collagen; TEA-cocoyl hydrolyzed soy protein; TEA-lauraminopropionate; TEA-lauroyl keratin amino acids; TEA-lauroyl sarcosinate; TEA-myristaminopropionate; TEA-myristoyl hydrolyzed collagen; TEA-oleoyl hydrolyzed collagen; TEA-oleoyl sarcosinate; TEA-palm kernel sarcosinate; TEA-undecylenoyl hydrolyzed collagen; tetrabutyl ammonium bromide; thenoyl methionate; threonine; threonine; tricetylmonium chloride; tridecyl salicylate; triethonium hydrolyzed collagen ethosulfate; trilaurylamine; trimethylsilylamodimethicone; trioctanoin; tripaba panthenol; trisodium lauroampho PG-acetate phosphate chloride; tristearyl PG-phosphate dimonium chloride; triundecanoin; tryptophan; tryptophan; tyrosine; undecylenamide DEA; undecylenamide MEA; undecylenamidopropyltrimonium methosulfate; undecylenoyl collagen amino acids; undecylenoyl hydrolyzed collagen; undecylenyl alcohol; urea; VA/crotonates/vinyl neodecanoate copolymer; va/crotonates copolymer; valine; wheat germamidopropalkonium chloride; wheat gernamidopropyl epoxypropyldirnoniurn chloride; wheat germamidopropylamine oxide; wheat germamidopropyldimonium hydroxypropyl hydrolyzed wheat protein; wheatgermamidopropyl dimethylamine hydrolyzed collagen; wheatgermamidopropyl dimethylamine hydrolyzed wheat protein; wheatgermamidopropyl ethyldimonium ethosulfate; *zea mays*; zinc hydrolyzed collagen.

In particular, cationic and amphoteric fatty acids such as polyquaternium compounds are useful as hair conditioners or fixatives. Examples of cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammnonium salts, and vinyl quaternary ammonium monomers having cyclic cationic nitrogen-containing rings such as pyridinium, imidazolium, and quaternized pyrrolidine, e.g., alkyl vinyl imidazolium, alkyl vinyl pyridinium, and alkyl vinyl pyrrolidine salts. The alkyl portions of these, monomers are preferably lower alkyls such as the C1–C3 alkyls, more preferably C1 and C2 alkyls.

Other compounds useful as bulking agents include: octylacrylamide/acrylates/butylaminoethyl methacrylate copolymer (a polymer of N-tert-octyl acrylamide, methyl methacrylate, hydroxypropyl methacrylate, acrylic acid and t-butyl aminoethyl methacrylate).

Other cationic conditioning compounds include quaternary nitrogen derivatives of cellulose ethers, homopolymers of dimethyldiallyl-ammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,θ-bis-(triethanolammonium) chloride. The agent can also be a hair fixative as described above. Hair fixatives are agents which impart hair-holding or style-retention properties to hair. Film formners, such as gums and polymeric substances, can also be used as hair fixatives. Examples of hair fixative agents including some film formers which are suitable hair fixatives include: Acrylamide/Ammonium Acrylate Copolymer; Acrylamides/DMAPA Acrylates/Wethoxy PEG Methacrylate Copolymer; Acrylamidopropyltrimonium ChloridelAcrylamide Copolymer, Acrylamidopropyltrimoniuin Chloride/Acrylates Copolymer; Acrylates/Acetoacetoxyethyl Methacrylate Copolymer; Acrylates/Acrylamide Copolymer; Acrylates/Amnmonium Methacrylate Copolymer; Acrylates Copolymer; Acrylates/Octylacrylarnide Copolymer; Acrylates/PVP Copolymer, Acrylates/VA Copolymer; Adipic Acid/Diethylenetriamine Copolymer; Adipic Acid/Dimethylaminohydroxypropyl Diethylenetriamine Copolymer; Adipic Acid/Epoxypropyl Diethylenetriamine Copolymer; Adipic Acid/Isophthalic Acid/Neopentyl Glycol/Frimethylolpropane Copolymer; Allyl StearateVA Copolymer; Aminoethylacrylate Phosphate/Acrylates Copolymer; Ammonium VA/Acrylates Copolymer; AMP-Acrylates/Diacetoneacrylamide Copolymer; AMP-25 Acrylates/Dimethylaminoethylmethacrylate Copolymer; AMPD-Acrylates/Diacetoneacrylamide Copolymer; Butylated PVP; Butyl Ester of Ethylene/MA Copolymer; Butyl Ester of PVM/MA Copolymer, Calcium/Sodium PVMIMA Copolymer; Corn Starch/Acrylamide/Sodium Acrylate Copolymer; Diethylene Glycolamine/Epichiorohydrin/Piperazine Copolymer; Ethyl Ester of PVM/MA Copolymer, Isobutylene/MA Copolymer; Isopropyl Ester of PVM/MA Copolymer; Karaya (Sterculia Urens) Gum; Lauryl Methacrylate/Glycol Dimethacrylate Copolymer; Methacryloyl Ethyl Betaine/Acrylates Copolymer; Octylacrylamide/Acrylates/Butylaminoethyl Methacrylate Copolymer; PEG8/SMDI Copolymer; Polyacrylamide; Polybeta-alanine/Glutaric Acid Crosspolymer; Polybutylene Terephthalate; Polyethylacrylate; Polyethylene Terephthalate; Polyperfluoroperhydrophenanthrene; Polyquaternium-1; Polyquaternium-2; Polyquaternium-4; Polyquaternium-5; Polyquaternium-6; Polyquaternium-7; Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-17; Polyquaternium-18; Polyquaternium-19; Polyquaternium-20; Polyquaternium-22; Polyquaternium-24; Polyquaternium-27; Polyquaternium-28; Polyquaternium-29; Polyquaternium-30; Polyquaternium-31; Polyquaternium-32; Polyquaternium-33; Polyquaternium-34; Polyquaternium-35; Polyquaternium-36; Polyquaternium-37; Polyquaternium-39; Polyquaternium-45; Polyquaternium-46; Polyquaternium-47; Polysilicone-9; Polyvinyl Acetate; Polyvinyl Butyral; Polyvinylcaprolactam; Polyvinylfonnmnide; Polyvinyl Imidazoliniun Acetate; Polyvinyl kilt Methyl Ether; PPG-12/SMD1 Copolymer PPG-51/SMDI Copolymer; PVM/MA Copolymer; PVP; PVP/Acrylates/Lauryl Methacrylate Copolymer; PVP/Dimethylarrinoethylmethacrylate Copolymer; PVP/DMAPA Acrylates Copolymer; PVP/Hexadecene Copolymer; PVP/VA Copolymer; PVPfVAlltaconic Acid Copolymer, PVP/VA/Vinyl Propionate Copolymer; PVP/Vinyl Caprolactam/DMAPA Acrylates Copolymer; Rosin Acrylate; Shellac; Sodium Polyacrylate; Terephthalic Acid/Isophthalic Acid/Sodium Isophthalic Acid Sulfonate/Glycol Copolymer; VA/Crotonates Copolymer; VA/Crotonates/Methacryloxybenzophenone-1 Copolymer; VA/Crotonates/Vinyl Neodecanoate Copolymer; VA/Crotonates/Vinyl Propionate Copolymer; VA/DBM Copolymer; VA/Vinyl Butyl Benzoate/Crotonates Copolymer; Vinyl Caprolactam/PVP/Dimethylaminoethyl Methacrylate Copolymer; Yeast Palmitate.

Other compounds which are useful as hair fixatives include shellac, polyvinylpyrrolidone-ethyl methacrylate-methacrylic acid tarpolymer, vinyl acetate-crotonic acid copolymer, vinyl acetate-crotonic acid-vinyl neodeconate tarpolymer, poly(vinylpyrrolidone-ethylmethacrylate) methacrylic acid copolymer, vinyl methyl ether-maleic anhydride copolymer, octylacrylamide-acrylate-butylaminoethyl-methacrylate copolymer, and poly(vinylpyrrolidone-dimethylaminoethyl-methacrylate) copolymer and derivatives; thioglycollic acid and its salts and esters; potassium or sodium hydroxide; lithium hydroxide; calcium hydroxide; quinine and its salts; resorcinol; 1,3-bis(hydroxymethyl) imidazolidine-2-thione; etidronic acid and its salts (1-hydroxy-ethylidenediphosphonic acid and its salts).

Examples of anti-foaming agents which are useful as bulking agents include: bisphenylhexamethicone; dimethicone; dimethiconol; hexamethyldisiloxane; hexyl alcohol; isopropyl alcohol; petroleum distillates; phenethyl disiloxane; phenyl trimethicone; polysilicone-7; propyl alcohol; silica dimethyl silylate; silica silylate; tetramethyl decynediol; trimethylsiloxysilicate.

The agent also can be a tissue sealant. Tissue sealants are those used in wound healing to mechanically seal wounds. The use of transglutaminase to covalently attach such materials would add mechanical and adhesive strength to this sealant. Such tissue sealants are composed typically of fibrinogen, collagen, hyaluronic acid, synthetic peptides and the like. They also can be polyglutamines, polylysines, or polymers of both glutamine and lysine, corneocyte proteins and the like.

The agents also can be insect repellants. A widely used insect repellant is N-N-diethyl-3-methylbenzamide. Pheromones are also useful as insect repellants.

The agent also may be cultured cells and cultured body tissues used for wound healing, cartilage replacement, corneal replacements and other like surgical procedures.

As mentioned earlier, the agent can also be a film forming agent. A film forming agent is an agent which produces a continuous film on skin, hair or nails upon application. Film forming agents are useful in wound healing or in some cases as hair fixatives, as described above. Examples of film forming agents include: acetyl tributyl citrate; acetyl triethyl citrate; acetyl trioctyl citrate; acrylamide/sodium acrylate copolymer; acrylamides/acrylates/DMAPA/methoxy PEG methacrylate copolymer; acrylamides copolymer; acrylamidopropyltrimonium chloride/acrylates copolymer; acrylates/acetoacetoxyethyl methacrylate copolymer; acrylates/acrylamide copolymer; acrylates/ammonium methacrylate copolymer; acrylates/C10–30 alkyl acrylate crosspolymer; acrylates/diacetoneacrylamide copolymer; acrylates/octylacrylamide copolymer; acrylates/PVP copolymer; acrylates/steareth-50 acrylate copolymer; acrylates/VA copolymer; acrylates/VA crosspolymer; acrylates copolymer; acrylic acid/acrylonitrogens copolymer; adipic acid/diethylene glycol/glycerin crosspolymer, adipic acid/diethylenetriamine copolymer; adipic acid/dimethylaminohydroxypropyl diethylenetriamine copolymer; adipic acid/epoxypropyl diethylenetriamine copolymer; adipic acid/isophthalic acid/neopentyl glycolltrimethylolpropane; copolymer; albumen; allyl stearate/VA copolymer; aminoethylacrylate phosphate/acrylates copolymer; ammonium acrylateslacrylonitrogens copolymer; ammonium acrylates copolymer; ammonium alginate; ammonium VA/acrylates copolymer; amp-acrylates/diacetoneacrylamide copolymer; amp-acrylates copolymer; ampd-acrylates/diacetoneacrylamide copolymer; bayberry wax; behenyl/isostearyl beeswax; benzoic acid/phthalic anhydride/pentaerythritol/neopentyl glycol/palmitic acid copolymer; butadienelacrylonitrile copolymer; butoxy chitosan; butyl benzoic acid/phthalic anhydride/trimethylolethane copolymer; butyl benzyl phthalate; butyl ester of ethylene/MA copolymer; butyl ester of PVM/MA copolymer; butyl phthalyl butyl glycolate; butylated polyoxyrnethylene urea; butylated PVP; calcium/sodium PVM/MA copolymer; calcium carrageenan; camphor; candelilla cera; carboxymethyl chitosan succinamide; carboxymethyl hydroxyethylcellulose; carnauba; cellulose acetate; cellulose acetate butyrate; cellulose acetate propionate; cellulose gum; cera alba; ceratonia siliqua; cetyl hydroxyethylcellulose; chitosan succinamide; collodion; colophoniurn; copaifera officinalis; copal; corn starchlacrylamide/sodium acrylate copolymer; croscarmellose; cyanopsis tetragonalba; desamido collagen; dibutyl adipate; dibutyl lauroyl glutarnide; dibutyl phthalate; dibutyl sebacate; dicapryl adipate; dicetyl adipate; diethyl phthalate; diethylene glycolamine/epichlorohydrin/piperazine copolymer; diglycol/chdm/isophthalates/sip copolymer; dilinoleic acid/ethylenediamine copolymer; dimethiconelmercaptopropyl methicone copolymer; dimethicone/sodium PG-propyldimethicone thiosulfate copolymer; dimethyl phthalate; dioctyl adipate; dioctyl phthalate; dioctyl sebacate; dioctyl succinate; dmapa acrylates/acrylic acid/acrylonitrogens copolymer; dmihf; dodecanedioic acid/cetearyl alcohol/glycol copolymer; ethyl cyanoacrylate; ethyl ester of PVM/MA copolyrner, ethyl tosylamide; ethylcellulose; ethylene/acrylic acidWA copolymer; ethylene/acrylic acid copolyrner; ethylene/calcium acrylate copolyrner; ethylene/MA copolymer; ethylene/magnesium acrylate copolymer; ethylene/propylene copolymer; ethylene/sodium acrylate copolymer; ethylene/VA copolymer; ethylene/zinc acrylate copolymer; flexible collodion; gellan gum; glyceryl alginate; glyceryl hydrogenated rosinate; glyceryl polyacrylate; glyceryl rosinate; glycosaminoglycans; guar hydroxypropyltrimonium chloride; gutta percha; hydrogenated styrene/butadiene copolymer; hydrogenated styrene/methyl styrene/indene copolymer; ydrolyzed collagen; hydrolyzed elastin; hydrolyzed keratin; hydroxybutyl methylcellulose; hydroxyethyl ethylcellulose; hydroxyethylcellulose; hydroxylated lanolin; hydroxypropyl guar; hydroxypropyl methylcellulose; hydroxypropylcellulose; isobutylene/sodium maleate copolymer; isopropyl ester of PVM/MA copolymer; lanolin cera; lauryl acrylate/VA copolymer, lithium oxidized polyethylene; maltodextrin; melamine/formaldehyde resin; methacryloyl ethyl betaine/acrylates copolymer; methyl hydrogenated rosinate; methyl methacrylate crosspolymer; methyl rosinate; mustela; natto gum; nitrocellulose; nonoxynyl hydroxyethylcellulose; oat beta glucan; octylacrylamide/acrylatestbutylaminoethyl methacrylate copolymer; oleoyl hydrolyzed collagen; ouricury wax; oxidized polypropylene; PEG-8/SMDI copolymer; PEG-crosspolymer; pentaerythrityl hydrogenated rosinate; pentaerythrityl rosinate; phthalic anhydride/adipic acid/castor oiltneopentyl glycoV/PEG-3/trimethylolpropane copolymer; phthalic anhydride/benzoic acid/trimethylolpropane copolymer; phthalic anhydridetbutyl benzoic acid/propylene glycol copolymer; phthalic anhydride/glycerin/glycidyl decanoate copolymer; phthalic anhydride/trimellitic anhydride/glycols copolymer; polyacrylamide; polyacrylamidomethylpropane sulfonic acid; polyacrylic acid; polybutylene terephthalate; polychlorotrifluoroethylene; polydimethylaminoethyl methacrylate; polyethylacrylate; polyethylene; polyethylene terephthalate; polyglucuronic acid; polyglycerylmethacrylate; polyisobutene; polymethacrylamidopropyltrimonium chloride; polymethyl acrylate; polymethyl methacrylate; polyoxyisobutylene/methylene urea copolymer; polypropylene; Polyquaterium-1; Polyquaternium-10; Polyquaternium-11; Polyquaternium-12; Polyquaternium-13; Polyquaternium-14; Polyquaternium-15; Polyquaternium-16; Polyquaternium-17; Polyquaternium-18; Polyquaternium-19; Polyquaternium-2; Polyquaternium-20; Polyquaternium-22; Polyquaternium-24; Polyquaternium-27; Polyquaternium-28; Polyquaternium-29; Polyquaternium-30; Polyquaternium-31; Polyquaternium-32; Polyquaternium-33; Polyquaternium-34; Polyquaternium-35; Polyquaternium-36; Polyquaternium-37; Polyquaternium-39; Polyquaternium-4; Polyquaternium-42; Polyquaternium-5; Polyquaternium-6; Polyquaternium-7; Polyquaternium-8; Polyquaternium-9; Polysilicone-6; polystyrene; polyurethane; polyvinyl acetate; polyvinyl alcohol; polyvinyl butyral; polyvinyl imidazolinium acetate; polyvinyl laurate; polyvinyl methyl ether; potassium acetate; potassium carrageenan; potassium hyaluronate; PPG-26/TD1 copolymer; PPG-51/SMDI copolymer; procollagen; propylene glycol diundecanoate; PVM/MA copolymer; PVP; PVP/decene copolymer; PVP/dimethylaminoethylmethacrylate copolymer; PVP/eicosene copolymer; PVP/hexadecene copolymer; PVPNA/itaconic acid copolymer; PVPJVA/vinyl propionate copolymer; PVP/va copolymer; rosin acrylate; rosin hydrolyzed collagen; rubber latex; shellac; shellac cera; sodium acrylate/vinyl alcohol copolymer; sodium carrageenan; sodium dvb/acrylates copolymer; sodium polyacrylate starch; sodium polymethacrylate; sodium polystyrene sulfonate; sodium PVM/MA/decadiene crosspolymer; sodium styrene/acrylamide copolymer; sodium styrene/acrylates copolymer; sodium tauride acrylates/acrylic acid/acrylonitrogens copolymer; soluble collagen; starch/acrylates/acrylaride copolymer; starch diethylaminocthyl ether, steareth-10 allyl ether/acrylates copolymer; stearylvinyl ether/MA copolymer; styrax benzoin; styrax benzoin; styrene/acrylates/acrylonitrile copolymer; styrene/acrylates/ ammonium methacrylate copolymer; styrene/allyl benzoate copolymer; styrene/MA copolymer; styrene/pvp copolymer; sucrose acetate isobutyrate; sucrose benzoate; sucrose benzoate/sucrose acetate isobutyrate/butyl benzyl phthalate/methyl methacrylate copolymer; sucrose benzoate/sucrose acetate isobutyrate/butyl benzyl phthalate; copolymer, sucrose benzoate/sucrose acetate isobutyrate copolymer; TEA-acrylates/acrylonitrogens copolymer; tosylamide/epoxy resin; tosylamide/formaldehyde resin; triacetin; tributyl citrate; tributylcresylbutane; tricetyl phosphate; tricontanyl PVP; trimethylpentanediol/isophthalic acid/trimellitic anhydride copolymer; tromethamine acrylates/acrylonitrogens copolymer; VA/butyl maleate/isobornyl acrylate copolymer, VA/crotonates/methacryloxybenzophenone-1 copolymer, VA/crotonates/vinyl neodecanoate copolymer; VA/crotonates/vinyl propionate copolymer; VA/crotonates copolymer; VA/dbm copolymer; VA/isobutyl maleate/vinyl neodecanoate copolymer; VA/vinyl butyl benzoate/crotonates copolymer; vinyl acetate; vinyl caprolactam/pvp/dimethylaminoethyl methacrylate copolymer.

The agent can also be an anti-nerve gas agent. An anti-nerve gas agent is an agent which counteracts the effects of a nerve gas agent. Examples of anti-nerve gas agents include: organophosphate hydrolases such as phosphotriesterase; pyridostigmine, physostigmine, eptastigmine, pralidoxime-2-chloride (2-PAM); potassium 2,3-butadion monoximate; potassium permanganate; sodium phenolate or sodium cresolate; chlorinated lime and magnesium oxide; chloramines; bentonite; and a mixture of atropine and PAM.

The agent can also be a vitamin including vitamin A, vitamin B, vitamin C, vitamin D, vitamin E, and their provitamin counterparts.

As mentioned above, the agent may be a pharmaceutical agent.

When administered the pharmaceutical agents of the invention are applied in pharmaceutically acceptable amounts and in pharmaceutically acceptable compositions. Such preparations may routinely contain salts, buffering agents, preservatives, compatible carriers and optionally other therapeutic or nontherapeutic ingredients. When used in medicine, the salts should be pharmaceutically acceptable, but nonpharmaceutically acceptable salts may conveniently be used to prepare pharmaceutically acceptable salts thereof and are not excluded from, the scope of the invention.

Examples of categories of pharmaceutical agents include: analgesic; amino acid; antagonist; anti-acne agent; anti-allergic; anti-asthmatic; antibacterial; anticholinergic; anti-fungal; antiglaucoma agent; antihistamine; anti-infective; anti-infective, topical; antito inflammatory; antikeratinizing agent; antimicrobial; antimycotic; antineoplastic, antineutropenic; antiproliferative; antipruritic; antiseborrheic; carbonic anhydrase inhibitor; cholinergic; cholinergic agonist; diagnostic aids; ectoparasiticide; fluorescent agent; glucocorticoid; hair growth stimulant; histamine H2 receptor antagonists; immunizing agent; immunomodulator; immunoregulator; immunostimulant; immunosuppressant; keratolytic; mucosal protective agent; radioactive agents; wound healing agent.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefidane; Dipyrone; Doxpicomine Hydrochloride; Drinidene; Enadoline Hydrochloride; Epirizole; Ergotamine Tartrate; Ethoxazene Hydrochloride; Etofenarnate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen ; Hydromorphone Hydrochloride; Ibufenac; Indoprofen; Ketazocine; Ketorfanol; Ketorolac Tromethamnine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicarn; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Veriloparn Hydrochloride; Volazocine; Xorphanol Mesylate; Xylazine Hydrochloride; Zenazocine Mesylate; Zomepirac Sodium; Zucapsaicin.

Antiacne: Adapalene; Erythromycin Salnacedin; Inocoterone Acetate.

Antiallergic: Amlexanox; Asternizole; Azelastine Hydrochloride; Eclazolast; Minocromil; Nedocromil; Nedocromil Calcium; Nedocromil Sodium; Nivimedone Sodium; Pemirolast Potassium; Pentigetide; Pirquinozol; Poisonoak Extract; Probicromil Calcium; Proxicromil; Repirinast; Tetzazolast Meglunine; Thiazinamium Chloride; Tiacrilast; Tiacrilast Sodium; Tiprinast Meglumine; Tixanox.

Antiasthmatic: Ablukast; Ablukast Sodium; Azelastine Hydrochloride; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Repirinast;

Ritolukast; Sulukast; Tetrazolast Meglumine; Tiaramide Hydrochloride; Tibenelast Sodiumn; Tomelukast; Tranilast; Veriukast; Verofylline; Zarirlukast.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Aziocillin Sodium; Bacampicillin Hydrochloride; Bacitracin; Bacitracin Methylene Disalicylate; Bacitracin Zinc; Bambermycins; Benzoylpas Calcium; Berythromycin ; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassiwn; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefnetazole; Ceftnetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftiaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate, Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodiumr; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifliraldezone; Nifuratel; Nifuratrone; Nifuirdazil; Nifurimide; Nifurpirinol; Nifilrquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosararicin Propionate; Rosaramicin Sodium Phosphate; Rosaramicin Stearate; Rosoxacin; Roxarsone; Roxitbromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetanide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfarnoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anticholinergic: Alverinc Citrate; Anisotropine Methylbromide; Atropine; Atropine Oxide Hydrochloride; Atropine Sulfate; Belladonna; Benapryzine Hydrochloride; Benzetirnide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; Tropicarnide.

Antifungal: Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungirnycin; Griseoflilvin; Hamycin; Isoconazole; Itraconazole; Kalafingin; Ketoconazole; Lomofingin; Lydimycin; Mepartricin; Miconazole; Miconazolc Nitrate; Monensin; Monensin Sodium; Naftifine Hydrochloride; Neomycin Undecylenate; Nifuratel; Nifimrerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefingin; Sulconazole Nitrate; Terbinafine; Terconazole; Thiram; Ticlatone; Tioconazole; Tolciclate; Tolindate; Tolnaftate; Triacetin; Triaftngin; Undecylenic Acid; Viridofulvin; Zinc Undecylenate; Zinoconazole Hydrochloride.

Antiglaucoma agent: Alprenoxime Hydrochloride; Colforsin; Dapiprazole Hydrochloride; Dipivefrin Hydrochloride; Naboctate Hydrochloride; Pilocarpine; Pimabine.

Antihistaminic: Acrivastine; Antazoline Phosphate; Astemizole; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cinnarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; Triprolidine Hydrochloride; Zolamine Hydrochloride.

Anti-infective: Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro).

Anti-infective: topical: Alcohol; Aminacrine Hydrochloride; Benzethonium Chloride: Bithionolate Sodium; Bromchlorenone; Carbainide Peroxide; Cetalkonium Chloride; Cetylpridinium Chloride:Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitroflirazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thirnerosal: Troclosene Potassium.

Anti-inflarnmmatoa: Alclofenac; Alclometasone Dipropionate; Algestone Acetonide; Alpha Amylase; Amcinafal; Arncinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodiumr; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antikeratinizing agent: Doretinel; Linarotene; Pelretin.

Antimicrobial:Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine.

Antimycotic: Amorolfine.

Antineoplastic Acivicin; Aclarubicin; Acodazole Hydrochloride; Acronine; Adozelesin; Aldesleukin; Altretamnine; Ambomycin; Ametantrone Acetate; Aminoglutetimide; Amsacrine; Anastrozole; Anthrarnycin; Asparaginase; Asperlin; Azacitidine; Azetepa; Azotomycin; Batimastat;

Benzodepa; Bicalutamide; Bisantrene Hydrochloride; Bisnafide Dimesylate; Bizelesin; Bleomycin Sulfate; Brequinar Sodium; Bropinmine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsarnitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198 ; Hydroxyurea; Idarubicin Hydrochloride; Ifosfamide; Ilmofosine; Interferon Alfa-2a; Interferon Alfa-2b; Interferon Alfa-nl; Interferon Alfa-n3; Interferon Beta-I a; Interferon Gamma-I b; Iproplatin; Irinotecan Hydrochloride; Lanreotide Acetate; Letrozole; Leuprolide Acetate; Liarowle Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper, Mitotane; Mitoxantrone Hydrochloride; Mycophenolic Acid; Nocodazole; Nogalarnycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Torernifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma, antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutarnide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; cmitefuir, epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilnofosine; ilomastat; irnidazoacridones; imiquimod; immunostimulant peptides; insulin-like growth factor-1 receptor inhibitor; interferon agonists; interferons; interleukins; iobenguane; iododoxorubicin; ipomeanol, 4; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; nmirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted bennamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn;

06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; parnidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverot; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfm; temozolomuide; teniposide; tetrachorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer Supplementary Potentiating Agents: Tricyclic anti-depressant drugs (e.g., imipramine, desipramine, arnitryptyline, clomipramine, trimipramine, doxepin, nortriptyline, protriptyline, amoxapine and maprotiline); non-tricyclic anti-depressant drugs (e.g., sertraline, trazodone and citalopram); Ca antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Antineutropenic: Filgrastim; Lenograstim; Molgramostim; Regramostim; Sargramostim.

Antiproliferative agent: Piritrexirn Isethionate.

Antiprotozoal: Amodiaquine; Azanidazole; Bamnidazole; Carnidazole; Chlortetracycline Bisulfate; Chlortetracycline Hydrochloride; Flubendazole; Flunidazole; Halofuginone Hydrobromide; Imidocarb Hydrochloride; Ipronidazole; Metronidazole; Misonidazole; Moxnidazole; Nitarsone; Partricin; Puromycin; Puromycin Hydrochloride; Ronidazole; Sulnidazole; Tinidazole.

Antipruritic: Cyproheptadine Hydrochloride; Methdilazine; Methdilazine Hydrochloride; Trineprazine Tartrate.

Antipsoriatic: Acitretin; Anthralin; Azaribine; Calcipotriene; Cycloheximide; Enaadrem Phosphate; Etretinate; Liarozole Fumarate; Lonapalene; Tepoxalin.

Carbonic anhydrase inhibitor: Acetazolamide; Acetazolamide Sodium; Dichlorphenamide; Dorzolamide Hydrochloride; Methazolarnide; Sezolamide Hydrochloride.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Diagnostic aid: Aminohippurate Sodium; Anazolene Sodium; Arclofenin; Arginine; Bentiromide; Benzylpenicilloyl Polylysine; Butedronate Tetrasodium; Butilfenin; Coccidioidin; Corticorelin Ovine Triflutate; Corticotropin, Repository; Corticotropin Zinc Hydroxide; Diatrizoate Meglumine; Diatrizoate Sodium; Diatrizoic Acid; Diphtheria Toxin for Schick Test; Disofenin; Edrophonium Chloride; Ethiodized Oil; Etifenin; Exametazirne; Ferristenc; Ferumoxides; Ferumoxsil; Fluorescein; Fluorescein Sodium; Gadobenate Dimeglumine; Gadoteridol; Gadodiamide; Gadopentetate Dimegiumine; Gadoversetamide; Histoplasmin; Impromidine Hydrochloride; Indigotindisulfonate Sodium; Indocyanine Green; Iobenguane Sulfate I 123; Iobenzamic Acid; Iocarnate Meglumine; Iocarmic Acid; Iocetamic Acid; Iodamide; Iodamide Meglumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopanoic Acid; Iopentol; Iophendylate; Iprofenin; Iopronic Acid; Ioprocemic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxaglate Meglumine; Ioxagiate Sodium; Ioxaglic Acid; Ioxilan; Ioxotrizoic Acid; Ipodate Calcium; Ipodate Sodium; Isosulfan Blue; Leukocyte Typing Serun; Lidofenin; Mebrofenin; Meglumine; Metrizamide; Metrizoate Sodium; Metyrapone; Metyrapone Tartrate; Mumps Skin Test Antigen; Pentetic Acid; Propyliodone; Quinaldine Blue; Schick Test Control; Sermorelin Acetate; Sodium Iodide 1123; Sprodiamide; Stannous Pyrophosphate; Stannous Sulfuir Colloid; Succimer; Teriparatide Acetate; Tetrofosmin; Tolbutamide Sodium; Tuberculin; Tyropanoate Sodium; Xylose.

Ectoparasiticide: Nifluridide; Permethrin.

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Corticotropin, Repository; Corticotropin Zinc Hydroxide; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Phosphate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamncinolone Diacetate; Triamcinolone Hexacetonide.

Hair growth stimulant: Minoxidil.

Histamine H2 receptor antagonists: Ranitidine (Zantac); Famotidine (Pepcid); Cimetidine (Tagamet); Nizatidine (Axid).

Immunizing agent: Antirabies Serum; Antivenin (Latrodectus mactans); Antivenin (Micrurus Fulvius); Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; Rho(D) Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Yellow Fever vaccine; Vaccinia Immune Globulin; Varicella-Zoster Immune Globulin.

Immunomodulator: Dimepranol Acedoben; Imiquimod; Interferon Beta-1b; Lisofylline; Mycophenolate Mofetil; Przatide Copper Acetate.

Immnunoregulaor: Azarole; Fanetizole Mesylate; Frentizole; Oxamisole Hydrochloride; Ristianol Phosphate; Thymopentin; Tilomisole.

Immunostimulant: Loxoribine; Teceleukin.

Immunosuppressant: Azathioprine; Azathioprine Sodium; Cyclosporine; Daltroban; Gusperimus Trihydrochloride; Sirolimus; Tacrolimus. Mucolytic: Acetylcysteine; Carbocysteine; Domiodol.

Mucosal Protective agents: Misoprostol (Cytotec).

Radioactive agent: Fibrinogen I 125 ; Fludeoxyglucose F 18 ; Fluorodopa F 18; Insulin I 125; Insulin I 131; Iobenguane I 123; Iodipamide Sodium I 131 ; Iodoantipyrine I 131; Iodocholesterol I 131; Iodohippurate Sodium I 123 ; Iodohippurate Sodium I 125; Iodohippurate Sodium I 131; Iodopyracet I 125 ; Iodopyracet I 131; Iofetamine Hydrochloride I 123; Iomethin I 125 ; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Wound healing agent: Ersofermin.

The invention thus may be used, inter alia, to localize drugs to a tissue such as a wound bed or for localized delivery to a tissue, to hold a drug, insect repellant, bactericide fungicide, growth factors, cytokine, and the like at a particular location to prevent the drug from being flushed away to other body sites where it is not needed, to apply bulking agents and other cosmetic agents to the integuments, such as the skin, hair and nails, to hold sunscreen agents at the surface of the skin for longer periods of time, to hold anti-nerve gas enzymes at the surface of the skin whereby nerve gas can be deactivated, to hold or link chemical agents to the skin which can in turn act as binding sites for other agent or alternatively, as reactive sites for catalytic buildup of multiple alternating layers, to link hydrophobic compounds to the skin, thereby making the skin hydrophobic, to link conditioners to the hair, thereby giving hair the appearance of greater bulk and to link agents to organs or tissues which are to be transplanted.

EXAMPLES

Example 1

Durable Suntan Preparation and Kit

A kit is provided for producing a durable sunscreen. The kit includes as a first component a conjugate of a low molecular weight sunscreen agent and a linking agent. This component is an aqueous solution, pH 6.4 of 50 mM polylysyl-methoxy-2-ethylhexyl-cinnamate, 0.1 v % propylene glycol, 0.5 mM, EDTA, 0.1 wt % BHT, 0.1 wt % potassium sorbate, 0.05 wt % polysorbate 20 and 80 and 1 mM sodium laurylether sulfate. Component 2 of the kit is a calcium chloride activator solution. This is an aqueous solution at about 25 mM calcium chloride. Component 3 of the kit is lyophilized transglutaminase. The lyophilized preparation can contain 10 mg of recombinant tissue transglutaminase in 2% sucrose, 0.1 mM EDTA, and 5 mM glycine buffer, pH 7.2.

Three vials containing the three kit components are opened. About 10 mL of component 1 is added to 10 mg of component 3, and the combination is mixed by swirling. Then this combination is added to about 90 mL of component 1. Finally, about 10 mL of component 2 is added to the mixture, with this final combination mixed by gentle swirling.

The mixture then is applied to a washed and scraped skin surface. The mixture is uniformly spread on the skin and allowed to remain for ten minutes. The excess solution is removed by washing.

Example 2

Durable Topical Antifinal Preparation and Kit

A kit is provided for producing durable antifungal protection. The kit contains three components. Component 1 is a conjugate of an antifungal agent and a linking agent. This component is an aqueous solution, pH 6.4, containing 0.01 wt % polylysyl-amphotericin B conjugate, 10 v % ethanol, 0.1 v % propylene glycol, 0.5 mM EDTA, 0.1 wt % BHT. Component 2 is a calcium chloride activator solution as described for Example 1. Component 3 is a lyophilized transglutaminase preparation as described in Example 1. The three containers containing components 1, 2 and 3 are opened. Ten rnL of component 1 is added to component 3, and they are mixed by swirling. The mixture then is added to about 90 mL of component 1. To this mixture is added component 2. This final combination is mixed by gentle swirling. After this, the material is applied to the surface of skin as described in Example 1.

Example 3

Long-term Protective Preparation for Anticholinesterase Nerve Gas and Kit

A kit for providing long-term protection from anticholinesterase nerve gas is provided. Component 1 of the kit includes recombinant cholinesterase coupled to biotin (e.g., by reaction in the presence of N.N. succinimide). Component 2 is polyglutamine coupled to avidin. Component 2 is applied to the surface of the skin in the presence of transglutaminase, as described above in connection with Examples 1 and 2. After the avidin is coupled to the skin via the polyglutamine, then component 1 is added to bind the biotin to the avidin, thereby coupling the cholinesterase to the skin.

Example 4

A Mousse for Thickening Hair

A dispensing can with three reservoirs (a calcium ion solution, a transglutaminase solution and a hair bulking or thickening agent such as a mucopolysaccharide linked to polyglutamine) is provided. The three solutions are mixed, as is conventional with such dispensing cans, as they are being applied onto tissue such as hair. The mousse can be combed through the hair, left on the hair for at least ten minutes, and then rinsed.

Example 5

It has been shown in previous studies that polyglutamine attached to other peptides remains an excellent substrate of transglutauminase. Under optimal conditions, virtually all of the glutamine residues acted as amine acceptors in the reaction with an aliphatic amine, and lengthening the sequence of polyglutamine increases the reactivity of each glutamine residue. In the presence of transglutaminase, peptides containing polyglutamine become cross-linked to polylysine. The details of the reaction conditions and the manner of applying labels whereby the reaction may be visualized under UV light are described in detail in Kahlem et al., *Proc. Natl. Acad. Sci. USA*, 1996 93:14580–14585 (Appendix A). The same polyglutamines, but attached to agents as described herein, and, in general, the same conditions as described in Kahlem et al. may be applied in the above-described examples and, in general, in the practice of the present invention. The disclosure of this reference, as well as any other reference mentioned herein, is incorporated by reference in its entirety.

Example 6

Figure 2:
FIG. 2 depicts the skin of a mouse treated according to the invention.

Polyglutamine Containing a Fluorescent Marker is Covalently Attached to the Surface of the Skin Through the Action of Transglutaminase A. Mouse was epilated. Seven days later, a concentrated reaction solution containing guinea pig transglutaminase, dansyl labeled polyglutamine and $Ca^{2+}$ at 10 mM was applied to the left side (FIG. 2). The control (right side) was pretreated for 10 mins with 100 mM cystamine, the excess liquid was drained and the same reaction solution containing mM cystamine was applied. After 30 minutes, both sites were washed with a solution of 1% SDS. The mouse was then photographed under UV illumination (312 nm). The left side shows strong fluorescence of dansyl polyglutamine whereas the right side shows very weak fluorescence (FIG. 2).

Figure 3:
FIG. 3 depicts the mouse of FIG. 2 after 10 days.

B. Same mouse was photographed again five days later. There is still considerable fluorescence at the site of enzymatic coupling (left, FIG. 3), but the control fluorescence (right, FIG. 3) has virtually disappeared.

Reaction Solution

10 µl buffer containing 100 uM Tris pH8.2, 10 mM $CaCl_2$, and 10 mM DIT

3 µl dansylated polyglutamine (5 uM)

3 µl (13.3 mU/µl) partially purified guinea pig transglutaminase

It should be understood that the foregoing is merely a detailed description of certain preferred embodiments. It therefore should be apparent to those skilled in the art that various modification and equivalents can be made without departing from the spirit or scope of the invention. It is intended to encompass all such modifications withint the scope of the appended claims.

All references, patents and patent applications recited in this application are incorporated in their entirety herein by reference.

We claim:

1. A composition of matter comprising:

a conjugate of a nonextracellular matrix protein, nonlabeling agent and a carboxamide-carrying linking molecule, wherein the agent is selected from the group consisting of an anti-nerve gas agent, an anti-neurotoxin agent and an anti-glaucoma agent, wherein the agent is not itself a substrate of transglutaminase, wherein the agent, free of conjugation to the linking molecule, does not contain the linking molecule, and wherein the linking molecule comprises at least two contiguous linked glutamines, and is a substrate of transglutaminase.

2. The composition of claim 1, wherein the linking molecule comprises a polymer of amino acids containing at least 20% glutamines.

3. The composition of claim 1, wherein the linking molecule comprises at least 5 linked units, each unit being a carboxamide-bearing substrate for transglutaminase.

4. The composition of claim 1, wherein the linking molecule is 4 or more contiguous glutamines attached directly to one another by peptide bonds.

5. The composition of claim 1, wherein the agent is selected from the group consisting of a cholinesterase and a phosphodiesterase.

6. The composition of claim 1, wherein the agent is conjugated to the linking molecule by a bond that is hydrolyzable under physiological conditions.

7. The composition of claim 1, wherein the linking molecule comprises at least three contiguous linked glutamines.

8. The composition of claim 1, wherein the linking molecule comprises at least four contiguous linked glutamines.

9. The composition of claim 1, wherein the linking molecule comprises at least five contiguous linked glutamines.

10. The composition of claim 1, wherein the linking molecule comprises a polymer of amino acids containing at least 30% glutamines.

11. The composition of claim 1, wherein the linking molecule comprises a polymer of amino acids containing at least 40% glutamines.

12. The composition of claim 1, wherein the agent is an anti-nerve gas agent.

13. The composition of claim 1, wherein the agent is an antineurotoxin agent.

14. The composition of claim 1, wherein the agent is an anti-glaucoma agent.

15. A kit comprising a package housing:

a first container containing the composition of claim 1 and a second container containing transglutaminase.

16. The kit of claim 15, further comprising a third container housed by said package, the third container containing a linking molecule that is a substrate of transglutaminase and that is capable of covalently attaching to the composition contained in the first container in the presence of transglutaminase when the composition and the linking molecule are removed from the containers and contacted with each other.

17. The kit of claim 15, further comprising calcium housed by said package, except that said calcium is not in said second container.

18. A composition of matter comprising:

a conjugate of a nonextracellular matrix protein, nonlabeling agent and a polymer, wherein the agent is selected from the group consisting of an anti-nerve gas agent, an anti-neurotoxin agent and an anti-glaucoma agent, wherein the agent is not itself a substrate of transglutaminase, wherein the polymer comprises at least 3 contiguous lysines attached to one another by peptide bonds, and is a substrate of transglutaminase, and wherein the anti-glaucoma agent is Alprenoxime Hydrochloride, Colforsin, Dapiprazole Hydrochloride, Dipivefrin Hydrochloride, Naboctate Hydrochloride, Pilocarpine or Pirnabine.

19. The composition of claim 18, wherein the polymer is a polymer of amino acids, wherein at least 20% of the amino acids are lysines.

20. The composition of claim 18, wherein the agent is conjugated to the linking molecule by a bond that is hydrolyzable under physiological conditions.

21. The composition of claim 18, wherein the agent is selected from the group consisting of a cholinesterase and a phosphodiesterase.

22. The composition of claim 18, wherein the polymer comprises at least 4 contiguous lysines attached to one another by peptide bonds.

23. The composition of claim 18, wherein the polymer comprises at least 5 contiguous lysines attached to one another by peptide bonds.

24. The composition of claim 18, wherein the polymer is a polymer of amino acids, wherein at least 30% of the amino acids are lysines.

25. The composition of claim 18, wherein the polymer is a polymer of amino acids, wherein at least 40% of the amino acids are lysines.

26. The composition of claim 18, wherein the agent is an anti-nerve gas agent.

27. The composition of claim 18, wherein the agent is an antineurotoxin agent.

28. The composition of claim 18, wherein the agent is an anti-glaucoma agent.

29. A kit comprising a package housing:

a first container containing the composition of claim 18, and a second container containing transglutaminase.

30. The kit of claim 29, further comprising a third container housed by said package, the third container containing a linking molecule that is a substrate of transglutaminase and that is capable of covalently attaching to the composition contained in the first container in the presence of transglutaminase when the composition and the linking molecule are removed from the containers and contacted with each other.

31. The kit of claim 29, further comprising calcium housed by said package, except that said calcium is not in said second container.

32. A kit comprising a package housing:

a first container containing the composition of any one of claims 7, 12–14, 22 and 26–28, and a second container containing transglutaminase.

\* \* \* \* \*